US006964974B2

(12) United States Patent
Ackermann et al.

(10) Patent No.: US 6,964,974 B2
(45) Date of Patent: Nov. 15, 2005

(54) 2,3-OXIDOSQUALENE-LANOSTEROL CYCLASE INHIBITORS

(75) Inventors: Jean Ackermann, Riehen (CH); Johannes Aebi, Basel (CH); Alexander Chucholowski, San Diego, CA (US); Henrietta Dehmlow, Grenzach-Wyhlen (DE); Olivier Morand, Hegenheim (FR); Sabine Wallbaum, Ostfildern (DE); Thomas Weller, Binningen (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 216 days.

(21) Appl. No.: 09/939,872

(22) Filed: Aug. 27, 2001

(65) Prior Publication Data

US 2002/0068753 A1 Jun. 6, 2002

(30) Foreign Application Priority Data

Sep. 8, 2000 (EP) ........................................... 00119677

(51) Int. Cl.[7] ..................... A61K 31/445; C07D 211/96

(52) U.S. Cl. ....................... 514/331; 546/232; 546/229; 546/216; 514/327

(58) Field of Search ................................ 514/331, 327; 546/232, 229, 216

(56) References Cited

U.S. PATENT DOCUMENTS

| | | | | |
|---|---|---|---|---|
| 3,133,061 A | | 5/1964 | Kirchner | |
| 3,914,426 A | * | 10/1975 | Evanega et al. | 424/266 |
| 5,614,534 A | | 3/1997 | Binet et al. | |
| 5,681,841 A | | 10/1997 | Himmelsbach et al. | |
| 5,994,356 A | | 11/1999 | Himmelsbach et al. | |
| 6,034,275 A | | 3/2000 | Aebi et al. | |

FOREIGN PATENT DOCUMENTS

| | | |
|---|---|---|
| DE | 44 07 961 | 9/1995 |
| DE | 196 18 970 | 11/1997 |
| DE | 198 06 713 | 8/1999 |
| EP | 0 625 509 | 11/1994 |
| EP | 636 367 | 2/1995 |
| WO | WO 94 12181 | 6/1994 |
| WO | WO 95 18619 | 7/1995 |

OTHER PUBLICATIONS

Gotto et al., Circulation 81, pp. 1721–1733 (1990).
Stein et al., Nutr. Metab. Cardiovasc. Dis. 2, pp. 113–156 (1992).
Illingworth, Med. Clin. North Am. 84, pp. 23–42 (2000).
Ross et al., Arch. Intern. Med. 159, pp. 1793–1802 (1999).
Ellen et al., J. Cardiol. 81, pp. 60B–65B (1998).
Shepherd, Eur. Heart J. 16, pp. 5–13 (1995).
Davignon et al., Can. J. Cardiol 8, pp. 843–864 (1992).
Pedersen et al., Drug Safety 14, pp. 11–24 (1996).
Morand et al., J. Lipid Research 38, pp. 373–390 (1997).
Mark et al., J. Lipid Research 37, pp. 148–158 (1996).
Peffley et al., Biochem. Pharmacol 56, pp. 439–449 (1998).
Nelson et al., J. Biol. Chem. 256, pp. 1067–1068 (1981).
Spencer et al., J. Biol. Chem. 260, pp. 13391–13394 (1985).
Panini et al., J. Lipid Research 27, pp. 1190–1204 (1986).
Ness et al., Arch. Biochem. Biophys. 308, pp. 420–425 (1994).
Janowski et al., Proc. Natl. Acad. Sci. USA 96, pp. 266–271 (1999).
Venkateswaran et al., J. Biol. Chem. 275, pp. 14700–14707 (2000).
Costet et al., J. Biol. Chem. 275, pp. 28240–28245 (2000).
Ordovas et al., Nutr. Rev. 58, pges. 76–79 (2000).
Schmitz et al., Front. Biosci 6, D505–D514 (2001).
Tobin et al., Mol. Endocrinol. 14, pp. 741–752 (2000).
Marshall et al., J. Org. Chem. 61(17), pp. 5729–5735 (1996).
Baker et al., J. Chem. Soc. Perkin Trans. 1, pp. 1415–1421 (1990).
Belostotkii et al., Tetrahedron Letters 35(28), pp. 5075–5076 (1994).
Bartlett et al., J. Am. Chem. Soc. 106, pp. 7854–7860 (1984).
Cooper et al., Synthesis 4, pp. 621–625 (2001).

* cited by examiner

*Primary Examiner*—Charanjit S. Aulakh
(74) *Attorney, Agent, or Firm*—George W. Johnston; Peter Tu

(57) ABSTRACT

The present invention relates to piperidine derivatives useful for the treatment and/or prophylaxis of diseases which are associated with 2,3-oxidosqualene-lanosterol cyclase such as hypercholesterolemia, hyperlipemia, arteriosclerosis, vascular diseases, mycoses, gallstones, tumors and/or hyperproliferative disorders, and treatment and/or prophylaxis of impaired glucose tolerance and diabetes.

90 Claims, No Drawings

2,3-OXIDOSQUALENE-LANOSTEROL CYCLASE INHIBITORS

FIELD OF THE INVENTION

The present invention is concerned with piperidine derivatives, their manufacture and their use as 2,3-oxidosqualene-lanosterol cyclase inhibiting medicaments.

BACKGROUND OF THE INVENTION

Causal risk factors that directly promote the development of coronary and peripheral atherosclerosis include elevated low-density lipoprotein cholesterol (LDL-C), low high-density lipoprotein cholesterol (HDL-C), hypertension, cigarette smoking and diabetes mellitus. Other synergistic risk factors include elevated concentrations of triglyceride (TG)-rich lipoproteins, small, dense low-density lipoprotein particles, lipoprotein (a) (Lp(a)), and homocysteine. Predisposing risk factors modify the causal or conditional risk factors and thus affect atherogenesis indirectly. The predisposing risk factors are obesity, physical inactivity, family history of premature CVD, and male sex. The strong connection between coronary heart disease (CHD) and high LDL-C levels in plasma, and the therapeutic advantage of lowering elevated LDL-C levels are now well established (Gotto et al., Circulation 81, 1990, 1721–1733; Stein et al., Nutr. Metab. Cardiovasc. Dis. 2, 1992, 113–156; Illingworth, Med. Clin. North. Am. 84, 2000, 23–42). Cholesterol-rich, sometimes unstable, atherosclerotic plaques lead to the occlusion of blood vessels resulting in an ischemia or an infarct. Studies with respect to primary prophylaxis have shown that a lowering of plasma LDL-C levels in plasma reduces the frequency of non-fatal incidences of CHD, while the overall morbidity remains unchanged. The lowering of plasma LDL-C levels in patients with pre-established CHD (secondary intervention) reduces CHD mortality and morbidity; meta-analysis of different studies shows that this decrease is proportional to the reduction of the LDL-C (Ross et al., Arch. Intern. Med. 159, 1999, 1793–1802).

The clinical advantage of cholesterol lowering is greater for patients with pre-established CHD than for asymptomatic persons with hypercholesterolemia. According to current guidelines, cholesterol lowering treatment is recommended for patients who had survived a myocardial infarct or patients suffering from angina pectoris or another atherosclerotic disease, with a target LDL-C level of 100 mg/dl.

Preparations such as bile acid sequestrants, fibrates, nicotinic acid, probucol as well as statins, i.e. HMG-Co-A reductase inhibitors such as simvastatin and atorvastatin, are used for usual standard therapies. The best statins reduce plasma LDL-C effectively by at least 40%, and also plasma triglycerides, a synergistic risk factor, but less effectively. In contrast, fibrates reduce plasma triglycerides effectively, but not LDL-C. Combination of a statin and a fibrate proved to be very efficacious in lowering LDL-C and triglycerides (Ellen and McPherson, J. Cardiol. 81, 1998, 60B–65B), but safety of such a combination remains an issue (Shepherd, Eur. Heart J. 16, 1995, 5–13). A single drug with a mixed profile combining effective lowering of both LDL-C and triglycerides would provide additional clinical benefit to asymptomatic and symptomatic patients.

In humans, statins are well tolerated at standard dosage, but reductions in non-sterol intermediates in the cholesterol synthesis pathway, such as isoprenoids and coenzyme Q, may be associated with adverse clinical events at high doses (Davignon et al., Can. J. Cardiol. 8, 1992, 843–864; Pederson and Tobert, Drug Safety 14, 1996, 11–24).

This has stimulated the search for, and development of compounds that inhibit cholesterol biosynthesis, yet act distal to the synthesis of these important, non-sterol intermediates. 2,3-oxidosqualene:lanosterol cyclase (OSC), a microsomal enzyme, represents a unique target for a cholesterol-lowering drug (Morand et al., J. Lipid Res., 38, 1997, 373–390; Mark et al., J. Lipid Res. 37, 1996, 148–158). OSC is downstream of farnesyl-pyrophosphate, beyond the synthesis of isoprenoids and coenzyme Q. In hamsters, pharmacologically active doses of an OSC inhibitor showed no adverse side-effects, in contrast to a statin which reduced food-intake and body weight, and increased plasma bilirubin, liver weight and liver triglyceride content (Morand et al., J. Lipid Res., 38, 1997, 373–390). The compounds described in European Patent Application No. 636 367, which inhibit OSC and which lower the total cholesterol in plasma, belong to these substances.

OSC inhibition does not trigger the overexpression of HMGR because of an indirect, negative feed-back regulatory mechanism involving the production of 24(S),25-epoxycholesterol (Peffley et al., Biochem. Pharmacol. 56, 1998, 439–449; Nelson et al., J. Biol. Chem. 256, 1981, 1067–1068; Spencer et al., J. Biol. Chem. 260, 1985, 13391–13394; Panini et al., J. Lipid Res. 27, 1986, 1190–1204; Ness et al., Arch. Biochem. Biophys. 308, 1994, 420–425). This negative feed-back regulatory mechanism is fundamental to the concept of OSC inhibition because (i) it potentiates synergistically the primary inhibitory effect with an indirect down-regulation of HMGR, and (ii) it prevents the massive accumulation of the precursor monooxidosqualene in the liver. In addition, 24(S),25-epoxycholesterol was found to be one of the most potent agonists of the nuclear receptor LXR (Janowski et al., Proc. Natl. Acad. Sci. USA, 96, 1999, 266–271). Considering that 24(S),25-epoxycholesterol is a by-product of inhibition of OSC it is hypothesized that the OSC inhibitors could also indirectly activate LXR-dependent pathways such as (i) cholesterol-7alpha-hydroxylase to increase the consumption of cholesterol via the bile acid route, (ii) expression of ABC proteins with the potential to stimulate reverse cholesterol transport and increase plasma HDL-C levels (Venkateswaran et al., J. Biol. Chem. 275, 2000, 14700–14707; Costet et al., J. Biol. Chem. June 2000, in press; Ordovas, Nutr Rev 58, 2000, 76–79, Schmitz and Kaminsky, Front Biosci 6, 2001, D505–D514), and/or inhibit intestinal cholesterol absorption (Mangelsdorf, XIIth International Symposium on Atherosclerosis, Stockholm, June 2000). In addition, possible cross talks between fatty acid and cholesterol metabolism mediated by liver LXR have been hypothesized (Tobin et al., Mol. Endocrinol. 14, 2000, 741–752).

SUMMARY OF THE INVENTION

The compounds of the present invention inhibit 2,3-oxidosqualene-lanosterol cyclase (EC 5.4.99.) which is required for the biosynthesis of cholesterol, ergosterol and other sterols.

In particular, the invention relates to compounds of the formula (I)

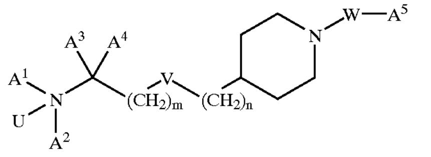

(I)

wherein

U is O or a lone pair,

V is O, —$CH_2$—, —CH═CH—, or —C≡C—, m and n independently from each other are 0 to 7 and m+n is 0 to 7, W is CO, COO, $CONR^1$, CSO, $CSNR^1$, $SO_2$, or $SO_2NR^1$, with the proviso that:

a) V is not —$CH_2$— if W is CO, b) m+n is 1 to 2 if V is —$CH_2$— and W is $SO_2$, c) m=n=0 if V is —CH═CH— and W is CO or $SO_2$, d) m is 1 to 7 if V is O, e) n is 1 to 6 or m+n is 1 to 3 if V is O and W is CO or $SO_2$, $A^1$ is H, lower-alkyl or lower-alkenyl, $A^2$ is cycloalkyl, cycloalkyl-lower-alkyl, lower-alkenyl, lower-alkynyl; or lower-alkyl optionally substituted with hydroxy, lower-alkoxy or lower-alkoxy-carbonyl, $A^3$ and $A^4$ are hydrogen or lower-alkyl, or $A^1$ and $A^2$ or $A^1$ and $A^3$ are bonded to each other to form a ring and —$A^1$—$A^2$— or —$A^1$—$A^3$— are lower-alkylene or lower-alkenylene, optionally substituted by $R^2$, in which one —$CH_2$— group of —$A^1$—$A^2$— or —$A^1$—$A^3$— can optionally be replaced by $NR^3$, S, or O, $A^5$ is lower-alkyl optionally substituted with halogen; lower-alkenyl, lower-alkoxy-carbonyl-lower-alkyl, cycloalkyl, cycloalkyl-lower-alkyl, aryl, aryl-lower-alkyl, heteroaryl, or heteroaryl-lower-alkyl, $R^2$ is lower-alkyl, hydroxy, hydroxy-lower-alkyl, or N($R^4$, $R^5$), $R^1$, $R^3$, $R^4$ and $R^5$ independently from each other are hydrogen or lower-alkyl, and pharmaceutically acceptable salts and/or pharmaceutically acceptable esters thereof.

The present compounds of formula I inhibit OSC and therefore also inhibit the biosynthesis of cholesterol, ergosterol and other sterols, and reduce the plasma cholesterol levels. They can therefore be used in the therapy and prophylaxis of hypercholesterolemia, hyperlipemia, arteriosclerosis and vascular diseases in general. Furthermore, they can be used in the therapy and/or prevention of mycoses, parasite infections, gallstones, cholestatic liver disorders, tumors and hyperproliferative disorders, e.g. hyperproliferative skin and vascular disorders. In addition, it has unexpectedly been found that the compounds of the present invention can also be of therapeutical use to improve glucose tolerance in order to treat and/or prevent related diseases such as diabetes. The compounds of the present invention further exhibit improved pharmacological properties compared to known compounds.

DETAILED DESCRIPTION OF THE INVENTION

Unless otherwise indicated the following definitions are set forth to illustrate and define the meaning and scope of the various terms used to describe the invention herein.

In this specification the term "lower" is used to mean a group consisting of one to seven, preferably of one to four carbon atom(s).

The term "lone pair" refers to an unbound electron pair, in particular to the unbound electron pair of a nitrogen atom in e.g. an amine.

The term "halogen" refers to fluorine, chlorine, bromine and iodine, with fluorine, chlorine and bromine being preferred.

The term "alkyl", alone or in combination with other groups, refers to a branched or straight-chain monovalent saturated aliphatic hydrocarbon radical of one to twenty carbon atoms, preferably one to sixteen carbon atoms. Alkyl groups can optionally be substituted e.g. with halogen, particularly with flourine or chlorine, hydroxy, lower-alkoxy, e.g. methoxy or ethoxy, and/or lower-alkoxy-carbonyl, e.g. acetoxy.

The term "lower-alkyl", alone or in combination with other groups, refers to a branched or straight-chain monovalent alkyl radical of one to seven carbon atoms, preferably one to four carbon atoms. This term is further exemplified by such radicals as methyl, ethyl, n-propyl, isopropyl, n-butyl, s-butyl, t-butyl and the like. A lower-alkyl group may optionally have a substitution pattern as described earlier in connection with the term "alkyl".

The term "cycloalkyl" refers to a monovalent carbocyclic radical of 3 to 10 carbon atom(s), preferably 3 to 6 carbon atoms. Cycloalkyl in which one or more —$CH_2$— group is replaced by O, S, NH or N(lower-alkyl) are referred to as "heterocycloalkyl".

The term "alkoxy" refers to the group R'—O—, wherein R' is an alkyl. The term "lower-alkoxy" refers to the group R'—O—, wherein R' is a lower-alkyl. The term "thio-alkoxy" refers to the group R'—S—, wherein R' is an alkyl. The term "thio-lower-alkoxy" refers to the group R'—S—, wherein R' is a lower-alkyl.

The term "alkenyl", alone or in combination with other groups, stands for a straight-chain or branched hydrocarbon residue comprising an olefinic bond and up to 20, preferably up to 16 carbon atoms. The term "lower-alkenyl" refers to a straight-chain or branched hydrocarbon residue comprising an olefinic bond and up to 7, preferably up to 4 carbon atoms, such as e.g. 2-propenyl. An alkenyl or lower-alkenyl group may optionally have a substitution pattern as described earlier in connection with the term "alkyl".

The term "alkynyl", alone or in combination with other groups, stands for a straight-chain or branched hydrocarbon residue comprising a tripple bond and up to 20, preferably up to 16 carbon atoms. The term "lower-alkynyl" refers to a straight-chain or branched hydrocarbon residue comprising a tripple bond and up to 7, preferably up to 4 carbon atoms, such as e.g. 2-propinyl. An alkynyl or lower-alkynyl group may optionally have a substitution pattern as described earlier in connection with the term "alkyl".

The term "alkylene" refers to a straight chain or branched divalent saturated aliphatic hydrocarbon group of 1 to 20 carbon atoms, preferably 1 to 16 carbon atoms. The term "lower-alkylene" refers to a straight chain or branched divalent saturated aliphatic hydrocarbon group of 1 to 7, preferably 3 to 6 carbon atoms. An alkylene or lower-alkylene group may optionally have a substitution pattern as described earlier in connection with the term "alkyl".

The term "alkenylene" refers to a straight chain or branched divalent hydrocarbon group comprising an olefinic bond and up to 20 carbon atoms, preferably up to 16 carbon atoms. The term "lower-alkenylene" refers to a straight chain or branched divalent hydrocarbon group comprising an olefinic bond and up to 7, preferably up to 6 C-atoms. An alkenylene or lower-alkenylene group may optionally have a substitution pattern as described earlier in connection with the term "alkyl".

The term "aryl" relates to the phenyl or naphthyl group which can optionally be substituted by 1 to 3 substituents selected from the group consisting of lower-alkyl, dioxo-lower-alkylene (forming e.g. a benzodioxyl group), halogen, hydroxy, cyano, $CF_3$, $NH_2$, N(lower-alkyl)$_2$, aminocarbonyl, carboxy, nitro, lower-alkoxy, thio-lower-alkoxy, lower-alkylcarbonyl, lower-alkylcarbonyloxy, aryl, or aryloxy. Preferred substituents are lower-alkyl, lower-alkoxy, thio-lower-alkoxy, lower-alkyl-carbonyl, lower-alkoxycarbonyl, fluorine, chlorine, bromine, CN, $CF_3$, and/or dioxo-lower-alkylene. More preferred substituents are fluorine, chlorine, bromine and $CF_3$.

The term "heteroaryl" refers to an aromatic 5- or 6-membered ring which can comprise 1, 2 or 3 atoms selected from nitrogen, oxygen and/or sulphur such as furyl, pyridyl, 1,2-, 1,3- and 1,4-diazinyl, thienyl, isoxazolyl, oxazolyl, imidazolyl, or pyrrolyl. The term "heteroaryl" further refers to bicyclic aromatic groups comprising two 5- or 6-membered rings, in which one or both rings can contain 1, 2 or 3 atoms selected from nitrogen, oxygen or sulphur such as e,g, indol or chinolin, or partially hydrogenated bicyclic aromatic groups such as e.g. indolinyl. A heteroaryl group may optionally have a substitution pattern as described earlier in connection with the term "aryl".

The term "pharmaceutically acceptable salts" embraces salts of the compounds of formula (I) with inorganic or organic acids such as hydrochloric acid, hydrobromic acid, nitric acid, sulphuric acid, phosphoric acid, citric acid, formic acid, maleic acid, acetic acid, fumaric acid, succinic acid, tartaric acid, methanesulphonic acid, p-toluenesulphonic acid and the like, which are non toxic to living organisms. Preferred salts are formiates, hydrochlorides and hydrobromides.

The term "pharmaceutically acceptable esters" embraces esters of the compounds of formula (I), in which hydroxy groups have been converted to the corresponding esters with inorganic or organic acids such as nitric acid, sulphuric acid, phosphoric acid, citric acid, formic acid, maleic acid, acetic acid, succinic acid, tartaric acid, methanesulphonic acid, p-toluenesulphonic acid and the like, which are non toxic to living organisms.

In detail, the present invention relates to compounds of formula (I)

(I)

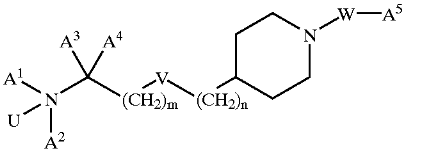

wherein

U is O or a lone pair,

V is O, —$CH_2$—, —CH═CH—, or —C≡C—, m and n independently from each other are 0 to 7 and m+n is 0 to 7, W is CO, COO, $CONR^1$, CSO, $CSNR^1$, $SO_2$, or $SO_2NR^1$, with the proviso that:

V is not —$CH_2$— if W is CO, b) m+n is 1 to 2 if V is —$CH_2$— and W is $SO_2$, c) m=n=0 if V is —CH═CH— and W is CO or $SO_2$, d) m is 1 to 7 if V is O, e) n is 1 to 6 or m+n is 1 to 3 if V is O and W is CO or $SO_2$, $A^1$ is H, lower-alkyl or lower-alkenyl, $A^2$ is cycloalkyl, cycloalkyl-lower-alkyl, lower-alkenyl, lower-alkynyl; or lower-alkyl optionally substituted with hydroxy, lower-alkoxy or lower-alkoxy-carbonyl, $A^3$ and $A^4$ are hydrogen or lower-alkyl, or $A^1$ and $A^2$ or $A^1$ and $A^3$ are bonded to each other to form a ring and —$A^1$—$A^2$— or —$A^1$—$A^3$— are lower-alkylene or lower-alkenylene, optionally substituted by $R^2$, in which one —$CH_2$— group of —$A^1$—$A^2$— or —$A^1$—$A^3$— can optionally be replaced by $NR^3$, S, or O, $A^5$ is lower-alkyl optionally substituted with halogen; lower-alkenyl, lower-alkoxy-carbonyl-lower-alkyl, cycloalkyl, cycloalkyl-lower-alkyl, aryl, aryl-lower-alkyl, heteroaryl, or heteroaryl-lower-alkyl, $R^2$ is lower-alkyl, hydroxy, hydroxy-lower-alkyl, or N($R^4$, $R^5$), $R^1$, $R^3$, $R^4$ and $R^5$ independently from each other are hydrogen or lower-alkyl, and pharmaceutically acceptable salts and/or pharmaceutically acceptable esters thereof.

Preferred are compounds of formula (I) and/or pharmaceutically acceptable salts thereof. Other preferred embodiments relate to compounds of formula (I) wherein U is a lone pair or to compounds of formula (I) wherein U is O. Compounds as described above in which V is O relate to a further preferred embodiment of the present invention. Other preferred compounds of the present invention are those wherein V is —C≡C—. Compounds in which V is —$CH_2$— are also preferred.

Of the compounds of the present invention, those in which W represents CO, COO, $CONR^1$, $SO_2$ or $SO_2NR^1$ and $R^1$ is hydrogen are preferred, with those wherein W represents CO, COO or $SO_2NR^1$ and $R^1$ is hydrogen being particularly preferred. Other preferred compounds are those in which W is CO. Compounds wherein W is $SO_2$ are also preferred.

Compounds of the present invention in which n is 0 to 2 are preferred, with those wherein n is 1 to 2 being particularly preferred and those wherein n is 0 separately being particularly preferred. Another preferred embodiment relates to compounds as defined above, wherein m is 1 to 5. Compounds wherein m is 0 to 2 also are preferred.

Other preferred compounds of the present invention are those in which $A^1$ represents methyl, ethyl, or 2-propenyl. Another group of preferred compounds of the present invention are those in which $A^2$ represents methyl, n-propyl, i-propyl, n-butyl, 2-propenyl, 2-propinyl, cyclopropyl, cyclohexyl, cyclopropyl-methylene; or ethyl optionally substituted with hydroxy, methoxy, or ethoxycarbonyl, with those compounds wherein $A^2$ represents n-propyl, 2-hydroxy-ethyl, 2-methoxy-ethyl, 2-propenyl, or cyclopropyl being especially preferred.

Compounds of formula (I), wherein $A^1$ and $A^2$ are bonded to each other to form a ring and —$A^1$—$A^2$— is lower-alkylene, or lower-alkenylene, optionally substituted by $R^2$, in which one —$CH_2$— group of —$A^1$—$A^2$— can optionally be replaced by $NR^3$, S, or O, wherein $R^2$ is lower-alkyl, hydroxy, hydroxy-lower-alkyl, or N(lower-alkyl)$_2$, and $R^3$ is lower-alkyl are also preferred, with those compounds wherein said optional substituent $R^2$ is methyl, hydroxy, 2-hydroxyethyl, or $N(CH_3)_2$ and $R_3$ is methyl being particularly preferred. In compounds wherein $A^1$ and $A^2$ are bonded to each other to form a ring, said ring is preferrably a 4-, 5-, or 6-membered ring such as e.g. piperidinyl or pyrrolidinyl.

A further preferred embodiment of the present invention relates to compounds of formula (I), wherein $A^3$ and/or $A^4$ represent hydrogen.

Compounds of formula (I), wherein $A^5$ as defined above is not heteroaryl or wherein $A^5$ is lower-alkyl optionally substituted by 1 to 3 substituents selected from the group consisting of fluorine and chlorine; lower-alkenyl, cycloalkyl, cycloalkyl-lower-alkyl, lower-alkoxy-carbonyl-lower-alkyl, naphthyl, furyl-methylene; or phenyl, benzyl or phenyl-ethylene, optionally substituted by 1 to 3 substituents selected from the group consisting of fluorine, chlorine, bromine, CN, $CF_3$, $NO_2$, lower-alkyl, lower-alkoxy, thio-lower-alkoxy, lower-alkyl-carbonyl, lower-alkoxy-carbonyl, and dioxo-lower-alkylene are other preferred embodiments of the present invention, with those compounds wherein $A^5$ is lower-alkyl, cycloalkyl-lower-alkyl; or phenyl or benzyl optionally substituted by 1 to 3 substituents selected from the group consisting of fluorine, chlorine, bromine, and $CF_3$ being more preferred, and with those compounds wherein wherein $A^5$ is n-butyl, i-butyl, cyclohexyl-methylene, phenyl, 4-chloro-phenyl, 4-bromo-phenyl, 2,5-difluoro-phenyl, 3,4-difluoro-phenyl, 4-trifluoromethyl-phenyl, or 4-chloro-benzyl being particularly preferred. Above mentioned optional subsituents are bound to said phenyl rings or to the phenyl ring in said benzyl group.

Further preferred embodiments of the present invention are those compounds as defined above wherein V is not $—CH_2—$ or —CH═CH— if W is CO or $SO_2$, or wherein W is not CO and/or $SO_2$ at all.

Particularly prefered embodiments of the present invention are compounds of formula (Ia)

(Ia)

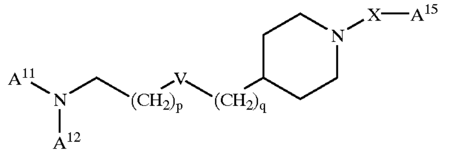

wherein

V is O, $—CH_2—$, —CH═CH—, or —C≡C—;

p is an integer from 0 to 5;

q 0, 1 or 2;

X is CO, COO, $SO_2$, or $SO_2NH$, with the provisos that:

V is not $—CH_2—$ when X is CO, b) p+q is 1 or 2 when V is $—CH_2—$ and X is $SO_2$, c) p═q═0 when V is —CH═CH— and X is CO or $SO_2$, d) p is 1 to 5 when V is O, and e) p is 1 to 3 when V is O, X is CO or $SO_2$, and q is 0;

$A^{11}$ is methyl or ethyl;

$A^{12}$ is cyclopropyl, lower-alkenyl, or lower-alkyl optionally substituted with hydroxy or lower-alkoxy; and $A^{15}$ is lower-alkyl optionally substituted with halogen, lower-alkenyl, lower-alkoxy-carbonyl-lower-alkyl, cycloalkyl, cycloalkyl-lower-alkyl, aryl, aryl-lower-alkyl, heteroaryl, or heteroaryl-lower-alkyl;

and pharmaceutically acceptable salts or esters thereof.

Most prefered compounds of formula (Ia) include those wherein $A^{12}$ is cyclopropyl, lower alkenyl of 2 to 4 carbon atoms, lower alkyl of 1 to 4 carbon atoms, lower alkoxy of 1 to 4 carbon atoms or a lower alkyl substituted with a lower-alkoxy having a total of 2 to 4 carbon atoms. Also preferred are those compounds of formula (Ia) wherein $A^{15}$ is lower alkyl, cycloalkyl, cycloalkyl-lower alkyl, aryl or aryl-lower-alkyl.

Preferred compounds of general formula (I) are those selected from the group consisting of {4-[4-(Allyl-methyl-amino)-butoxy]-piperidin-1-yl}-(4-bromo-phenyl)-methanone, {4-[3-(Allyl-methyl-amino)-propoxy]-piperidin-1-yl}-(4-bromo-phenyl)-methanone, Allyl-{4-[1-(4-chloro-benzenesulfonyl)-piperidin-4-yloxy]-butyl}-methyl-amine, Allyl-{4-[1-(4-bromo-benzenesulfonyl)-piperidin-4-yloxy]-butyl}-methyl-amine, Allyl-{3-[1-(4-bromo-benzenesulfonyl)-piperidin-4-yloxy]-propyl}-methyl-amine, 1-{4-[5-(Allyl-methyl-amino)-pentyloxy]-piperidin-1-yl}-2-(4-fluoro-phenyl)-ethanone, 1-[4-(5-Diethylamino-pentyloxy)-piperidin-1-yl]-2-(4-fluoro-phenyl)-ethanone, 2-(4-Fluoro-phenyl)-1-(4-{5-[(2-methoxy-ethyl)-methyl-amino]-pentyloxy}-piperidin-1-yl)-ethanone, 1-{4-[5-(Cyclopropyl-methyl-amino)-pentyloxy]-piperidin-1-yl}-2-(4-fluoro-phenyl)-ethanone, 1-{4-[4-(Allyl-methyl-amino)-butoxy]-piperidin-1-yl}-2-(4-chloro-phenyl)-ethanone, 2-(4-Chloro-phenyl)-1-(4-{4-[ethyl-(2-hydroxy-ethyl)-amino]-butoxy}-piperidin-1yl)-ethanone, {4-[4-(Allyl-methyl-amino)-butoxy]-piperidin-1-yl}-(4-chloro-phenyl)-methanone, (4-Chloro-phenyl)-(4-{4-[ethyl-(2-hydroxy-ethyl)-amino]-butoxy}-piperidin-1-yl)-methanone, 4-[4-(Allyl-methyl-amino)-butoxy]-piperidine-1-carboxylic acid 4-chloro-phenyl ester, 4-{4-[Ethyl-(2-hydroxy-ethyl)-amino]-butoxy}-piperidine-1-carboxylic acid 4-chloro-phenyl ester, 4-[4-(Allyl-methyl-amino)-butoxy]-piperidine-1-carboxylic acid isobutyl ester, 4-{4-[Ethyl-(2-hydroxy-ethyl)-amino]-butoxy}-piperidine-1-carboxylic acid isobutyl ester, 1-(4-{2-[4-(Allyl-methyl-amino)-butoxy]-ethyl}-piperidin-1-yl)-2-(4-chloro-phenyl)-ethanone, 2-(4-Chloro-phenyl)-1-[4-(2-{4-[ethyl-(2-hydroxy-ethyl)-amino]-butoxy}-ethyl)-piperidine-1-yl]-ethanone, (4-{2-[4-(Allyl-methyl-amino)-butoxy]-ethyl}-piperidin-1-yl)-(4-chloro-phenyl)-methanone, (4-Chloro-phenyl)-[4-(2-{4-[ethyl-(2-hydroxy-ethyl)-amino]-butoxy}-ethyl)-piperidin-1-yl]-methanone, 4-{2-[4-(Allyl-methyl-amino)-butoxy]-ethyl}-piperidine-1-carboxylic acid 4-chloro-phenyl ester, 4-(2-{4-[Ethyl-(2-hydroxy-ethyl)-amino]-butoxy}-ethyl)-piperidine-1-carboxylic acid 4-chloro-phenyl ester, 4-{2-[4-(Allyl-methyl-amino)-butoxy]-ethyl}-piperidine-1-carboxylic acid isobutyl ester, 4-(2-{4-[Ethyl-(2-hydroxy-ethyl)-amino]-butoxy}-ethyl)-piperidine-1-carboxylic acid isobutyl ester, 1-(4-{2-[2-(Allyl-methyl-amino)-ethoxy]-ethyl}-piperidin-1-yl)-2-(4-chloro-phenyl)-ethanone, 2-(4-Chloro-phenyl)-1-[4-(2-{2-[ethyl-(2-hydroxy-ethyl)-amino]-ethoxy}-ethyl)-piperidin-1-yl]-ethanone, (4-{2-[2-(Allyl-methyl-amino)-ethoxy]-ethyl}-piperidin-1-yl)-(4-chloro-phenyl)-methanone, (4-Chloro-phenyl)-[4-(2-{2-[ethyl-(2-hydroxy-ethyl)-amino]-ethoxy}-ethyl)-piperidin-1-yl]-methanone, 4-{2-[2-(Allyl-methyl-amino)-ethoxy]-ethyl}-piperidine-1-carboxylic acid 4-chloro-phenyl ester, 4-(2-{2-[Ethyl-(2-hydroxy-ethyl)-amino]-ethoxy}-ethyl)-piperidine-1-carboxylic acid 4-chloro-phenyl ester, 4-{2-[2-(Allyl-methyl-amino)-ethoxy]-ethyl}-piperidine-1-carboxylic acid isobutyl ester, 4-(2-{2-[Ethyl-(2-hydroxy-ethyl)-amino]-ethoxy}-ethyl)-piperidine-1-carboxylic acid isobutyl ester, 1-(4-{2-[3-(Allyl-methyl-amino)-propoxy]-ethyl}-piperidin-1-yl)-2-(4-chloro-phenyl)-ethanone, 2-(4-Chloro-phenyl)-1-[4-(2-{3-[ethyl-(2-hydroxy-ethyl)-amino]-propoxy}-ethyl-piperidin-1-yl]-ethanone, (4-{2-[3-(Allyl-methyl-amino)-propoxy]-ethyl}-piperidin-1-yl)-(4-chloro-phenyl)-methanone, (4-Chloro-phenyl)-[4-(2-{3-[ethyl-(2-hydroxy-ethyl)-amino]-propoxy}-ethyl)-piperidin-1-yl]-methanone, 4-{2-[3-(Allyl-methyl-amino)-propoxy]-ethyl}-piperidine-1-carboxylic acid 4-chloro-phenyl ester, 4-(2-{3-[Ethyl-(2-hydroxy-ethyl)-amino]-propoxy}-ethyl)-piperidine-1-carboxylic acid 4-chloro-phenyl ester, 2-(4-Chloro-phenyl)-1-(4-{4-[ethyl-(2-hydroxy-ethyl)-amino]-butoxymethyl}-piperidin-1-yl)-ethanone, 1-{4-[4-(Allyl-methyl-amino)-butoxymethyl]-piperidin-1-yl}-2-(4-chloro-phenyl)-ethanone, {4-[4-(Allyl-methyl-amino)-butoxymethyl]-piperidin-1-yl}-(4-chloro-phenyl)-methanone, (4-Chloro-phenyl)-(4-{4-[ethyl-(2-hydroxy-ethyl)-amino]-butoxymethyl}-piperidin-1-yl)-methanone, 1-{4-[3-(Allyl-methyl-amino)-propoxymethyl]-piperidin-1-yl}-2-(4-chloro-phenyl)-ethanone, 2-(4-Chloro-phenyl)-1-(4-{3-[ethyl-(2-hydroxy-ethyl)-amino]-propoxymethyl}-piperidin-1-yl)-ethanone, {4-[3-(Allyl-methyl-amino)-propoxymethyl]-piperidin-1-yl}-(4-chloro-phenyl)-methanone, (4-Chloro-phenyl)-(4-{3-[ethyl-(2-hydroxy-ethyl)-amino]-propoxymethyl}-piperidin-1-yl)-methanone, 4-[3-(Allyl-methyl-amino)-propoxymethyl]-piperidine-1-carboxylic acid 4-chloro-phenyl ester, 4-{3-[Ethyl-(2-hydroxy-ethyl)-amino]-propoxymethyl}-piperidine-1-carboxylic acid 4-chloro-phenyl ester, 4-[4-(Allyl-methyl-amino)-butoxymethyl]-piperidine-1-carboxylic acid 4-chloro-phenyl ester, 4-{4-[Ethyl-(2-hydroxy-ethyl)-amino]-butoxymethyl}-piperidine-1-carboxylic acid 4-chloro-phenyl ester, 4-[6-(Allyl-methyl-amino)-hexyloxy]-piperidine-1-carboxylic acid (4-fluoro-3-trifluoromethyl-phenyl)-amide, 4-[6-(Allyl-methyl-amino)-hexyloxy]-piperidine-1-carboxylic acid (2,4-difluoro-phenyl)-amide, 4-[6-(Allyl-methyl-amino)-hexyloxy]-piperidine-1-carboxylic acid (2,4-dimethoxy-phenyl)-amide, 4-[6-(Allyl-methyl-amino)-hexyloxy]-piperidine-1-carboxylic acid (4-fluoro-phenyl)-amide, 4-[6-(Allyl-methyl-amino)-hexyloxy]-piperidine-1-carboxylic acid (4-methoxy-phenyl)-amide, 4-[6-(Allyl-methyl-amino)-hexyloxy]-piperidine-1-carboxylic acid p-tolylamide, 4-[6-(Allyl-methyl-amino)-hexyloxy]-piperidine-1-carboxylic acid (4-methoxy-2-methyl-phenyl)-amide, 4-[6-(Allyl-methyl-amino)-hexyloxy]-piperidine-1-carboxylic acid (2,4-dimethyl-phenyl)-amide, 4-[6-(Allyl-methyl-amino)-hexyloxy]-piperidine-1-carboxylic acid (3,4,5-trimethoxy-phenyl)-amide, 4-[6-(Allyl-methyl-amino)-hexyloxy]-piperidine-1-carboxylic acid (3,4-dimethyl-phenyl)-amide, 4-[6-(Allyl-methyl-amino)-hexyloxy]-piperidine-1-carboxylic acid (4-acetyl-phenyl)-amide, 4-[6-(Allyl-methyl-amino)-hexyloxy]-piperidine-1-carboxylic acid (4-butyl-phenyl)-amide, 4-[6-(Allyl-methyl-amino)-hexyloxy]-piperidine-1-carboxylic acid (4-methylsulfanyl-phenyl)-amide, 4-[6-(Allyl-methyl-amino)-hexyloxy]-piperidine-1-carboxylic acid (4-isopropyl-phenyl)-amide, 4-[6-(Allyl-methyl-amino)-hexyloxy]-piperidine-1-carboxylic acid (3,4-dichloro-phenyl)-amide, 4-[6-(Allyl-methyl-amino)-hexyloxy]-piperidine-1-carboxylic acid (4-bromo-phenyl)-amide, 4-[6-(Allyl-methyl-amino)-hexyloxy]-piperidine-1-carboxylic acid naphthalen-2-ylamide, 4-[6-(Allyl-methyl-amino)-hexyloxy]-piperidine-1-carboxylic acid naphthalen-1-ylamide, 4-[6-(Allyl-methyl-amino)-hexyloxy]-piperidine-1-carboxylic acid phenethyl-amide, 4-[6-(Allyl-methyl-amino)-hexyloxy]-piperidine-1-carboxylic acid ethyl ester, 4-[6-(Allyl-methyl-amino)-hexyloxy]-piperidine-1-carboxylic acid 9H-fluoren-9-ylmethyl ester, 4-[6-(Allyl-methyl-amino)-hexyloxy]-piperidine-1-carboxylic acid methyl ester, 4-[6-(Allyl-methyl-amino)-hexyloxy]-piperidine-1-carboxylic acid 2,2,2-trichloro-1,1-dimethyl-ethyl ester, 4-[6-(allyl-methyl-amino)-hexyloxy]-piperidine-1-carboxylic acid 4-nitro-phenyl ester, 4-[6-(Allyl-methyl-amino)-hexyloxy]-piperidine-1-carboxylic acid isobutyl ester, 4-[6-(Allyl-methyl-amino)-hexyloxy]-piperidine-1-carboxylic acid benzyl ester, 4-[6-(Allyl-methyl-amino)-hexyloxy]-piperidine-1-carboxylic acid allyl ester, 4-[6-(Allyl-methyl-amino)-hexyloxy]-piperidine-1-carboxylic acid phenyl ester, 4-[6-(Allyl-methyl-amino)-hexyloxy]-piperidine-1-carboxylic acid butyl ester, 4-[6-(Allyl-methyl-amino)-hexyloxy]-piperidine-1-carboxylic acid 4-methoxycarbonyl-phenyl ester, 4-[6-(Allyl-methyl-amino)-hexyloxy]-piperidine-1-carboxylic acid 4-fluoro-phenylester, 4-[6-(Allyl-methyl-amino)-hexyloxy]-piperidine-1-carboxylic acid 4-bromo-phenyl ester, 4-[6-(Allyl-methyl-amino)-hexyloxy]-piperidine-1-carboxylic acid 4-chloro-phenyl ester, 4-[6-(Allyl-methyl-amino)-hexyloxy]-piperidine-1-carboxylic acid p-tolyl ester, 4-[6-(Allyl-methyl-amino)-hexyloxy]-piperidine-1-carboxylic acid 4-trifluoromethyl-phenyl ester, 4-[6-(Allyl-methyl-amino) hexyloxy]-piperidine-1-sulfonic acid benzylamide, 4-[6-(Allyl-methyl-amino)-hexyloxy]-piperidine-1-sulfonic acid butylamide, 4-[6-(Allyl-methyl-amino)-hexyloxy]-piperidine-1-sulfonic acid phenethyl-amide, 4-[6-(Allyl-methyl-amino)-hexyloxy]-piperidine-1-sulfonic acid (furan-2-ylmethyl)-amide, {4-[6-(Allyl-methyl-amino)-hexyloxy]-piperidine-1-sulfonylamino}-acetic acid ethyl ester, 4-[6-(Allyl-methyl-amino)-hexyloxy]-piperidine-1-sulfonic acid cyclohexylmethyl-amide, 4-[6-(Allyl-methyl-amino)-hexyloxy]-piperidine-1-sulfonic acid cyclopropylamide, 4-[6-(Allyl-methyl-amino)-hexyloxy]-piperidine-1-sulfonic acid (2,2,2-trifluoro-ethyl)-amide, 4-[6-(Allyl-methyl-amino)-hexyloxy]-piperidine-1-sulfonic acid (benzo[1,3]dioxol-5-ylmethyl)-amide, 4-[6-(Allyl-methyl-amino)-hexyloxy]-piperidine-1-sulfonic acid 4-fluoro-benzylamide, 4-[6-(Cyclopropyl-methyl-amino)-hexyloxy]-piperidine-1-sulfonic acid (4-chloro-phenyl)-amide, 4-[6-(Allyl-methyl-amino)-hexyloxy]-piperidine-1-sulfonic acid (4-chloro-phenyl)-amide, 4-[6-(Cyclopropyl-methyl-amino)-hexyloxy]-piperidine-1-sulfonic acid (4-fluoro-phenyl)-amide, 4-[6-(Allyl-methyl-amino)-hexyloxy]-piperidine-1-sulfonic acid (4-fluoro-phenyl)-amide, 4-[6-(Cyclopropyl-methyl-amino)-hexyloxy]-piperidine-1-sulfonic acid (4-bromo-phenyl)-amide, 4-[6-(Allyl-methyl-amino)-hexyloxy]-piperidine-1-sulfonic acid (4-bromo-phenyl)-amide, 4-[6-(Cyclopropyl-methyl-amino)-hexyloxy]-piperidine-1-sulfonic acid (p-tolyl)-amide, 4-[6-(Allyl-methyl-amino)-hexyloxy]-piperidine-1-sulfonic acid (p-tolyl)-amide, 4-[6-(Cyclopropyl-methyl-amino)-hexyloxy]-piperidine-1-sulfonic acid (3,4-difluoro-phenyl)-amide,
4-[6-(Allyl-methyl-amino)-hexyloxy]-piperidine-1-sulfonic acid (3,4-difluoro-phenyl)-amide,
4-[6-(Cyclopropyl-methyl-amino)-hexyloxy]-piperidine-1-sulfonic acid (4-trifluoromethyl-phenyl)-amide,
4-[6-(Allyl-methyl-amino)-hexyloxy]-piperidine-1-sulfonic acid (4-trifluoromethyl-phenyl)-amide,
4-[6-(Cyclopropyl-methyl-amino)-hexyloxy]-piperidine-1-sulfonic acid (3-fluoro-phenyl)-amide,
4-[6-(Allyl-methyl-amino)-hexyloxy]-piperidine-1-sulfonic acid (3-fluoro-phenyl)-amide,
4-[6-(Cyclopropyl-methyl-amino)-hexyloxy]-piperidine-1-sulfonic acid (4-cyano-phenyl)-amide,
4-[6-(Allyl-methyl-amino)-hexyloxy]-piperidine-1-sulfonic acid (4-cyano-phenyl)-amide,
4-[6-(Cyclopropyl-methyl-amino)-hexyloxy]-piperidine-1-sulfonic acid (2,4-difluoro-phenyl)-amide,
4-[6-(Allyl-methyl-amino)-hexyloxy]-piperidine-1-sulfonic acid (2,4-difluoro-phenyl)-amide,
4-[6-(Cyclopropyl-methyl-amino)-hexyloxy]-piperidine-1-sulfonic acid (4-methoxy-phenyl)-amide,
4-[6-(Allyl-methyl-amino)-hexyloxy]-piperidine-1-sulfonic acid (4-methoxy-phenyl)-amide,
4-[6-(Cyclopropyl-methyl-amino)-hexyloxy]-piperidine-1-sulfonic acid (2,5-difluoro-phenyl)-amide,
4-[6-(Allyl-methyl-amino)-hexyloxy]-piperidine-1-sulfonic acid (2,5-difluoro-phenyl)-amide,
4-[6-(Cyclopropyl-methyl-amino)-hexyloxy]-piperidine-1-sulfonic acid (phenyl)-amide,
4-[6-(Allyl-methyl-amino)-hexyloxy]-piperidine-1-sulfonic acid (phenyl)-amide,
4-(6-Azepan-1-yl-hexyloxy)-piperidine-1-sulfonic acid phenylamide,
4-{6-[(2-Methoxy-ethyl)-methyl-amino]-hexyloxy}-piperidine-1-sulfonic acid phenylamide,
4-[6-(Ethyl-methyl-amino)-hexyloxy]-piperidine-1-sulfonic acid phenylamide,
4-[6-(2-Methyl-piperidin-1-yl)-hexyloxy]-piperidine-1-sulfonic acid phenylamide,
4-{6-[(2-Hydroxy-ethyl)-methyl-amino]-hexyloxy}-piperidine-1-sulfonic acid phenylamide,
{Methyl-[6-(1-phenylsulfamoyl-piperidin-4-yloxy)-hexyl]-amino}-acetic acid ethyl ester,
4-[6-(Butyl-methyl-amino)-hexyloxy]-piperidine-1-sulfonic acid phenylamide,
4-(6-Diallylamino-hexyloxy)-piperidine-1-sulfonic acid phenylamide,
4-(6-Pyrrolidin-1-yl-hexyloxy)-piperidine-1-sulfonic acid phenylamide,
4-[6-(Methyl-prop-2-ynyl-amino)-hexyloxy]-piperidine-1-sulfonic acid phenylamide,
4-(6-Piperidin-1-yl-hexyloxy)-piperidine-1-sulfonic acid phenylamide,
4-[6-(Ethyl-isopropyl-amino)-hexyloxy]-piperidine-1-sulfonic acid phenylamide,
4-(6-Morpholin-4-yl-hexyloxy)-piperidine-1-sulfonic acid phenylamide,
4-[6-(Isopropyl-methyl-amino)-hexyloxy]-piperidine-1-sulfonic acid phenylamide,
4-[6-(3,6-Dihydro-2H-pyridin-1-yl)-hexyloxy]-piperidine-1-sulfonic acid phenylamide,
4-{6-[Ethyl-(2-hydroxy-ethyl)-amino]-hexyloxy}-piperidine-1-sulfonic acid phenylamide,
4-(6-Dimethylamino-hexyloxy)-piperidine-1-sulfonic acid phenylamide,
4-[6-(Methyl-propyl-amino)-hexyloxy]-piperidine-1-sulfonic acid phenylamide,
4-(6-Diethylamino-hexyloxy)-piperidine-1-sulfonic acid phenylamide,
4-(6-Thiomorpholin-4-yl-hexyloxy)-piperidine-1-sulfonic acid phenylamide,
4-[6-(Butyl-ethyl-amino)-hexyloxy]-piperidine-1-sulfonic acid phenylamide,
4-(6-Thiazolidin-3-yl-hexyloxy)-piperidine-1-sulfonic acid phenylamide,
4-[6-(4-Hydroxy-piperidin-1-yl)-hexyloxy]-piperidine-1-sulfonic acid phenylamide,
4-[6-(4-Methyl-piperazin-1-yl)-hexyloxy]-piperidine-1-sulfonic acid phenylamide,
4-[6-(4-Hydroxymethyl-piperidin-1-yl)-hexyloxy]-piperidine-1-sulfonic acid phenylamide,
4-[6-(Cyclopropylmethyl-propyl-amino)-hexyloxy]-piperidine-1-sulfonic acid phenylamide,
4-[6-(3-Hydroxy-piperidin-1-yl)-hexyloxy]-piperidine-1-sulfonic acid phenylamide,
4-[6-(Cyclohexyl-methyl-amino)-hexyloxy]-piperidine-1-sulfonic acid phenylamide,
4-[6-(3-Dimethylamino-pyrrolidin-1-yl)-hexyloxy]-piperidine-1-sulfonic acid phenylamide,
4-(6-Azetidin-1-yl-hexyloxy)-piperidine-1-sulfonic acid phenylamide, and
4-[6-(Cyclopropylmethyl-methyl-amino)-hexyloxy]-piperidine-1-sulfonic acid phenylamide,
and pharmaceutically acceptable salts thereof.

Other preferred compounds of general formula (I) are those selected from the group consisting of
4-[3-(Allyl-methyl-amino)-prop-1-ynyl]-piperidine-1-carboxylic acid 4-chloro-phenyl ester,
4-[3-(Methyl-propyl-amino)-prop-1-ynyl]-piperidine-1-carboxylic acid 4-chloro-phenyl ester,
4-{3-[Ethyl-(2-hydroxy-ethyl)-amino]-prop-1-ynyl}-piperidine-1-carboxylic acid 4-chloro-phenyl ester,
Allyl-methyl-{3-[1-(4-trifluoromethyl-benzenesulfonyl)-piperidin-4-yl]-prop-2-ynyl}-amine,
Methyl-propyl-{3-[1-(4-trifluoromethyl-benzenesulfonyl)-piperidin-4-yl]-prop-2-ynyl}-amine,
2-(Ethyl-{3-[1-(4-trifluoromethyl-benzenesulfonyl)-piperidin-4-yl]-prop-2-ynyl}-amino)-ethanol,
Allyl-methyl-{5-[1-(4-trifluoromethyl-benzenesulfonyl)-piperidin-4-yl]-pent-4-ynyl}-amine,
Methyl-propyl-{5-[1-(4-trifluoromethyl-benzenesulfonyl)-piperidin-4-yl]-pent-4-ynyl}-amine,
4-{3-[Ethyl-(2-hydroxy-ethyl)-amino]-propyl}-piperidine-1-carboxylic acid 4-chloro-phenyl ester,
2-(Ethyl-{5-[1-(4-trifluoromethyl-benzenesulfonyl)-piperidin-4-yl]-pent-4-ynyl}-amino)-ethanol,
4-{5-[Ethyl-(2-hydroxy-ethyl)-amino]-pent-1-ynyl}-piperidine-1-carboxylic acid 4-chloro-phenyl ester,
4-[5-(Methyl-propyl-amino)-pent-1-ynyl]-piperidine-1-carboxylic acid 4-chloro-phenyl ester,
4-[5-(Allyl-methyl-amino)-pent-1-ynyl]-piperidine-1-carboxylic acid 4-chloro-phenyl ester,
2-(Ethyl-{3-[1-(4-trifluoromethyl-benzenesulfonyl)-piperidin-4-yl]-propyl}-amino)-ethanol,
Methyl-propyl-{3-[1-(4-trifluoromethyl-benzenesulfonyl)-piperidin-4-yl]-propyl}-amine,
4-{5-[Ethyl-(2-hydroxy-ethyl)-amino]-pentyl}-piperidine-1-carboxylic acid 4-chloro-phenyl ester,
4-[3-(Methyl-propyl-amino)-propyl]-piperidine-1-carboxylic acid 4-chloro-phenyl ester,
4-[5-(Methyl-propyl-amino)-pentyl]-piperidine-1-carboxylic acid 4-chloro-phenyl ester,
(4-Chloro-phenyl)-{4-[3-(methyl-propyl-amino)-prop-1-ynyl]-piperidin-1-yl}-methanone, {4-[3-(Allyl-methyl-amino)-prop-1-ynyl]-piperidin-1-yl}-(4-chloro-phenyl)-methanone, (4-Chloro-phenyl)-(4-{3-[ethyl-(2-hydroxy-ethyl)-amino]-prop-1-ynyl}-piperidin-1-yl)-methanone, Allyl-methyl-{4-[1-(4-trifluoromethyl-benzenesulfonyl)-piperidin-4-yl]-but-3-ynyl}-amine, Methyl-propyl-{4-[1-(4-trifluoromethyl-benzenesulfonyl)-piperidin-4-yl]-but-3-ynyl}-amine, 2-(Ethyl-{4-[1-(4-trifluoromethyl-benzenesulfonyl)-piperidin-4-yl]-but-3-ynyl}-amino)-ethanol, 4-[4-(Allyl-methyl-amino)-but-1-ynyl]-piperidine-1-carboxylic acid 4-chloro-phenyl ester, 4-[4-(Methyl-propyl-amino)-but-1-ynyl]-piperidine-1-carboxylic acid 4-chloro-phenyl ester, 4-{4-[Ethyl-(2-hydroxy-ethyl)-amino]-but-1-ynyl}-piperidine-1-carboxylic acid 4-chloro-phenyl ester, Ethyl-(2-methoxy-ethyl)-{4-[1-(4-trifluoromethyl-benzenesulfonyl)-piperidin-4-yl]-but-3-ynyl}-amine, 4-{4-[Ethyl-(2-methoxy-ethyl)-amino]-but-1-ynyl}-piperidine-1-carboxylic acid 4-chloro-phenyl ester, {4-[4-(Allyl-methyl-amino)-but-1-ynyl]-piperidin-1-yl}-(4-chloro-phenyl)-methanone, 2-(Ethyl-{4-[1-(4-trifluoromethyl-benzenesulfonyl)-piperidin-4-yl]-butyl}-amino)-ethanol, (4-Chloro-phenyl)-{4-[4-(methyl-propyl-amino)-but-1-ynyl]-piperidin-1-yl}-methanone, (4-Chloro-phenyl)-(4-{4-[ethyl-(2-hydroxy-ethyl)-amino]-but-1-ynyl}-piperidin-1-yl)-methanone, Methyl-propyl-{4-[1-(4-trifluoromethyl-benzenesulfonyl)-piperidin-4-yl]-butyl}-amine, (4-Chloro-phenyl)-(4-{4-[ethyl-(2-methoxy-ethyl)-amino]-but-1-ynyl}-piperidin-1-yl)-methanone, and (4-Chloro-phenyl)-{4-[5-(methyl-propyl-amino)-pent-1-ynyl]-piperidin-1-yl}-methanone, and pharmaceutically acceptable salts thereof.

Particularly preferred compounds of general formula (I) are those selected from the group consisting of Allyl-{4-[1-(4-chloro-benzenesulfonyl)-piperidin-4-yloxy]-butyl}-methyl-amine, Allyl-{3-[1-(4-bromo-benzenesulfonyl)-piperidin-4-yloxy]-propyl}-methyl-amine, 4-[6-(Allyl-methyl-amino)-hexyloxy]-piperidine-1-carboxylic acid isobutyl ester, {4-[4-(Allyl-methyl-amino)-butoxy]-piperidin-1-yl}-(4-chloro-phenyl)-methanone, 1-(4-{2-[4-(Allyl-methyl-amino)-butoxy]-ethyl}-piperidin-1-yl)-2-(4-chloro-phenyl)-ethanone, (4-{2-[4-(Allyl-methyl-amino)-butoxy]-ethyl}-piperidin-1-yl)-(4-chloro-phenyl)-methanone, (4-{2-[2-(Allyl-methyl-amino)-ethoxy]-ethyl}-piperidin-1-yl)-(4-chloro-phenyl)-methanone, {4-[4-(Allyl-methyl-amino)-butoxymethyl]-piperidin-1-yl}-(4-chloro-phenyl)-methanone, {4-[3-(Allyl-methyl-amino)-propoxymethyl]-piperidin-1-yl}-(4-chloro-phenyl)-methanone, 4-{3-[Ethyl-(2-hydroxy-ethyl)-amino]-propoxymethyl}-piperidine-1-carboxylic acid 4-chloro-phenyl ester, 4-[4-(Allyl-methyl-amino)-butoxymethyl]-piperidine-1-carboxylic acid 4-chloro-phenyl ester, 4-[6-(Allyl-methyl-amino)-hexyloxy]-piperidine-1-sulfonic acid butylamide, 4-[6-(Allyl-methyl-amino)-hexyloxy]-piperidine-1-sulfonic acid cyclohexylmethyl-amide, 4-[6-(Allyl-methyl-amino)-hexyloxy]-piperidine-1-sulfonic acid (4-chloro-phenyl)-amide, 4-[6-(Allyl-methyl-amino)-hexyloxy]-piperidine-1-sulfonic acid (4-bromo-phenyl)-amide, 4-[6-(Cyclopropyl-methyl-amino)-hexyloxy]-piperidine-1-sulfonic acid (3,4-difluoro-phenyl)-amide, 4-[6-(Allyl-methyl-amino)-hexyloxy]-piperidine-1-sulfonic acid (4-trifluoromethyl-phenyl)-amide, 4-[6-(Allyl-methyl-amino)-hexyloxy]-piperidine-1-sulfonic acid (2,5-difluoro-phenyl)-amide, and 4-[6-(Allyl-methyl-amino)-hexyloxy]-piperidine-1-sulfonic acid (phenyl)-amide, and pharmaceutically acceptable salts thereof.

Other particularly preferred compounds of general formula (I) are those selected from the group consisting of 2-(Ethyl-{5-[1-(4-trifluoromethyl-benzenesulfonyl)-piperidin-4-yl]-pent-4-ynyl}-amino)-ethanol, 2-(Ethyl-{4-[1-(4-trifluoromethyl-benzenesulfonyl)-piperidin-4-yl]-but-3-ynyl}-amino)-ethanol, (4-Chloro-phenyl)-{4-[4-(methyl-propyl-amino)-but-1-ynyl]-piperidin-1-yl}-methanone, Ethyl-(2-methoxy-ethyl)-{4-[1-(4-trifluoromethyl-benzenesulfonyl)-piperidin-4-yl]-but-3-ynyl}-amine, Methyl-propyl-{4-[1-(4-trifluoromethyl-benzenesulfonyl)-piperidin-4-yl]-butyl}-amine, and Methyl-propyl-{3-[1-(4-trifluoromethyl-benzenesulfonyl)-piperidin-4-yl]-prop-2-ynyl}-amine, and pharmaceutically acceptable salts thereof.

Compounds of formula (I) can have one or more asymmetric carbon atoms and can exist in the form of optically pure enantiomers or as racemats. The invention embraces all of these forms.

It will be appreciated, that the compounds of general formula (I) in this invention may be derivatised at functional groups to provide derivatives which are capable of conversion back to the parent compound in vivo.

The present invention also relates to a process for the manufacture of compounds as described above, which process comprises reacting a compound of formula (II)

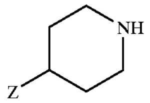

(II)

whereinZis$(A^1,A^2)N—C(A^3,A^4)—(CH_2)_m—V—(CH_2)_n—$, $X—CH_2—(CH_2)_m—V—(CH_2)_n—$, $HO(CH_2)_n—$, or $HOOC(CH_2)_n—$, wherein X is chlorine, bromine, iodine, methanesulfonyl, or toluenesulfonyl, and $A^1$, $A^2$, $A^3$, $A^4$, V, m and n are as defined above, with $ClSO_2—A^5$, $ClCOO—A^5$, $ClCSO—A^5$, $OCN—A^5$, $SCN—A^5$, $HOOC—A^5$, or $ClSO_2NR^1—A^5$, wherein $A^5$ is as defined above.

The invention further relates to compounds of formula (I) as defined above, when manufactured according to a process as defined above.

As described above, the compounds of formula (I) of the present invention can be used for the treatment and/or prophylaxis of diseases which are associated with OSC such as hypercholesterolemia, hyperlipemia, arteriosclerosis, vascular diseases, mycoses, parasite infections and gallstones, and/or treatment and/or prophylaxis of impaired glucose tolerance, diabetes, tumors and/or hyperproliferative disorders, preferably for the treatment and/or prophylaxis of hypercholesterolemia and/or hyperlipemia. Hyperproliferative skin and vascular disorders particularly come into consideration as hyperproliferative disorders.

The invention therefore also relates to pharmaceutical compositions comprising a compound as defined above and a pharmaceutically acceptable carrier and/or adjuvant.

Further, the invention relates to compounds as defined above for use as therapeutic active substances, particularly as therapeutic active substances for the treatment and/or prophylaxis of of diseases which are associated with OSC such as hypercholesterolemia, hyperlipemia, arteriosclerosis, vascular diseases, mycoses, parasite infections, gallstones, tumors and/or hyperproliferative disorders, and/or treatment and/or prophylaxis of impaired glucose tolerance and diabetes, preferably for the treatment and/or prophylaxis of hypercholesterolemia and/or hyperlipemia.

In another embodiment, the invention relates to a method for the treatment and/or prophylaxis of diseases which are associated with OSC such as hypercholesterolemia, hyperlipemia, arteriosclerosis, vascular diseases, mycoses, parasite infections, gallstones, tumors and/or hyperproliferative disorders, and/or treatment and/or prophylaxis of impaired glucose tolerance and diabetes, preferably for the treatment and/or prophylaxis of hypercholesterolemia and/or hyperlipemia, which method comprises administering a compound as defined above to a human being or animal.

The invention further relates to the use of compounds as defined above for the treatment and/or prophylaxis of diseases which are associated with OSC such as hypercholesterolemia, hyperlipemia, arteriosclerosis, vascular diseases, mycoses, parasite infections, gallstones, tumors and/or hyperproliferative disorders, and/or treatment and/or prophylaxis of impaired glucose tolerance and diabetes, preferably for the treatment and/or prophylaxis of hypercholesterolemia and/or hyperlipemia.

In addition, the invention relates to the use of compounds as defined above for the preparation of medicaments for the treatment and/or prophylaxis of diseases which are associated with OSC such as hypercholesterolemia, hyperlipemia, arteriosclerosis, vascular diseases, mycoses, parasite infections, gallstones, tumors and/or hyperproliferative disorders, and/or treatment and/or prophylaxis of impaired glucose tolerance and diabetes, preferably for the treatment and/or prophylaxis of hypercholesterolemia and/or hyperlipemia. Such medicaments comprise a compound as defined above.

The compounds of formula (I) can be manufactured by the methods given below, by the methods given in the examples or by analogous methods. Appropriate reaction conditions for the individual reaction steps are known to the person skilled in the art. Starting materials are either commercially available or can be prepared by methods analogous to the methods given in the examples or by methods known in the art.

Scheme 1

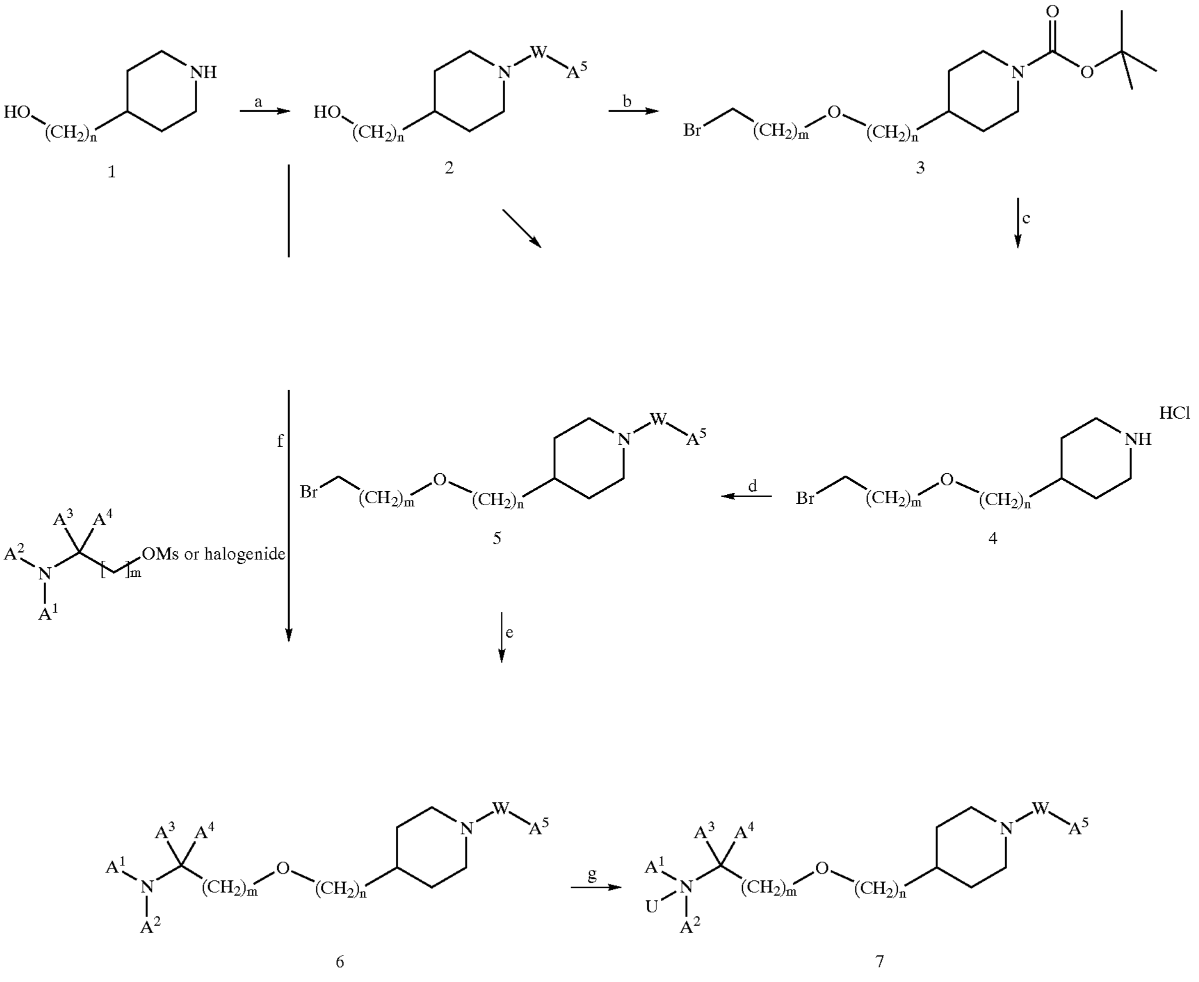

Scheme 2

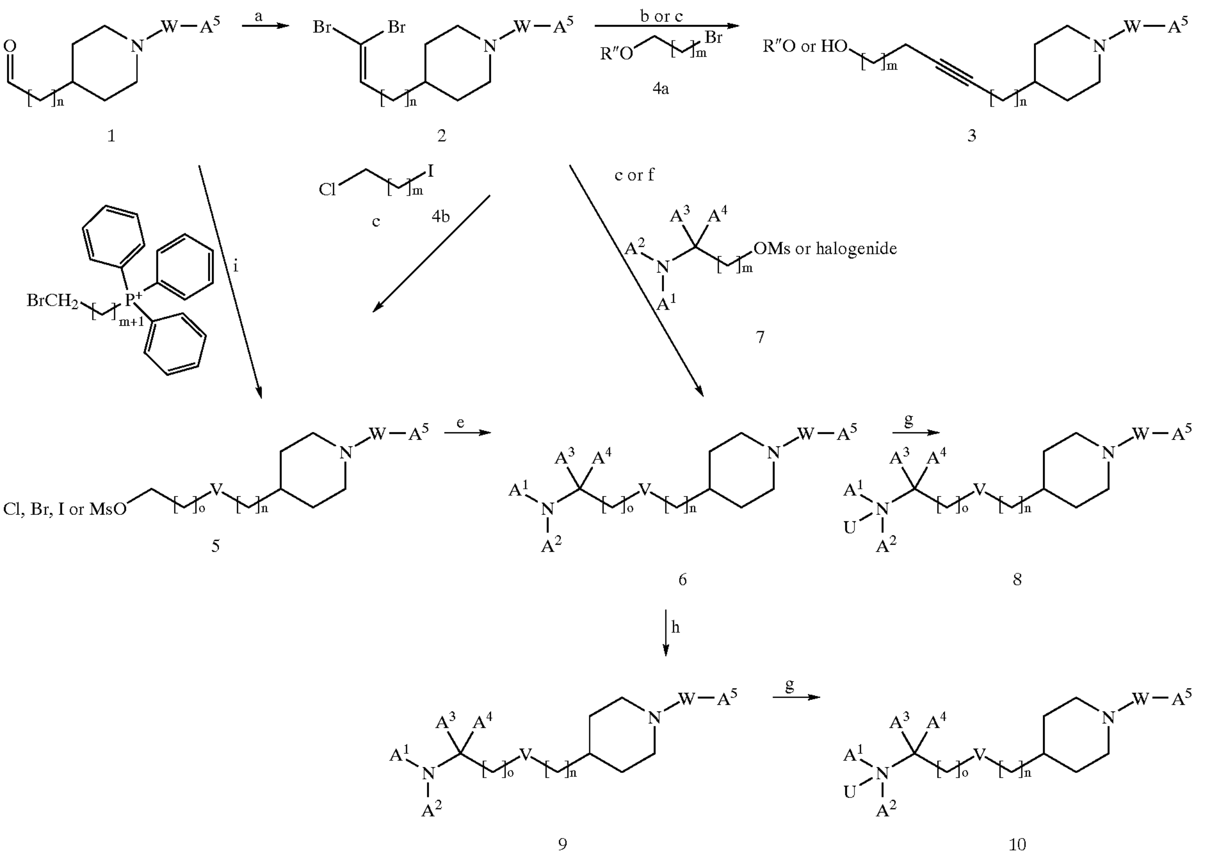

$R^2$ = protecting group
for V = $CH_2$, o = m or m+1 (if e.g. CH = CH or alkyne is hydrogenated to $CH_2CH_2$)
for V = CH = CH or alkyne, o = m Scheme 1

In Scheme 1, an overview of the synthesis of the compounds of the present invention is shown. Hydroxypiperidine 1 or hydroxyalkylpiperidine 1 is e.g. N-BOC-protected (step a) in $CH_2Cl_2$ with di-tert-butyl dicarbonate at RT or reacted with an activated $WA^5$ (see below). O-Alkylation of piperidiene derivative 2 (step b) in DMF with NaH as base and dihaloalkane (halogene is here represented by bromine, but can be also, Cl, I, mesylate or tosylate) at 0° C. to RT yields halogenide 3 or 5. For shorter alkanes ($C_2$- and $C_3$-alkanes) the method of choice is the in situ generation of the haloalkane-triflate (from the corresponding haloalkanol with trifluoromethansulfonic anhydride/2,6-di-tert-butylpyridine in $CH_2Cl_2$ at 0° C.). This haloalkane-triflate is then reacted with alcohol 2 with 2,6-di-tert-butylpyridine as base in nitromethane at 60° C. to yield bromide 3 or 5 [following a procedure of Belostotskii, Anatoly M.; Hassner, Alfred. Synthetic methods. 41. Etherification of hydroxysteroids via triflates. Tetrahedron Lett. (1994), 35(28), 5075–6].

Boc deprotection for 2 ($WA^5$=BOC) (step c) e.g. in $CH_2Cl_2$ at RT with 4N HCl in dioxane yields hydrochloride 4. This building block is then further transformed to intermediate 5 by one of the following procedures:

Sulfonylation of compound 4 is done in dioxane with Hünigsbase and a sulfonyl chloride over night at RT to yield the sulfonamide 5.

Compound 4 may be reacted with $A^5OCOCl$/Huenigsbase in dioxane or $CH_2Cl_2$ or by reaction of $A^5OH/Cl_3COCl$/quinoline (formation of the chloroformate) followed by reaction with compound 4 and Huenigsbase to yield the corresponding carbamate.

Compound 4 may be reacted with $A^5OCSCl$ in dioxane to yield the corresponding thiocarbamate.

Compound 4 may be reacted with an isocyanate in dioxane at room temperature to yield the corresponding urea.

Compound 4 may be reacted with an isothiocyanate in dioxane at room temperature to yield the corresponding thiourea.

Compound 4 may be reacted with $A^5COCl$/Huenigsbase in $CH_2Cl_2$, or with $A^5COOH$/EDCI/DMAP (anhydride formation and subsequent addition of the amine, −10° C. to room temperature) or as alternative with $A^5COOH$/EDCI/DMAP or $A^5COOH$/Huenigsbase/EDCI/HOBT in DMF, dioxane or $CH_2Cl_2$ at room temperature to yield the corresponding amide.

Compound 4 may be reacted with a sulfamoyl chloride in dioxane in the presence of an excess of triethylamine to yield the corresponding sulfamide 5. The sulfamoyl chlorides were synthesized from $A^5NH_2$ and chlorosulfonic acid in $CH_2Cl_2$ at 0° C. to room temperature followed by reaction with $PCl_5$ in toluene at 75° C. Alternatively the sulfamoyl chlorides can be synthesized in acetonitrile with $A^5NH_2$ and sulfuryl chloride at 0° C. to 65° C.

These compounds 5 are then converted (step e) to the amine 6 in DMA at RT or MeOH at RT to 50–70° C. with an excess of the corresponding amine $A^1A^2NH$ or in acetone with $K_2CO_3$ at 65° C.

Finally, the substitution pattern for $A^5$ can be manipulated: e.g. hydrolysis of an N-acetyl group to an $NH_2$.

Alternatively, the mesylate or halogenide 8 of the group $A^1A^2NC(A^3A^4)$—$(CH_2)$— can be synthesized by known methods and attached to building block 2 (NaH in DMF), to yield directly amine 6 (step f). If $WA^5$ is a protecting group, deprotection as described before, followed by the reaction with an activated $WA^5$ (see above) and reaction with 8 gives the desired amine 6 (step f).

The amines 6 can optionally be converted to a salt or to the N-oxide 7 (compound 6 was reacted with a mixture of hydrogen peroxid urea adduct and phthalic anhydride in $CH_2Cl_2$ at RT, step g).

Scheme 2

In scheme 2 the synthesis of compounds of the general formula (I) in which V is —$CH_2$—, —CH═CH— or —C≡C— is described. The synthesis starts from aldehyde 1 which can be derived from a suitable protected 4-piperidinecarboxylic acid (such as BOC-4-piperidinecarboxylic acid or $WA^5$-4-piperidinecarboxylic acid, via Weinreb-amid and LAH reduction) or from the corresponding alcohol by Swern oxidation. Side chain extension is effected through application of the Corey-Fuchs method. The aldehyde 1 is treated with triphenylphosphine, tetra-bromo-methane and triethylamine in $CH_2Cl_2$ at 0° C. to RT to yield 2,2-Dibromo-vinyl derivative 2 (step a). Rearrangement with n-BuLi (ca 1.6 M in hexane) in THF at −78° C., followed by reaction with formaldehyde (−78° C. to RT; step b) leads to the propargyl alcohol 3 [step b, following conditions described in: Marshall, James A.; Bartley, Gary S.; Wallace, Eli M. Total Synthesis of the Pseudopterane (−)-Kallolide B, the Enantiomer of Natural (+)-Kallolide B. J. Org. Chem. (1996), 61(17), 5729–5735; and Baker, Raymond; Boyes, Alastair L.; Swain, Christopher J. Synthesis of talaromycins A, B, C, and E., J. Chem. Soc., Perkin Trans. 1 (1990), (5), 1415–21.].

For longer side chains, the rearrangement of dibromoalkene 2 is performed with n-BuLi (ca 1.6 M in hexane) in THF at −78° C. as above, followed by addition of a cosolvens such as DMPU and reaction with O-protected 1-bromo-alcohols 4a (e.g. 1-bromo-n-tetrahydro-pyranyloxyalkane) to yield the O-protected compounds 3 which can be deprotected to the corresponding alkinol 3 derivative (in MeOH at 50–60° C. in the presence of catalytic amount of pyridinium toluene-4-sulfonate; step c).

Mesylation of the alcohol 3 with methanesulfonylchloride, pyridine and DMAP in $CH_2Cl_2$ at 0° C. to RT yields mesylate 5 (step d) which can be converted to the amine 6 in DMA at RT or MeOH at RT or at 50–70° C. with an excess of the corresponding amine $NHA^1A^2$ (step e). Alternatively, side chain elongation of dibromoalkene 2 can also be performed with chloroalkaneiodide 4b (m>1) applying Corey-Fuchs methodology described above to give directly chloride 5. Chloride 5 is then converted via iodide 5 (Finkelstein reaction) to the amine 6 as described later.

If $A^5W$ is a protecting moiety this can be cleaved prior to salt or n-oxide formation using TFA in $CH_2Cl_2$ for BOC-groups or by hydrogenation in methanol with Pd/C for Z-groups. The resulting amine (not shown) may be treated according to one of the procedures described for scheme 1 to yield a derivative 9 with a desired $A^5W$ group (step h).

Optionally, the introduction of the desired $A^5W$ moiety can be performed at an earlier stage, e.g. at the derivative 2, O-protected derivative 3 or compound 5 to enable an optimization of the $NA^1A^2$ terminus at the final step e.

Alternatively the side chain can be directly introduced on aldehyde 1 via Wittig-reaction to give bromide 5 (step i; aldehyde 1 and Wittigsalt 11 was refluxed in the presence of $K_2CO_3$ or $Cs_2CO_3$ in 2-methyl-2-butanol). Bromide 5 can directly be transformed to amine 6 or N-oxide 8 as described above. For the cases $A^5W$ is a protecting group (BOC or Z), this can be cleaved (i.e. first selective hydrogenation of the double bond with Pt/C, $H_2$ in toluene followed by cleavage of the Z-protection with HBr (33%) in acetic acid or also double bond and protective group at the same time). The desired $A^5W$ moiety is then introduced using the methods shown in scheme 1.

To obtain compounds 6 in which $A^3$ and/or $A^4$ is not H and m>0, compounds 2 can be reacted with compounds 7 under the same condition as described for step c. The building blocks 7 can be prepared by known methods. For the introduction of the group $(A^1,A^2)N—C(A^3,A^4)$— wherein $A^3$ and/or $A^4$ is not H and m=0, a two step procedure has to be followed: first the rearrangement with n-BuLi (ca 1.6 M in hexane) in THF at −78° C., followed by reaction with the corresponding aldehyde ($A^3$ or $A^4$—C═OH) or ketone ($A^3COA^4$, at −78° C. to RT) leading to the $A^3$,$A^4$ substituted propargyl alcohol which can be transformed to a phosphorester or a chloride (not shown) and reacted with the desired ($A^1$,$A^2$)-amine in the presence of Tetrakis(triphenylphosphine)palladium (for the phosphorsester) or Cu(I)Cl/Cu bronze and Huenig's base for the chloride to yield the desired $A^3$,$A^4$-substituted compound 6 (step f). (see: Bartlett, Paul A.; McQuaid, Loretta A. Total synthesis of □-methyl shikimate and □-3-phosphoshikimic acid. J. Am. Chem. Soc. (1984), 106(25), 7854–60 and Cooper, Matthew A.; Lucas, Mathew A.; Taylor, Joanne M.; Ward, A. David; Williamson, Natalie M. A convenient method for the aromatic amino-Claisen rearrangement of N-(1,1-disubstituted-allyl)anilines. Synthesis (2001), (4), 621–625.)

Compounds in which V is —$CH_2$— or —CH═CH— can be obtained by hydrogenation of compound 6 with Pt/C (yields the saturated analogue 9) or by hydrogenation with other known methods (yields the double bond analogue 9). Alternatively, the alkyne group can already manipulated on compound 3 (e.g. LAH-reduction for m=0, gives V=trans-CH═CH— or hydrogenation with Pt/C or $PtO_2.H_2O$ yields V=$CH_2CH_2$—), and then further be transformed to the final compounds 9 and/or 10.

Finally, the substitution pattern for $A^5$ can be manipulated: e.g. hydrolysis of an acetyl group to an $NH_2$.

The amines 6 and 9 can be converted to a salt or as described in step f to the N-oxide 8 and 10, respectively, using a mixture of hydrogen peroxide urea adduct and phthalic anhydride in $CH_2Cl_2$ at RT.

The following tests were carried out in order to determine the activity of the compounds of formula I and their salts.

Inhibition of Human Liver Microsomal 2,3-oxidosqualene-lanosterol Cyclase (OSC)

Liver microsomes from a healthy volunteer were prepared in sodium phosphate buffer (pH 7.4). The OSC activity was measured in the same buffer, which also contained 1 mM EDTA and 1 mM dithiothreitol. The microsomes were diluted to 0.8 mg/ml protein in cold phosphate buffer. Dry [$^{14}$C]R,S-monooxidosqualene (MOS, 12.8 mCi/mmol) was diluted to 20 nCi/μl with ethanol and mixed with phosphate buffer-1% BSA (bovine serum albumin). A stock solution of 1 mM test substance in DMSO was diluted to the desired concentration with phosphate buffer-1% BSA. 40 μl of microsomes were mixed with 20 μl of the solution of the test substance and the reaction was subsequently started with 20 μl of the [$^{14}C$]R,S-MOS solution. The final conditions were: 0.4 mg/ml of microsomal proteins and 30 μl of [$^{14}C$]R,S-MOS in phosphate buffer, pH 7.4, containing 0.5% albumin, DMSO <0.1% and ethanol <2%, in a total volume of 80 μl.

After 1 hour at 37° C. the reaction was stopped by the addition of 0.6 ml of 10% KOH-methanol, 0.7 ml of water and 0.1 ml of hexane:ether (1:1, v/v) which contained 25 μg of non-radioactive MOS and 25 μg of lanosterol as carriers. After shaking, 1 ml of hexane:ether (1:1, v/v) was added to each test tube, these were again shaken and then centrifuged. The upper phase was transferred into a glass test tube, the lower phase was again extracted with hexane:ether and combined with the first extract. The entire extract was evaporated to dryness with nitrogen, the residue was suspended in 50 μl of hexane:ether and applied to a silica gel plate. Chromatographic separation was effected in hexane:ether (1:1, v/v) as the eluent. The Rf values for the MOS substrate and the lanosterol product were 0.91 and, respectively, 0.54. After drying, radioactive MOS and lanosterol were observed on the silica gel plate. The ratio of MOS to lanosterol was determined from the radioactive bands in order to determine the yield of the reaction and OSC inhibition.

The test was carried out on the one hand with a constant test substance concentration of 100 nM and the percentage OSC inhibition against controls was calculated. The more preferred compounds of the present invention exhibit inhibitions larger than 50%. In addition, the test was carried out with different test substance concentrations and subsequently the $IC_{50}$ value was calculated, i.e. the concentration required to reduce the conversion of MOS into lanosterol to 50% of the control value. The preferred compounds of the present invention exhibit $IC_{50}$ values of 1 nM to 10 μM, preferrably of 1–100 nM.

The compounds of formula I and their pharmaceutically acceptable acid addition salts can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils.

The production of the pharmaceutical preparations can be effected in a manner which will be familiar to any person skilled in the art by bringing the described compounds of formula I and their pharmaceutically acceptable acid addition salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers are, however, required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 mg to about 1000 mg, especially about 50 mg to about 500 mg, comes into consideration for the prevention and control of topical and systemic infections by pathogenic fungi. For cholesterol lowering and treatment of impaired glucose tolerance and diabetes the daily dosage conveniently amounts to between 1 and 1000 mg, preferably 10 to 100 mg, for adult patients. Depending on the dosage it is convenient to administer the daily dosage in several dosage units.

The pharmaceutical preparations conveniently contain about 1–500 mg, preferably 10–100 mg, of a compound of formula I.

The following Examples serve to illustrate the present invention in more detail. They are, however, not intended to limit its scope in any manner.

EXAMPLES

Abbreviations

AcOH=acetic acid, EtOAc=ethylacetate, EtOH=ethanol, THF=tetrahydrofurane, $Et_2O$=diethylether, MeOH=methanol, $CH_2Cl_2$=dichloromethane, BOC=t-butyloxycarbonyl, DBU=1,8-Diazabicyclo[5.4.0]undec-7-ene(1,5-5), DEAD=Diethyl azodicarboxylate, DMA=N,N-dimethylacetamide, DMAP=4-Dimethylaminopyridine, DMPU=1,3-Dimethyl-3,4,5,6-tetrahydro-2(1H)-pyrimidinone, EDCI=N-(3-Dime-thylaminopropyl)-N'-ethylcarbodiimide hydrochloride, $Et_3N$=triethylamine, HOBT=1-Hydroxybenzo-triazole, LAH=Lithium aluminium hydride, LDA=lithium diisopropylamide, n-BuLi=n-Butyllithium, $PdCl_2(dppf)$=(1,1'-bis(diphenylphosphino)ferrocene)-dichloropalladium(II).$CH_2Cl_2$ (1:1), $Pd(Ph_3P)_4$=tetrakis(triphenylphosphine)palladium, $iPr_2NEt$=DIPEA=Huenigsbase=N-ethyldiisopropylamine, TFA=trifluoroacetic acid.

General Remarks

All reactions were performed under argon.

The purification of the final amines by preparative HPLC [e.g. RP-18, acetonitrile (0.1% HCOOH)/water (0.1% HCOOH), 10% to 95% acetonitrile] yielded mixtures of the corresponding amino formiate and the corresponding halogenide which was used in the reaction. The ratio was not always determined, the purity of the final amino salts was >80% after LC-MS.

Example 1

1.1

To a solution of 3 g (29.66 mmol) 4-Hydroxypiperidine in 30 ml of $CH_2Cl_2$ was added 7.12 g (32.6 mmol) Di-tert-butyl dicarbonate. The solution was stirred at RT for 2 h, diluted with $Et_2O$ and the organic phase was washed with 1N HCl and water. The organic phase was concentrated in vacuo to yield 6.47 g (95%) 4-Hydroxy-piperidine-1-carboxylic-acid tert-butyl ester.

1.2a

To a solution of 10 g (49.7 mmol) 4-Hydroxy-piperidine-1-carboxylic-acid tert-butyl ester and 18 ml (149 mmol) of 1,4-dibromobutane in 100 ml DMF was added under ice-cooling at 0° C., 3.25 g (74.53 mmol) NaH (57% in oil). After 2 h stirring at r.t., 140 ml of sat. $NH_4Cl$-solution was added carefully. The reaction-mixture was diluted with $Et_2O$ and washed with water. The organic layer was concentrated in vacuo and the crude product was purified by chromatography on silica gel with $Et_2O$/Hexane 1:2 to yield 2.47 g (15%) of clean 4-(4-Bromo-butoxy)-piperidin-1-carboxylic acid tert-butyl ester, MS: 336 ($M^+$).

1.2b

To an ice-cooled solution of 4.85 ml (55.73 mmol) 3-Bromo-1-propanol and 13.45 ml (59.9 mmol) of 2,6-Di-tert-butylpyridine in 45 ml of $CH_2Cl_2$ was added at 0° C. 9.66 ml (58.5 mmol) of Trifluoromethanesulfonic anhydride. The reaction-mixture was stirred for 2.5h at 0° C. and then concentrated under reduced pressure. The crude residue was dissolved in 30 ml of nitromethane. This solution was added droppwise within 10 min to a solution of 6 g (27.87 mmol) 4-Hydroxymethyl-piperidine-1-carboxylicacid tert-butylester and 12.56 ml (55.74 mmol) Di-tert-butylpyridine in 90 ml of nitromethane. The mixture was stirred for 2 h at 60° C., cooled to RT, diluted with EtOAc and washed with 1N HCl, $H_2O$, sat. $NaHCO_3$ and $H_2O$ again. The organic layer was concentrated in vacuo. The crude product was purified by chromatography on silica gel with $Et_2O$/hexane 1:2 yielding 6.27 g (33%) of clean 4-(3-Bromo-propoxy methyl)-piperidin-1-carboxylic acid tert-butyl ester, MS: 336 ($M^+$).

1.3

To a solution of 2.47 g (7.35 mmol) 4-(4-Bromo-butoxy)-piperidin-1-carboxylic acid tert-butyl ester in 10 ml of $CH_2Cl_2$ was added 20 ml of 4N HCl in dioxane. The reaction-mixture was stirred for 2 h at RT and then concentrated under reduced pressure. The crude residue was suspended several times with $Et_2O$ and then dried in vacuo to yield 1.78 g (quantitative) of 4-(4-Brom-butoxy)-piperidine hydrogen chloride, MS: 236 ($M^+$).

1.4

To a solution of 0.4 g (1.47 mmol) 4-(4-Brom-butoxy)-piperidine hydrogen chloride and 0.198 ml (1.54 mmol) 4-chloro-benzoylchloride in 5 ml of $CH_2Cl_2$ was added 1 ml (5.87 mmol) of N-ethyldiisopropylamine. The reaction-mixture was stirred for 1 h at RT, diluted with $Et_2O$ and then washed with 1N HCl and water. The crude product was purified by chromatography on silica gel with EtOAc/hexane 1:1, to yield 459 mg (84%) of clean 4-(4-Bromo-butoxy)-piperidin-1-yl)-(4-chloro-phenyl)-methanone, MS: 374 ($M^+$).

1.5

To a solution of 220 mg (0.59 mmol) 4-(4-Bromo-butoxy)-piperidin-1-yl)-(4-chloro-phenyl)-methanone and 0.225 ml (2.35 mmol) of N-methylallylamine in 4 ml of acetone was added 325 mg (2.35 mmol) of $K_2CO_3$. The reaction-mixture was stirred for 20 h at 50° C., cooled down, filtered, and after concentration under reduced pressure the crude product was purified by chromatography on silica gel with $CH_2Cl_2$/MeOH/25% aqueous $NH_3$ 95.5:4:0.5 yielding 159 mg (74%) of clean {4-[4-(Allyl-methyl-amino)-butoxy]-piperidin-1-yl}-(4-chloro-phenyl)-methanone, MS: 365 ($MH^+$).

1.6

In analogy to example 1.4 and 1.5, reaction of 4-(4-Brom-butoxy)-piperidine hydrogen chloride with (4-chloro-phenyl)-acetyl chloride and N-methylallylamine yielded 1-{4-[4-(Allyl-methyl-amino)-butoxy]-piperidin-1-yl}-2-(4-chloro-phenyl)-ethanone, MS: 379 ($MH^+$).

1.7

In analogy to example 1.4 and 1.5, reaction of 4-(4-Brom-butoxy)-piperidine hydrogen chloride with (4-chloro-phenyl)-acetyl chloride and 2-ethylamino-ethanol yielded 2-(4-Chloro-phenyl)-1-(4-{4-[ethyl-(2-hydroxy-ethyl)-amino]-butoxy}-piperidin-1-yl)-ethanone, MS: 397 ($MH^+$).

1.8

In analogy to example 1.5, reaction of 4-(4-Bromo-butoxy)-piperidin-1-yl)-(4-chloro-phenyl)-methanone with 2-ethylamino-ethanol yielded (4-Chloro-phenyl)-(4-{4-[ethyl-(2-hydroxy-ethyl)-amino]-butoxy}-piperidin-1-yl)-methanone, MS: 383 ($MH^+$).

1.9

In analogy to example 1.4 and 1.5, reaction of 4-(4-Brom-butoxy)-piperidine hydrogen chloride with 4-bromo-benzoylchloride and N-methylallylamine yielded {4-[4-(Allyl-methyl-amino)-butoxy]-piperidin-1-yl}-(4-bromo-phenyl)-methanone, MS: 409 ($MH^+$, 1Br).

1.10

In analogy to example 1.3, 1.4 and 1.5, reaction of 4-(3-Bromo-propoxy methyl)-piperidin-1-carboxylic acid tert-butyl ester with 4-bromo-benzoylchloride and N-methylallylamine followed by treatment with fumaric acid yielded {4-[3-(Allyl-methyl-amino)-propoxy]-piperidin-1-yl}-(4-bromo-phenyl)-methanone fumarate, MS: 395 ($MH^+$, 1Br).

1.11

In analogy to example 1.4 and 1.5, reaction of 4-(4-Brom-butoxy)-piperidine hydrogen chloride with 4-chlorophenyl chloroformate and N-methylallylamine yielded 4-[4-(Allyl-methyl-amino)-butoxy]-piperidine-1-carboxylic acid 4-chloro-phenyl ester, MS: 381 ($MH^+$).

1.12

In analogy to example 1.4 and 1.5, reaction of 4-(4-Brom-butoxy)-piperidine hydrogen chloride with 4-chlorophenyl chloroformate and 2-ethylamino-ethanol yielded 4-{4-[Ethyl-(2-hydroxy-ethyl)-amino]-butoxy}-piperidine-1-carboxylic acid 4-chlorophenyl ester, MS: 399 ($MH^+$).

1.13

In analogy to example 1.4 and 1.5, reaction of 4-(4-Brom-butoxy)-piperidine hydrogen chloride with isobutyl chloroformate and N-methylallylamine yielded 4-[4-(Allyl-methyl-amino)-butoxy]-piperidine-1-carboxylic acid isobutyl ester, MS: 327 ($MH^+$).

1.14

In analogy to example 1.4 and 1.5, reaction of 4-(4-Brom-butoxy)-piperidine hydrogen chloride with isobutyl chloroformate and 2-ethylamino-ethanol yielded 4-{4-[Ethyl-(2-hydroxy-ethyl)-amino]-butoxy}-piperidine-1-carboxylic acid isobutyl ester, MS: 345 ($MH^+$).

1.15

In analogy to example 1.4 and 1.5, reaction of 4-(4-Brom-butoxy)-piperidine hydrogen chloride with 4-chlorophenylsulfonyl chloride and N-methylallylamine yielded Allyl-{4-[1-(4-chloro-benzenesulfonyl)-piperidin-4-yloxy]-butyl}-methyl-amine, MS: 401 ($MH^+$, 1Cl).

1.16

In analogy to example 1.4 and 1.5, reaction of 4-(4-Brom-butoxy)-piperidine hydrogen chloride with 4-bromophenylsulfonyl chloride and N-methylallylamine yielded Allyl-{4-[1-(4-bromo-benzenesulfonyl)-piperidin-4-yloxy]-butyl}-methyl-amine, MS: 445 ($MH^+$, 1Br).

1.17

In analogy to example 1.3, 1.4 and 1.5, reaction of 4-(3-Bromo-propoxy methyl)-piperidin-1-carboxylic acid tert-butyl ester with 4N HCl, 4-bromophenylsulfonyl chloride and N-methylallylamine followed by treatment with fumaric acid yielded Allyl-{3-[1-(4-bromo-benzenesulfonyl)-piperidin-4-yloxy]-propyl}-methyl-amine fumarate, MS: 431 ($MH^+$, 1Br).

1.18

In analogy to example 1.2a and 1.3, reaction of 4-Hydroxy-piperidine-1-carboxylic-acid tert-butyl ester and 1,6-dibromohexane followed by treatment with 4N HCl yielded 4-(6-Bromo-hexyloxy)-piperidine hydrochloride, MS: 264 ($MH^+$, 1Br).

1.19

In analogy to example 1.2a, 1.5 and 1.3, reaction of 4-Hydroxy-piperidine-1-carboxylic-acid tert-butyl ester and 1,6-dibromohexane, N-methylallylamine followed by treatment with 4N HCl yielded Allyl-methyl-[6-(piperidin-4-yloxy)-hexyl]-amine dihydrochloride, MS: 255 ($MH^+$).

1.20

In analogy to example 1.2a, 1.5 and 1.3, reaction of 4-Hydroxy-piperidine-1-carboxylic-acid tert-butyl ester and 1,6-dibromohexane, N-methylcyclopropylamine followed by treatment with 4N HCl yielded Cyclopropyl-methyl-[6-(piperidin-4-yloxy)-hexyl]-amine dihydrochloride, MS: 255 ($MH^+$).

Example 2

2.1

In analogy to example 1.2a, 1.3, 1.4 and 1.5, reaction of 4-Hydroxy-piperidine with 1,5-dibromopentane, (4-fluoro-phenyl)-acetyl chloride and N-methylallylamine yielded 1-{4-[5-(Allyl-methyl-amino)-pentyloxy]-piperidin-1-yl}-2-(4-fluoro-phenyl)-ethanone, MS: 377 ($MH^+$).

2.2

In analogy to example 1.2a, 1.3, 1.4 and 1.5, reaction of 4-Hydroxy-piperidine with 1,5-dibromopentane, (4-fluoro-phenyl)-acetyl chloride and diethylamine yielded 1-[4-(5-Diethylamino-pentyloxy)-piperidin-1-yl]-2-(4-fluoro-phenyl)-ethanone, MS: 379 ($MH^+$).

2.3

In analogy to example 1.2a, 1.3, 1.4 and 1.5, reaction of 4-Hydroxy-piperidine with 1,5-dibromopentane, (4-fluoro-phenyl)-acetyl chloride and N-(2-methoxyethyl) methylamine yielded 2-(4-Fluoro-phenyl)-1-(4-{5-[(2-methoxy-ethyl)-methyl-amino]-pentyloxy}-piperidin-1-yl)-ethanone, MS: 395 ($MH^+$).

2.4

In analogy to example 1.2a, 1.3, 1.4 and 1.5, reaction of 4-Hydroxy-piperidine with 1,5-dibromopentane, (4-fluoro-phenyl)-acetyl chloride and N-methylcyclopropylamine yielded 1-{4-[5-(Cyclopropyl-methyl-amino)-pentyloxy]-piperidin-1-yl}-2-(4-fluoro-phenyl)-ethanone, MS: 377 ($MH^+$).

Example 3

3.1

In analogy to example 1.7, 4-Hydroxymethyl-piperidine was converted to 2-(4-Chloro-phenyl)-1-(4-{4-[ethyl-(2-hydroxy-ethyl)-amino]-butoxymethyl}-piperidin-1-yl)-ethanone, MS: 411 ($MH^+$).

3.2

In analogy to example 1.6, 4-Hydroxymethyl-piperidine was converted to 1-{4-[4-(Allyl-methyl-amino)-butoxymethyl]-piperidin-1-yl}-2-(4-chloro-phenyl)-ethanone, MS: 393 ($MH^+$).

3.3

In analogy to example 1.5, 4-Hydroxymethyl-piperidine was converted to {4-[4-(Allyl-methyl-amino)-butoxymethyl]-piperidin-1-yl}-(4-chloro-phenyl)-methanone, MS: 379 ($MH^+$).

3.4

In analogy to example 1.8, 4-Hydroxymethyl-piperidine was converted to (4-Chloro-phenyl)-(4-{4-[ethyl-(2-hydroxy-ethyl)-amino]-butoxymethyl}-piperidin-1-yl)-methanone, MS: 397 ($MH^+$).

3.5

In analogy to example 1.11, 4-Hydroxymethyl-piperidine was converted to 4-[4-(Allyl-methyl-amino)-butoxymethyl]-piperidine-1-carboxylic acid 4-chloro-phenyl ester, MS: 395 ($MH^+$).

3.6

In analogy to example 1.12, 4-Hydroxymethyl-piperidine was converted to 4-{4-[Ethyl-(2-hydroxy-ethyl)-amino]-butoxymethyl}-piperidine-1-carboxylic acid 4-chloro-phenyl ester. MS: 413.4 ($M+H^+$)

3.7

In analogy to example 1.6 (following procedure 1.2b for the introduction of the bromo-propoxy side chain with 3-bromo-1-propanol), 4-Hydroxymethyl-piperidine was converted to 1-{4-[3-(Allyl-methyl-amino)-propoxymethyl]-piperidin-1-yl}-2-(4-chloro-phenyl)-ethanone, MS: 379 ($MH^1$).

3.8

In analogy to example 1.7 (following procedure 1.2b for the introduction of the bromo-propoxy side chain with 3-bromo-1-propanol), 4-Hydroxymethyl-piperidine was converted to 2-(4-Chloro-phenyl)-1-(4-{3-[ethyl-(2-hydroxy-ethyl)-amino]-propoxymethyl}-piperidin-1-yl)-ethanone, MS: 397 ($MH^+$).

3.9

In analogy to example 1.5 (following procedure 1.2b for the introduction of the bromo-propoxy side chain with 3-bromo-1-propanol), 4-Hydroxymethyl-piperidine was converted to {4-[3-(Allyl-methyl-amino)-propoxymethyl]-piperidin-1-yl}-(4-chloro-phenyl)-methanone, MS: 365 ($MH^+$).

3.10

In analogy to example 1.8 (following procedure 1.2b for the introduction of the bromo-propoxy side chain with 3-bromo-1-propanol), 4-Hydroxymethyl-piperidine was converted to (4-Chloro-phenyl)-(4-{3-[ethyl-(2-hydroxy-ethyl)-amino]-propoxymethyl}-piperidin-1-yl)-methanone, MS: 383 ($MH^+$).

3.11

In analogy to example 1.11 (following procedure 1.2b for the introduction of the bromo-propoxy side chain with 3-bromo-1-propanol), 4-Hydroxymethyl-piperidine was converted to 4-[3-(Allyl-methyl-amino)-propoxymethyl]-piperidine-1-carboxylic acid 4-chloro-phenyl ester, MS: 381 ($MH^+$).

3.12

In analogy to example 1.12 (following procedure 1.2b for the introduction of the bromo-propoxy side chain with 3-bromo-1-propanol), 4-Hydroxymethyl-piperidine was converted to 4-{3-[Ethyl-(2-hydroxy-ethyl)-amino]-propoxymethyl}-piperidine-1-carboxylic acid 4-chloro-phenyl ester, MS: 399 ($MH^+$).

Example 4

4.1

In analogy to example 1.6, 4-Piperidine-ethanol was converted to 1-(4-{2-[4-(Allyl-methyl-amino)-butoxy]-ethyl}-piperidin-1-yl)-2-(4-chloro-phenyl)-ethanone, MS: 407 ($MH^+$).

4.2

In analogy to example 1.7, 4-Piperidine-ethanol was converted to 2-(4-Chloro-phenyl)-1-[4-(2-{4-[ethyl-(2-hydroxy-ethyl)-amino]-butoxy}-ethyl)-piperidin-1-yl]-ethanone. MS: 425 ($MH^+$).

4.3

In analogy to example 1.5, 4-Piperidine-ethanol was converted to (4-{2-[4-(Allyl-methyl-amino)-butoxy]-ethyl}-piperidin-1-yl)-(4-chloro-phenyl)-methanone, MS: 393 ($MH^+$).

4.4

In analogy to example 1.8, 4-Piperidine-ethanol was converted to (4-Chloro-phenyl)-[4-(2-{4-[ethyl-(2-hydroxy-ethyl)-amino]-butoxy}-ethyl)-piperidin-1-yl]-methanone, MS: 411 ($MH^+$).

4.5

In analogy to example 1.11, 4-Piperidine-ethanol was converted to 4-{2-[4-(Allyl-methyl-amino)-butoxy]-ethyl}-piperidine-1-carboxylic acid 4-chloro-phenyl ester, MS: 409 ($MH^1$).

4.6

In analogy to example 1.12, 4-Piperidine-ethanol was converted to 4-(2-{4-[Ethyl-(2-hydroxy-ethyl )-amino]-butoxy}-ethyl )-piperidine-1-carboxylic acid 4-chloro-phenyl ester, MS: 427 ($MH^+$).

4.7

In analogy to example 1.13, 4-Piperidine-ethanol was converted to isobutyl-chloroformate to yield: 4-{2-[4-(Allyl-methyl-amino)-butoxy]-ethyl}-piperidine-1-carboxylic acid isobutyl ester, MS: 355 ($MH^+$).

4.8

In analogy to example 1.14, 4-Piperidine-ethanol was converted to 4-(2-{4-[Ethyl-(2-hydroxy-ethyl)-amino]-butoxy}-ethyl)-piperidine-1-carboxylic acid isobutyl ester, MS: 373 ($MH^+$).

4.9

In analogy to example 1.6 (following procedure 1.2b for the introduction of the bromo-propoxy side chain), 4-Piperidine-ethanol was converted to 1-(4-{2-[3-(Allyl-methyl-amino)-propoxy]-ethyl}-piperidin-1-yl)-2-(4-chloro-phenyl)-ethanone, MS: 393 ($MH^+$).

4.10

In analogy to example 1.7 (following procedure 1.2b for the introduction of the bromo-propoxy side chain), 4-Piperidine-ethanol was converted to 2-(4-Chloro-phenyl)-1[4-(2-{3-[ethyl-(2-hydroxy-ethyl)-amino]-propoxy}-ethyl)-piperidin-1-yl]-ethanone, MS: 411 ($MH^+$).

4.11

In analogy to example 1.5 (following procedure 1.2b for the introduction of the bromo-propoxy side chain), 4-Piperidine-ethanol was converted to (4-{2-[3-(Allyl-methyl-amino)-propoxy]-ethyl}-piperidin-1-yl)-(4-chloro-phenyl)-methanone, MS: 379 ($MH^+$).

4.12

In analogy to example 1.8 (following procedure 1.2b for the introduction of the bromo-propoxy side chain), 4-Piperidine-ethanol was converted to (4-Chloro-phenyl)-[4-(2-{3-[ethyl-(2-hydroxy-ethyl)-amino]-propoxy}-ethyl)-piperidin-1-yl]-methanone, MS: 397 ($MH^+$).

4.13

In analogy to example 1.11 (following procedure 1.2b for the introduction of the bromo-propoxy side chain), 4-Piperidine-ethanol was converted to 4-{2-[3-(Allyl-methyl-amino)-propoxy]-ethyl}-piperdine-1-carboxylic acid 4-chloro-phenyl ester, MS: 395 ($MH^+$).

4.14

In analogy to example 1.12 (following procedure 1.2b for the introduction of the bromo-propoxy side chain), 4-Piperidine-ethanol was converted to 4-(2-{3-[Ethyl-(2-hydroxy-ethyl)-amino]-propoxy}-ethyl)-piperidine-1-carboxylic acid 4-chloro-phenyl ester, MS: 413 ($MH^+$).

4.15

In analogy to example 1.6 (following procedure 1.2b for the introduction of the bromo-ethoxy side chain with 2-bromoethanol), 4-Piperidine-ethanol was converted to 1-(4-{2-[2-(Allyl-methyl-amino)-ethoxy]-ethyl}-piperidin-1-yl)-2-(4-chloro-phenyl)-ethanone, MS: 379 ($MH^+$).

4.16

In analogy to example 1.7 (following procedure 1.2b for the introduction of the bromo-ethoxy side chain with 2-bromoethanol), 4-Piperidine-ethanol was converted to 1-(4-{2-[2-(Allyl-methyl-amino)-ethoxy]-ethyl}-piperidin-1-yl)-2-(4-chloro-phenyl)-ethanone, MS: 397 ($MH^+$).

4.17

In analogy to example 1.5 (following procedure 1.2b for the introduction of the bromo-ethoxy side chain with 2-bromoethanol), 4-Piperidine-ethanol was converted to 1-(4-{2-[2-(Allyl-methyl-amino)-ethoxy]-ethyl}-piperidin-1-yl)-2-(4-chloro-phenyl)-ethanone, MS: 365 ($MH^+$).

4.18

In analogy to example 1.8 (following procedure 1.2b for the introduction of the bromo-ethoxy side chain with 2-bromoethanol), 4-Piperidine-ethanol was converted to (4-Chloro-phenyl)-[4-(2-{2-[ethyl-(2-hydroxy-ethyl)-amino]-ethoxy}-ethyl)-piperidin-1-yl]-methanone, MS: 383 ($MH^+$).

4.19

In analogy to example 1.11 (following procedure 1.2b for the introduction of the bromo-ethoxy side chain with 2-bromoethanol), 4-Piperidine-ethanol was converted to 4-{2-[2-(Allyl-methyl-amino)-ethoxy]-ethyl}-piperidine-1-carboxylic acid 4-chloro-phenyl ester, MS: 381 ($MH^+$).

4.20

In analogy to example 1.12 (following procedure 1.2b for the introduction of the bromo-ethoxy side chain with 2-bromoethanol), 4-Piperidine-ethanol was converted to 4-(2-{2-[Ethyl-(2-hydroxy-ethyl)-amino]-ethoxy}-ethyl)-piperidine-1-carboxylic acid 4-chloro-phenyl ester, MS: 399 ($MH^+$).

4.21

In analogy to example 1.13 (following procedure 1.2b for the introduction of the bromo-ethoxy side chain with 2-bromoethanol), 4-Piperidine-ethanol was converted to 4-{2-[2-(Allyl-methyl-amino)-ethoxy]-ethyl}-piperidine-1-carboxylic acid isobutyl ester, MS: 327 ($MH^+$).

4.22

In analogy to example 1.14 (following procedure 1.2b for the introduction of the bromo-ethoxy side chain with 2-bromoethanol), 4-Piperidine-ethanol was converted to 4-(2-{2-[Ethyl-(2-hydroxy-ethyl)-amino]-ethoxy}-ethyl)-piperidine-1-carboxylic acid isobutyl ester, MS: 345 ($MH^+$).

Example 5

A solution of 0.153 mmol of amine dihydrochloride and 0.5 mmol triethylamine in 0.35 ml dry $CH_2Cl_2$ was treated with 0.23 mmol isocyanate in 0.54 ml dry $CH_2Cl_2$. The solution was allowed to stand over night at room temperature. The resulting reaction mixture was evaporated and treated with 0.15 ml formic acid and purified by preparative HPLC [RP-18, acetonitrile (0.1% HCOOH)/water (0.1% HCOOH), 10% to 95% acetonitrile]. After evaporation the corresponding compound was obtained as a mixture of amino hydrochloride and formiate. The following compounds were obtained using the corresponding amines and isocyanates:

| Example | Compound | MS MH+ | Amine | isocyanate |
|---|---|---|---|---|
| 5.1 | 4-[6-(Allyl-methyl-amino)-hexyloxy]-piperidine-1-carboxylic acid (4-fluoro-3-trifluoromethyl-phenyl)-amide | 460 | Allyl-methyl-[6-(piperidin-4-yloxy)-hexyl]-amine | 4-Fluoro-3-trifluoromethyl-phenylisocyanate |
| 5.2 | 4-[6-(Allyl-methyl-amino)-hexyloxy]-piperidine-1-carboxylic acid (2,4-difluoro-phenyl)-amide | 410 | Allyl-methyl-[6-(piperidin-4-yloxy)-hexyl]-amine | 2,4-Difluorophenyl-isocyanate |
| 5.3 | 4-[6-(Allyl-methyl-amino)-hexyloxy]-piperidine-1-carboxylic acid (2,4-dimethoxy-phenyl)-amide | 434 | Allyl-methyl-[6-(piperidin-4-yloxy)-hexyl]-amine | 2,4 Dimethoxy-phenylisocyanate |
| 5.4 | 4-[6-(Allyl-methyl-amino)-hexyloxy]-piperidine-1-carboxylic acid (4-fluoro-phenyl)-amide | 392 | Allyl-methyl-[6-(piperidin-4-yloxy)-hexyl]-amine | 4-Fluorophenyl-isocyanate |
| 5.5 | 4-[6-(Allyl-methyl-amino)-hexyloxy]-piperidine-1-carboxylic acid (4-methoxy-phenyl)-amide | 404 | Allyl-methyl-[6-(piperidin-4-yloxy)-hexyl]-amine | 4-Methoxyphenyl-isocyanate |
| 5.6 | 4-[6-(Allyl-methyl-amino)-hexyloxy]-piperidine-1-carboxylic acid p-tolylamide | 388 | Allyl-methyl-[6-(piperidin-4-yloxy)-hexyl]-amine | 4-Methylphenyl-isocyanate |
| 5.7 | 4-[6-(Allyl-methyl-amino)-hexyloxy]-piperidine-1-carboxylic acid (4-methoxy-2-methyl-phenyl)-amide | 418 | Allyl-methyl-[6-(piperidin-4-yloxy)-hexyl]-amine | 4-Methoxy-2-Methylphenyl-isocyanate |
| 5.8 | 4-[6-(Allyl-methyl-amino)-hexyloxy]-piperidine-1-carboxylic acid (2,4-dimethyl-phenyl)-amide | 402 | Allyl-methyl-[6-(piperidin-4-yloxy)-hexyl]-amine | 2,4 Dimethyl-phenylisocyanate |
| 5.9 | 4-[6-(Allyl-methyl-amino)-hexyloxy]-piperidine-1-carboxylic acid (3,4,5-trimethoxy-phenyl)-amide | 464 | Allyl-methyl-[6-(piperidin-4-yloxy)-hexyl]-amine | 3,4,5 Trimethoxy-phenylisocyanate |
| 5.10 | 4-[6-(Allyl-methyl-amino)-hexyloxyl]-piperidine-1-carboxylic acid (3,4-dimethyl-phenyl)-amide | 402 | Allyl-methyl-[6-(piperidin-4-yloxy)-hexyl]-amine | 3,4 Dimethyl-phenylisocyanate |
| 5.11 | 4-[6-(Allyl-methyl-amino)-hexyloxy]-piperidine-1-carboxylic acid (4-acetyl-phenyl)-amide | 416 | Allyl-methyl-[6-(piperidin-4-yloxy)-hexyl]-amine | 4-Acetylphenyl-isocyanate |
| 5.12 | 4-[6-(Allyl-methyl-amino)-hexyloxy]-piperidine-1-carboxylic acid (4-butyl-phenyl)-amide | 430 | Allyl-methyl-[6-(piperidin-4-yloxy)-hexyl]-amine | 4-Butylphenyl-isocyanate |
| 5.13 | 4-[6-(Allyl-methyl-amino)-hexyloxy]-piperidine-1-carboxylic acid (4-methylsulfanyl-phenyl)-amide | 420 | Allyl-methyl-[6-(piperidin-4-yloxy)-hexyl]-amine | 4-Methylmercapto-phenylisocyanate |
| 5.14 | 4-[6-(AIlyl-methyl-amino)-hexyloxy]-piperidine-1-carboxylic acid (4-isopropyl-phenyl)-amide | 416 | Allyl-methyl-[6-(piperidin-4-yloxy)-hexyl]-amine | 4-Isopropylphenyl-isocyanate |
| 5.15 | 4-[6-(Allyl-methyl-amino)-hexyloxy]-piperidine-1-carboxylic acid (3,4-dichloro-phenyl)-amide | 442 (2 Cl) | Allyl-methyl-[6-(piperidin-4-yloxy)-hexyl]-amine | 3,4 Dichlorphenyl-isocyanate |
| 5.16 | 4-[6-(Allyl-methyl-amino)-hexyloxy]-piperidine-1-carboxylic acid (4-bromo-phenyl)-amide | 452 (1 Br) | Allyl-methyl-[6-(piperidin-4-yloxy)-hexyl]-amine | 4-Bromphenyl-isocyanate |
| 5.17 | 4-[6-(Allyl-methyl-amino)-hexyloxy]-piperidine-1-carboxylic acid naphthalen-2-ylamide | 424 | Allyl-methyl-[6-(piperidin-4-yloxy)-hexyl]-amine | 2-Naphthyl-isocyanate |
| 5.18 | 4-[6-(Allyl-methyl-amino)-hexyloxy]-piperidine-1-carboxylic acid naphthalen-1-ylamide | 424 | Allyl-methyl-[6-(piperidin-4-yloxy)-hexyl]-amine | 1-Naphthyl-isocyanate |
| 5.19 | 4-[6-(Allyl-methyl-amino)-hexyloxy]-piperidine-1- | 402 | Allyl-methyl-[6-(piperidin-4-yloxy)- | 2 -Phenylethyl-isocyanate |

-continued

| Example | Compound | MS MH+ | Amine | isocyanate |
|---|---|---|---|---|
| | carboxylic acid phenethyl-amide | | hexyl]-amine | |

Example 6

A solution of 0.153 mmol of amine dihydrochloride in 0.35 ml dry dioxane was treated with 0.77 mmol (5 equivalents) Hünigsbase and 0.2 mmol chloroformate in 0.54 ml dry dioxane. The solution was allowed to stand over night at room temperature and the resulting reaction mixture was treated with 0.15 ml formic acid and purified by preparative HPLC [RP-18, acetonitrile (0.1% HCOOH)/water (0.1% HCOOH), 10% to 95% acetonitrile]. After evaporation the corresponding compound was obtained as a mixture of amino hydrochloride and formiate. The following compounds were obtained using the corresponding amines and chloroformates:

| Example | Compound | MS $MH^+$ | Amine | isocyanate |
|---|---|---|---|---|
| 6.1 | 4-[6-(Allyl-methyl-amino)-hexyloxy]-piperidine-1-carboxylic acid ethyl ester | 327 | Allyl-methyl-[6-(piperidin-4-yloxy)-hexyl]-amine | Ethylchloroformate |
| 6.2 | 4-[6-(Allyl-methyl-amino)-hexyloxy]-piperidine-1-carboxylic acid 9H-fluoren-9-ylmethyl ester | 477 | Allyl-methyl-[6-(piperidin-4-yloxy)-hexyl]-amine | 9-Fluorenylmethyl-chloroformate |
| 6.3 | 4-[6-(Allyl-methyl-amino)-hexyloxy]-piperidine-1-carboxylic acid methyl ester | 313 | Allyl-methyl-[6-(piperidin-4-yloxy)-hexyl]-amine | Methyl-chloroformate |
| 6.4 | 4-[6-(Allyl-methyl-amino)-hexyloxy]-piperidine-1-carboxylic acid 2,2,2-trichloro-1,1-dimethyl-ethyl ester | 457 (3 Cl) | Allyl-methyl-[6-(piperidin-4-yloxy)-hexyl]-amine | 2,2,2-Trichloro-1,1-Dimethylethyl-chloroformate |
| 6.5 | 4-[6-( allyl-methyl-amino)-hexyloxy]-piperidine-1-carboxylic acid 4-nitro-phenyl ester | 420 | Allyl-methyl-[6-(piperidin-4-yloxy)-hexyl]-amine | 4-Nitrophenyl-chloroformate |
| 6.6 | 4-[6-(Allyl-methyl-amino)-hexyloxy]-piperidine-1-carboxylic acid isobutyl ester | 355 | Allyl-methyl-[6-(piperidin-4-yloxy)-hexyl]-amine | Isobutyl-chloroformate |
| 6.7 | 4-[6-(Allyl-methyl-amino)-hexyloxy]-piperidine-1-carboxylic acid benzyl ester | 389 | Allyl-methyl-[6-(piperidin-4-yloxy)-hexyl]-amine | Benzyl-chloroformate |
| 6.8 | 4-[6-(Allyl-methyl-amino)-hexyloxy]-piperidine-1-carboxylic acid allyl ester | 339 | Allyl-methyl-[6-(piperidin-4-yloxy)-hexyl]-amine | Allylchloroformate |
| 6.9 | 4-[6-(Allyl-methyl-amino)-hexyloxy]-piperidine-1-carboxylic acid phenyl ester | 375 | Allyl-methyl-[6-(piperidin-4-yloxy)-hexyl]-amine | Phenyl-chloroformate |
| 6.10 | 4-[6-(Allyl-methyl-amino)-hexyloxy]-piperidine-1-carboxylic acid butyl ester | 355 | Allyl-methyl-[6-(piperidin-4-yloxy)-hexyl]-amine | Butylchloroformate |
| 6.11 | 4-[6-(Allyl-methyl-amino)-hexyloxy]-piperidine-1-carboxylic acid 4-methoxycarbonyl-phenyl ester | 433 | Allyl-methyl-[6-(piperidin-4-yloxy)-hexyl]-amine | 4-Methoxy-carbonylphenyl-chloroformate |
| 6.12 | 4-[6-(Allyl-methyl-amino)-hexyloxy]-piperidine-1-carboxylic acid 4-fluoro-phenylester | 393 | Allyl-methyl-[6-(piperidin-4-yloxy)-hexyl]-amine | 4-Fluorophenyl-chloroformate |
| 6.13 | 4-[6-(Allyl-methyl-amino)-hexyloxy]-piperidine-1-carboxylic acid 4-bromo-phenyl ester | 453 (1 Br) | Allyl-methyl-[6-(piperidin-4-yloxy)-hexyl]-amine | 4-Bromophenyl-chloroformate |
| 6.14 | 4-[6-(Allyl-methyl-amino)-hexyloxy]-piperidine-1-carboxylic acid 4-chloro-phenyl ester | 409 (1 Cl) | Allyl-methyl-[6-(piperidin-4-yloxy)-hexyl]-amine | 4-Chlorophenyl-chloroformate |

-continued

| Example | Compound | MS MH+ | Amine | isocyanate |
|---|---|---|---|---|
| 6.15 | 4-[6-(Allyl-methyl-amino)-hexyloxy]-piperidine-1-carboxylic acid p-tolyl ester | 389 | Allyl-methyl-[6-(piperidin-4-yloxy)-hexyl]-amine | 4-Tosyl-chloroformate |

Example 7

A solution of 1.5 mmol trichloromethyl-chloroformate (diphosgene) in 20 ml $CH_2Cl_2$ was treated at 0° C. with 3 mmol 4-Trifluoromethyl-phenol and 3 mmol quinoline and then stirred for 3 h at room temperature. The reaction mixture was then cooled (0° C.) and a solution of 1 mmol Allyl-methyl-[6-(piperidin-4-yloxy)-hexyl]-amine (the amine dihydrochloride was extracted with 1 N NaOH/$CH_2Cl_2$) and 2.5 mmol pyridine in 3 ml $CH_2Cl_2$ was added, followed by 1 mmol DMAP. The mixture was stirred over night at room temperature, evaporated and treated with 0.15 ml formic acid and purified by preparative HPLC [RP-18, acetonitrile (0.1% HCOOH)/water (0.1% HCOOH), 10% to 95% acetonitrile]. After evaporation 4-[6-(Allyl-methyl-amino)-hexyloxy]-piperidine-1-carboxylic acid 4-trifluoromethyl-phenyl ester was obtained as a mixture of amino hydrochloride and formiate, MS: 443 ($MH^+$).

Example 8

A solution of 0.135 mmol amine dihydrochloride in 0.75 ml dry $CH_2Cl_2$ was treated with 4 equivalents of triethylamine followed by a solution of 0.175 mmol (1.3 equivalente) sulfamoylchloride in 0.25 ml dry $CH_2Cl_2$. The solution was allowed to stand over night at room temperature, was evaporated and then treated with 0.15 ml formic acid and purified by preparative HPLC [RP-18, acetonitrile (0.1% HCOOH)/water (0.1% HCOOH), 10% to 95% acetonitrile]. After evaporation of the corresponding fraction, the sulfamide was received as a mixture of amino hydrochloride and formiate. The following compounds were obtained using the corresponding amines and sulfamoylchlorides:

| Example | Compound | MS MH+ | Amine | Sulfamoylchloride |
|---|---|---|---|---|
| 8.1 | 4-[6-(Allyl-methyl-amino)-hexyloxy]-piperidine-1-sulfonic acid benzylamide | 424 | Allyl-methyl-[6-(piperidin-4-yloxy)-hexyl]-amine | Benzyl-sulfamoylchloride |
| 8.2 | 4-[6-(Allyl-methyl-amino)-hexyloxy]-piperidine-1-sulfonic acid butylamide | 390 | Allyl-methyl-[6-(piperidin-4-yloxy)-hexyl]-amine | Butyl-sulfamoylchloride |
| 8.3 | 4-6-(Allyl-methyl-amino)-hexyloxy]-piperidine-1-sulfonic acid phenethyl-amide | 438 | Allyl-methyl-[6-(piperidin-4-yloxy)-hexyl]-amine | Phenethyl-sulfamoylchloride |
| 8.4 | 4-[6-(Allyl-methyl-amino)-hexyloxy]-piperidine-1-sulfonic acid (furan-2-ylmethyl)-amide | 414 | Allyl-methyl-[6-(piperidin-4-yloxy)-hexyl]-amine | Furan-2-ylmethyl-sulfamoylchloride |
| 8.5 | {4-[6-(Allyl-methyl-amino)-hexyloxy]-piperidine-1-sulfonylaminol-acetic acid ethyl ester | 420 | Allyl-methyl-[6-(piperidin-4-yloxy)-hexyl]-amine | Chlorosulfonyl-amino-acetic acid ethyl ester |
| 8.6 | 4-[6-(Allyl-methyl-amino)-hexyloxy]-piperidine-1-sulfonic acid cyclohexylmethyl-amide | 430 | Allyl-methyl-[6-(piperidin-4-yloxy)-hexyl]-amine | Cyclohexylmethyl-sulfamoylchloride |
| 8.7 | 4-[6-(Allyl-methyl-amino)-hexyloxy]-piperidine-1-sulfonic acid cyclopropylamide | 374 | Allyl-methyl-[6-(piperidin-4-yloxy)-hexyl]-amine | Cyclopropyl-sulfamoylchloride |
| 8.8 | 4-[6-(Allyl-methyl-amino)-hexyloxy]-piperidine-1-sulfonic acid (2,2,2-trifluoro-ethyl)-amide | 416 | Allyl-methyl-[6-(piperidin-4-yloxy)-hexyl]-amine | 2,2,2-Trifluoroethyl-sulfamoylchloride |
| 8.9 | 4-[6-(Allyl-methyl-amino)-hexyloxy]-piperidine-1-sulfonic acid (benzo[1,3]dioxol-5-ylmethyl)-amide | 468 | Allyl-methyl-[6-(piperidin-4-yloxy)-hexyl]-amine | Benzo[1,3]dioxol-5-ylmethyl-sulfamoylchloride |
| 8.10 | 4-[6-(Allyl-methyl-amino)-hexyloxy]-piperidine-1-sulfonic acid 4-fluoro-benzylamide | 442 | Allyl-methyl-[6-(piperidin-4-yloxy)-hexyl]-amine | 4-Fluoro-benzyl-sulfamoylchloride |
| 8.11 | 4-[6-(Cyclopropyl-methyl-amino)-hexyloxy]- | 444 (1 Cl) | Cyclopropyl-methyl-[6- | 4-Chloro-phenyl-sulfamoyl chloride |

-continued

| Example | Compound | MS MH+ | Amine | Sulfamoylchloride |
|---|---|---|---|---|
| | piperidine-1-sulfonic acid (4-chloro-phenyl)-amide | | (piperidin-4-yloxy)-hexyl]-amine | |
| 8.12 | 4-[6-(Allyl-methyl-amino)-hexyloxy]-piperidine-1-sulfonic acid (4-chloro-phenyl)-amide | 444 (1 Cl) | Allyl-methyl-[6-(piperidin-4-yloxy)-hexyl]-amine | 4-Chloro-phenyl-sulfamoyl chloride |
| 8.13 | 4-[6-(Cyclopropyl-methyl-amino)-hexyloxy]-piperidine-1-sulfonic acid (4-fluoro-phenyl)-amide | 428 | Cyclopropyl-methyl-[6-(piperidin-4-yloxy)-hexyl]-amine | 4-Fluoro-phenyl-sulfamoyl chloride |
| 8.14 | 4-[6-(Allyl-methyl-amino)-hexyloxy]-piperidine-1-sulfonic acid (4-fluoro-phenyl)-amide | 428 | Allyl-methyl-[6-(piperidin-4-yloxy)-hexyl]-amine | 4-Fluoro-phenyl-sulfamoyl chloride |
| 8.15 | 4-[6-( Cyclopropyl-methyl-amino)-hexyloxy]-piperidine-1-sulfonic acid (4-bromo-phenyl)-amide | 488 (1 Br) | Cyclopropyl-methyl-[6-(piperidin-4-yloxy)-hexyl]-amine | 4-Bromo-phenyl-sulfamoyl chloride |
| 8.16 | 4-[6-(Allyl-methyl-amino)-hexyloxy]-piperidine-1-sulfonic acid (4-bromo-phenyl)-amide | 488 (1 Br) | Allyl-methyl-[6-(piperidin-4-yloxy)-hexyl]-amine | 4-Bromo-phenyl-sulfamoyl chloride |
| 8.17 | 4-[6-(Cyclopropyl-methyl-amino)-hexyloxy]-piperidine-1-sulfonic acid (p-tolyl)-amide | 424 | Cyclopropyl-methyl-[6-(piperidin-4-yloxy)-hexyl]-amine | p-tolyl-sulfamoylchloride |
| 8.18 | 4-[6-(Allyl-methyl-amino)-hexyloxy]-piperidine-1-sulfonic acid (p-tolyl)-amide | 424 | Allyl-methyl-[6-(piperidin-4-yloxy)-hexyl]-amine | p-tolyl-sulfamoylchloride |
| 8.19 | 4-[6-(Cyclopropyl-methyl-amino)-hexyloxy]-piperidine-1-sulfonic acid (3,4-difluoro-phenyl)-amide | 446 | Cyclopropyl-methyl-[6-(piperidin-4-yloxy)-hexyl]-amine | Difluorophenyl-sulfamoyl chloride |
| 8.20 | 4-[6-(Allyl-methyl-amino)-hexyloxy]-piperidine-1-sulfonic acid (3,4-difluoro-phenyl)-amide | 446 | Allyl-methyl-[6-(piperidin-4-yloxy)-hexyl]-amine | 3,4-Difluorophenyl-sulfamoyl chloride |
| 8.21 | 4-[6-(Cyclopropyl-methyl-amino)-hexyloxy]-piperidine-1-sulfonic acid (4-trifluoromethyl-phenyl)-amide | 478 | Cyclopropyl-methyl-[6-(piperidin-4-yloxy)-hexyl]-amine | 4-Trifluoromethyl-phenyl-sulfamoylchloride |
| 8.22 | 4-[6-(Allyl-methyl-amino)-hexyloxy]-piperidine-1-sulfonic acid (4-trifluoromethyl-phenyl)-amide | 478 | Allyl-methyl-[6-(piperidin-4-yloxy)-hexyl]-amine | 4-Trifluoromethyl-phenyl-sulfamoylchloride |
| 8.23 | 4-[6-(Cyclopropyl-methyl-amino)-hexyloxy]-piperidine-1-sulfonic acid (3-fluoro -phenyl)-amide | 428 | Cyclopropyl-methyl-[6-(piperidin-4-yloxy)-hexyl]-amine | 3-Fluorophenyl-sulfamoylchloride |
| 8.24 | 4-[6-(Allyl-methyl-amino)-hexyloxy]-piperidine-1-sulfonic acid (3-fluoro-phenyl)-amide | 428 | Allyl-methyl-[6-(piperidin-4-yloxy)-hexyl]-amine | 3-Fluorophenyl-sulfamoylchloride |
| 8.25 | 4-[6-(Cyclopropyl-methyl-amino)-hexyloxy]-piperidine-1-sulfonic acid (4-cyano-phenyl)-amide | 435 | Cyclopropyl-methyl-[6-(piperidin-4-yloxy)-hexyl]-amine | 4-Cyanophenyl-sulfamoylchloride |
| 8.26 | 4-[6-(Allyl-methyl-amino)-hexyloxy]-piperidine-1-sulfonic acid (4-cyano-phenyl)-amide | 435 | Allyl-methyl-[6-(piperidin-4-yloxy)-hexyl]-amine | 4-Cyanophenyl-sulfamoylchloride |
| 8.27 | 4-[6-( Cyclopropyl-methyl-amino)-hexyloxy]-piperidine-1-sulfonic acid (2,4-difluoro-phenyl)-amide | 446 | Cyclopropyl-methyl-[6-(piperidin-4-yloxy)-hexyl]-amine | 2,4-Difluorophenyl-sulfamoylchloride |
| 8.28 | 4-[6-(Allyl-methyl-amino)-hexyloxy]-piperidine-1-sulfonic acid (2,4-difluoro-phenyl)-amide | 446 | Allyl-methyl-[6-(piperidin-4-yloxy)-hexyl]-amine | 2,4-Difluorophenyl-sulfamoylchloride |
| 8.29 | 4-6-(Cyclopropyl-methyl-amino)-hexyloxy]-piperidine-1-sulfonic acid (4-methoxy-phenyl)-amide | 440 | Cyclopropyl-methyl-[6-(piperidin-4-yloxy)-hexyl]-amine | 4-Methoxyphenyl-sulfamoylchloride |

-continued

| Example | Compound | MS $MH^+$ | Amine | Sulfamoylchloride |
|---|---|---|---|---|
| 8.30 | 4-[6-(Allyl-methyl-amino)-hexyloxy]-piperidine-1-sulfonic acid (4-methoxy-phenyl)-amide | 440 | Allyl-methyl-[6-(piperidin-4-yloxy)-hexyl]-amine | 4-Methoxyphenyl-sulfamoylchloride |
| 8.31 | 4-[6-(Cyclopropyl-methyl-amino)-hexyloxy]-piperidine-1-sulfonic acid (2,5-difluoro-phenyl)-amide | 446 | Cyclopropyl-methyl-[6-(piperidin-4-yloxy)-hexyl]-amine | 2,5 -Difluorophenyl-sulfamoylchloride |
| 8.32 | 4-[6-(Allyl-methyl-amino)-hexyloxy]-piperidine-1-sulfonic acid (2,5-difluoro-phenyl)-amide | 446 | Allyl-methyl-[6-(piperidin-4-yloxy)-hexyl]-amine | 2,5-Difluorophenyl-sulfamoylchloride |
| 8.33 | 4-[6-(Cyclopropyl-methyl-amino)-hexyloxy]-piperidine-1-sulfonic acid (phenyl)-amide | 410 | Cyclopropyl-methyl-[6-(piperidin-4-yloxy)-hexyl]-amine | Phenyl-sulfamoylcbloride |
| 8.34 | 4-[6-(Allyl-methyl-amino)-hexyloxy]-piperidine-1-sulfonic acid (phenyl)-amide | 410 | Allyl-methyl-[6-(piperidin-4-yloxy)-hexyl]-amine | Phenyl-sulfamoylchloride |

Example 9

A solution of 3 g (10 mmol) 4-(6-Bromo-hexyloxy)-piperidine hydrochloride and 3.44 g (18 mmol) of Phenyl-sulfamoyl chloride in 100 ml dry $CH_2Cl_2$ was treated with 6.95 ml (49.9 mmol) of triethylamine. The reaction was stirred for 4 h at RT, diluted with $CH_2Cl_2$ and washed with water. The organic phase was dried ($MgSO_4$) and evaporated to yield 5.67 g (quantitative) of 4-(6-Bromo-hexyloxy)-piperidine-1-sulfonic acid phenylamide.

A solution of the amine (0.26 mmol; 1.5 equivalents) in 0.7 ml DMF was treated with 4-(6-Bromo-hexyloxy)-piperidine-1-sulfonic acid phenylamide (0.17 mmol; 1 equivalent) in 0.25 ml DMF, sodium iodide (1 equvivalent; 0.17 mmol) and with Huenig's base (1 equivalent; 0.17 mmol). The reaction mixture was shaken over night at 60° C., then treated with 0.2 ml formic acid and purified by preparative HPLC [RP-18, acetonitrile (0.1% HCOOH)/water (0.1% HCOOH), 10% to 95% acetonitrile]. After evaporation of the corresponding fraction, the compound was received as a mixture of amino hydrobromide and formiate. The following compounds were obtained using the corresponding amines:

| Example | Compound | MS $MH^+$ | Amine |
|---|---|---|---|
| 9.1 | 4-(6-Azepan-1-yl-hexyloxy)-piperidine-1-sulfonic acid phenylamide | 438 | Azepane |
| 9.2 | 4-{6-[(2-Methoxy-ethyl)-methyl-amino]-hexyloxy}-piperidine-1-sulfonic acid phenylamide | 428 | (2-Methoxy-ethyl)-methyl-amine |
| 9.3 | 4-[6-(Ethyl-methyl-amino)-hexyloxy]-piperidine-1-sulfonic acid phenylamide | 398 | Ethyl-methyl-amine |
| 9.4 | 4-[6-(2-Methyl-piperidin-1-yl)-hexyloxy]-piperidine-1-sulfonic acid phenylamide | 438 | 2-Methyl-piperidine |
| 9.5 | 4-{6-[(2-Hydroxy-ethyl)-methyl-amino]-hexyloxy}-piperidine-1-sulfonic acid phenylamide | 414 | (2-Hydroxy-ethyl)-methyl-amine |
| 9.6 | {Methyl-[6-(1-phenylsulfamoyl-piperidin-4-yloxy)-hexyl]-amino}-acetic acid ethyl ester | 456 | Amino-acetic acid ethyl ester |
| 9.7 | 4-[6-(Butyl-methyl-amino)-hexyloxy]-piperidine-1-sulfonic acid phenylamide | 426 | Butyl-methyl-amine |
| 9.8 | 4-(6-Diallylamino-hexyloxy)-piperidine-1-sulfonic acid phenylamide | 436 | Diallylamine |
| 9.9 | 4-(6-Pyrrolidin-1-yl-hexyloxy)-piperidine-1-sulfonic acid phenylamide | 410 | Pyrrolidine |
| 9.10 | 4-[6-(Methyl-prop-2-ynyl-amino)-hexyloxy]-piperidine-1-sulfonic acid phenylamide | 408 | Methyl-prop-2-ynyl-amine |
| 9.11 | 4-(6-Piperidin-1-yl-hexyloxy)-piperidine-1-sulfonic acid phenylamide | 424 | Piperidine |
| 9.12 | 4-[6-(Ethyl-isopropyl-amino)-hexyloxy]-piperidine-1-sulfonic acid phenylamide | 426 | Ethyl-isopropyl-amine |
| 9.13 | 4-(6-Morpholin-4-yl-hexyloxy)-piperidine-1-sulfonic acid phenylamide | 426 | Morpholine |
| 9.14 | 4-[6-(Isopropyl-methyl-amino)-hexyloxy]-piperidine-1-sulfonic acid phenylamide | 412 | Isopropyl-methyl-amine |

-continued

| Example | Compound | MS $MH^+$ | Amine |
|---|---|---|---|
| 9.15 | 4-[6-(3,6-Dihydro-2H-pyridin-1-yl)-hexyloxy]-piperidine-1-sulfonic acid phenylamide | 422 | 3,6-Dihydro-2H-pyridine |
| 9.16 | 4-{6-[Ethyl-(2-hydroxy-ethyl)-amino]-hexyloxy}-piperidine-1-sulfonic acid phenylamide | 428 | Ethyl-(2-hydroxy-ethyl)-amine |
| 9.17 | 4-(6-Dimethylamino-hexyloxy)-piperidine-1-sulfonic acid phenylamide | 384 | Dimethylamine |
| 9.18 | 4-[6-(Methyl-propyl-amino)-hexyloxy]-piperidine-1-sulfonic acid phenylamide | 412 | Methyl-propyl-amine |
| 9.19 | 4-(6-Diethylamino-hexyloxy)-piperidine-1-sulfonic acid phenylamide | 412 | Diethylamine |
| 9.20 | 4-(6-Thiomorpholin-4-yl-hexyloxy)-piperidine-1-sulfonic acid phenylamide | 442 | Thiomorpholine |
| 9.21 | 4-[6-(Butyl-ethyl-amino)-hexyloxy]-piperidine-1-sulfonic acid phenylamide | 440 | Butyl-ethyl-amine |
| 9.22 | 4-(6-Thiazolidin-3-yl-hexyloxy)-piperidine-1-sulfonic acid phenylamide | 428 | Thiazolidine |
| 9.23 | 4-[6-(4-Hydroxy-piperidin-l-yl)-hexyloxy]-piperidine-1-sulfonic acid phenylamide | 440 | 4-Hydroxy-piperidine |
| 9.24 | 4-[6-(4-Methyl-piperazin-l-yl)-hexyloxy]-piperidine-1-sulfonic acid phenylamide | 439 | 4-Methyl-piperazine |
| 9.25 | 4-[6-(4-Hydroxymethyl-piperidin-l-yl)-hexyloxy]-piperidine-1-sulfonic acid phenylamide | 454 | 4-Hydroxymethyl-piperidine |
| 9.26 | 4-[6-(Cyclopropylmethyl-propyl-amino)-hexyloxy]-piperidine-1-sulfonic acid phenylamide | 452 | Cyclopropylmethyl-propyl-amine |
| 9.27 | 4-[6-(3-Hydroxy-piperidin-1-yl)-hexyloxy]-piperidine-1-sulfonic acid phenylamide | 440 | 3-Hydroxy-piperidine |
| 9.28 | 4-[6-(Cyclohexyl-methyl-amino)-hexyloxy]-piperidine-1-sulfonic acid phenylamide | 452 | Cyclohexyl-methyl-amine |
| 9.29 | 4-[6-(3-Dimethylamino-pyrrolidin-l-yl)-hexyloxy]-piperidine-1-sulfonic acid phenylamide | 453 | 3-Dimethylamine-pyrrolidine |
| 9.30 | 4-(6-Azetidin-1-yl-hexyloxy)-piperidine-1-sulfonic acid phenylamide | 396 | Azetidine |
| 9.31 | 4-[6-(Cyclopropylmethyl-methyl-amino)-hexyloxy]-piperidine-1-sulfonic acid phenylamide | 424 | Cyclopropylmethyl-methyl-amine |

Example 10

Sulfamoyl chlorides were prepared according to the following procedure. 3 equivalents of the corresponding amine were dissolved in $CH_2Cl_2$ (1 ml/mmol) and placed in an ice bath. A solution of chlorosulfonic acid (1 eq.) in $CH_2Cl_2$ (0.5 ml /mmol) was added slowly (30 min). The reaction mixture was stirred at 0° C. for a further 30 min. Afterwards, the ice bath was removed and the stirring was continued for 1 h at room temperature. The precipitate was collected by filtration and dried under high vacuum. This salt was suspended in toluene (1 ml/mmol amine) and $PCl_5$ (1 eq) was added. The mixture was stirred at 75° C. for 2 h, cooled to room temperature and filtered. The solid residue was washed with toluene. The filtrate was evaporated and dried under high vacuum. The crude sulfamoyl chloride was used in the next step without further purification. The following sulfamoyl chlorides were prepared from the corresponding amine:

| Sulfamoylchloride | Amine |
|---|---|
| Benzylsulfamoyl chloride | Benzylamine |
| Phenylsulfamoyl chloride | Aniline |
| 2,4-Difluoro-phenylsulfamoyl chloride | 2,4-Difluoroaniline |
| 2,5-Difluoro-phenylsulfamoyl chloride | 2,5-Difluoroaniline |
| 3,4-Difluoro-phenylsulfamoyl chloride | 3,4-Difluoroaniline |

-continued

| Sulfamoylchloride | Amine |
|---|---|
| 3-Fluoro phenyl-sulfamoyl chloride | 3-Fluoroaniline |
| 4-Fluoro-phenylsulfamoyl chloride | 4-Fluoroaniline |
| 4-Chloro-phenylsulfamoyl chloride | 3-Chloroaniline |
| 4-Bromo-phenylsulfamoyl chloride | 3-Bromoaniline |
| 4-Methyl-phenylsulfamoyl chloride | 4-Methylaniline |
| 4-trifluoromethyl-phenylsulfamoyl chloride | 4-Trifluoromethylaniline |
| 4-Cyano-phenylsulfamoyl chloride | 4-Cyanoaniline |
| 4-Methoxy-phenylsulfamoyl chloride | 4-Methoxyaniline |
| Butylsulfamoyl chloride | Butylamine |
| Phenethylsulfamoyl chloride | Phenethylamine |
| Cyclohexylmethylsulfamoyl chloride | Aminomethylcyclohexane |
| Cyclopropylsulfamoyl chloride | Cyclopropylamine |
| 2,2,2-Trifluoroethylsulfamoyl chloride | 2,2,2-Trifluoroethylamine |
| 4-Fluoro-benzylsulfamoyl chloride | 4-Fluorobenzylamine |
| Furan-2-ylmethylsulfamoyl chloride | Furan-2-ylmethylamine |
| Benzo [1,3]dioxol-5-ylmethylsulfamoyl chloride | Benzo[1,3]dioxol-5-ylmethylamine |

Example 11

Glycine ethyl ester hydrochloride (1 eq.) was dissolved in $CH_3CN$ and placed in an ice bath. Sulfuryl chloride (3 eq.) was added slowly (20 min). The reaction mixture was stirred at room temperature for 15 min and at 65° C. for 20 h. The solvent was evaporated and the residue was dried under high vacuum to yield Chlorosulfonylamino-propionic acid ethyl ester. The crude sulfamoyl chloride was used in the next step without further purification.

Example 12

12.1

A solution of 30 g (130.9 mmol) of Boc-isonipecotic acid in 1.5 1 $CH_2Cl_2$ was treated with 20.42 g (209.3 mmol) of N,O-dimethylhydroxylamine hydrochloride, 23.1 ml (209.3 mmol) of N-methylmorpholine and at 0° C. with 32.6 g (170.1 mmol) of EDCI and 3.53 g (26.2 mmol) of HOBT. The reaction was stirred overnight at room temperature and partitioned between aqueous 10% $KHSO_4/Et_2O$ (3×). The organic phases were washed with aqueous saturated $NaHCO_3$, 10% NaCl and dried over $Na_2SO_4$ to give 37.54 g (quantitative) of 4-(methoxy-methyl-carbamoyl)-piperidine-1-carboxylic acid tert-butyl ester, MS: 273 ($MH^+$).

12.2

A solution of 5.46 g (143.8 mmol) of LAH in 600 ml THF was cooled (−50° C.) and treated during 25 min with a solution of 35.6 g (130.7 mmol) of 4-(Methoxy-methyl-carbamoyl)-piperidine-1-carboxylic acid tert-butyl ester in 600 ml THF. The reaction was warmed up to RT for 3.5 h, cooled (−78° C.) and hydrolyzed with a suspension of 35 g $MgSO_4.7H_2O$, 35 g silicagel in 130 ml aqueous 10% $KHSO_4$. The cooling bath was removed, THF was added, the mixture was stirred for 30 min and filtered. After evaporation, the residue was dissolved in $CH_2Cl_2$, dried ($Na_2SO_4$) and evaporated to give 30.1 g (quantitative) of 4-Formyl-piperidine-1-carboxylic acid tert-butyl ester, MS: 213 (M).

12.3

A solution of 160.86 g (613.3 mmol) of triphenylphosphine in 600 ml $CH_2Cl_2$ was treated with 101.7 g (306.6 mmol) of tetrabromomethane (the reaction heated up to 32° C.) and after 50 min at 20° C., 97.8 ml (705.3 mmol) of triethylamine was added (the reaction heated up to 35° C. and the color became dark violet). After cooling (0° C.), 32.7 g (153.4 mmol) of 4-Formyl-piperidine-1-carboxylic acid tert-butyl ester in 380 ml $CH_2Cl_2$ were added slowly (20 min). The solution was stirred over night at RT, evaporated and filtered through silica gel (deactivated with hexane/$Et_3N$; with hexane and then hexane/ether 4:1 to 1:1) to give 42.54 g (75%) of 4-(2,2-dibromo-vinyl)-piperidine-1-carboxylic acid tert-butyl ester, mp: 82.3–83.9° C., MS: 368 ($MH^+$, 2Br).

12.4

[following conditions described in: Marshall, James A.; Bartley, Gary S.; Wallace, Eli M. Total Synthesis of the Pseudopterane (−)-Kallolide B, the Enantiomer of Natural (+)-Kallolide B. J. Org. Chem. (1996), 61(17), 5729–5735. And Baker, Raymond; Boyes, Alastair L.; Swain, Christopher J. Synthesis of talaromycins A, B, C, and E. J. Chem. Soc., Perkin Trans. 1 (1990), (5), 1415–21.)]

A solution of 6.0 g (16.3 mmol) of 4-(2,2-Dibromo-vinyl)-piperidine-1-carboxylic acid tert-butyl ester in 150 ml THF was treated at −78° C. with 21.4 ml (34.2 mmol) of n-BuLi (ca 1.6 M in hexane). After 2 h at this temperature 4.9 g (16.3 mmol) of paraformaldehyde were added. The reaction was warmed up to RT for 3 h and after 1 h at this temperature partitioned between water/ether (3×). The organic phases were washed with aqueous 10% NaCl, dried over $Na_2SO_4$ and evaporated. Purification by flash-chromatography on silica gel (hexane/EtOAc 4:1) gave 3.34 g (86%) of 4-(3-Hydroxy-prop-1-ynyl)-piperidine-1-carboxylic acid tert-butyl ester, MS: 239 (M).

12.5

A solution of 3.34 g (13.96 mmol) of 4-(3-Hydroxy-prop-1-ynyl)-piperidine-1-carboxylic acid tert-butyl ester in 100 ml $CH_2Cl_2$ was treated at 0° C. with 1.2 ml (15.4 mmol) of methanesulfonylchloride, 1.7 ml (20.93 mmol) of pyridine and 1.71 g (13.96 mmol) of DMAP. The reaction mixture was warmed up to RT for 3 h, treated with water (10 ml) and stirred for 5 min. After extraction with aqueous 10% $KHSO_4/Et_2O$ (3×), the organic phases were washed with aqueous saturated $NaHCO_3$ (2×), aqueous 10% NaCl, dried over $Na_2SO_4$ and evaporated to give 4.05 g (90%) of 4-(3-Methanesulfonyloxy-prop-1-ynyl)-piperidine-1-carboxylic acid tert-butyl ester, MS: 317 (M).

12.6

A solution of 2.96 g (9.4 mmol) of 4-(3-Methanesulfonyloxy-prop-1-ynyl)-piperidine-1-carboxylic acid tert-butyl ester in 50 ml $CH_2Cl_2$ was treated at 0° C. with 25.2 ml of TFA (for 20 min). After 30 min at this temperature, the reaction was evaporated, evaporated again with toluene (4 times) and dried to give 3.6 g (quantitative) of methanesulfonic acid 3-piperidin-4-yl-prop-2-ynyl ester; compound with trifluoro-acetic acid, MS: 218 ($MH^+$).

12.7

A solution of 1.2 g (3.4 mmol) of (Methanesulfonic acid 3-piperidin-4-yl-prop-2-ynyl ester trifluoroacetate in 30 ml $CH_2Cl_2$ was first cooled at 0° C. and then treated with 2.85 ml (16.7 mmol; 5 equivalents) of Hünigsbase and dropwise with 0.56 ml (4.0 mmol) of 4-chlorophenylchloroformate (during 10 min). After 5 min at RT, the mixture was dissolved in aqueous saturated $NaHCO_3$ /$Et_2O$ (3×). The organic phase was dried over $Na_2SO_4$ and evaporation gave 1.6 g crude product of 4-(3-Methanesulfonyloxy-prop-1-ynyl)-piperidine-1-carboxylic acid 4-chloro-phenyl ester, MS: 372 ($MH^+$). The crude product was directly used in the next step.

12.8

In analogy to example 12.7, Methanesulfonic acid 3-piperidin-4-yl-prop-2-ynyl ester; trifluoroacetate and 4-(trifluoromethyl)benzenesulfonylchloride were converted to Methanesulfonic acid 3-[1-(4-trifluoromethyl-benzenesulfonyl)-piperidin-4-yl]-prop-2-ynyl ester, MS: 425 (M).

12.9

In analogy to example 12.7, Methanesulfonic acid 3-piperidin-4-yl-prop-2-ynyl ester; trifluoroacetate and 4-chlorobenzoylchloride were converted to Methane-sulfonic acid 4-[1-(4-chloro-benzoyl)-piperidin-4-yl]-prop-3-ynyl ester, MS: 356 ($MH^+$, 1Cl).

Example 13

13.1

A solution of 320 mg (0.83 mmol) of 4-(3-Methanesulfonyloxy-prop-1-ynyl)-piperidine-1-carboxylic acid 4-chloro-phenyl ester and 0.79 ml (8.3mmol) of N-methylallylamine in 7 ml of methanol was stirred over night at RT. Then an aqueous solution of 1N NaOH was added and extracted with ether (3×). The organic phase was dried with $Na_2SO_4$, filtered and evaporated. The residue was purified by flash column chromatography on silica gel ($CH_2Cl_2$/MeOH 19:1 to 9:1) to yield 201 mg (70%) of pure 4-[3-(Allyl-methyl-amino)-prop 1 ynyl]-piperidine-1-carboxylic acid 4-chloro-phenyl ester, MS: 347 ($MH^+$, 1Cl).

13.2

In analogy to example 13.1; and for completion, the reaction was heated at reflux for 1 min, 4-(3-Methanesulfonyloxy-prop-1-ynyl)-piperidine-1-carboxylic acid 4-chloro-phenyl ester and N-methylpropylamine were converted to 4-[3-(Methyl-propyl-amino)-prop-1-ynyl]-piperidine-1-carboxylic acid 4-chloro-phenyl ester, MS: 349 ($MH^+$, 1Cl).

13.3

In analogy to example 13.1; and for completion, the reaction was heated at reflux for 30 min, 4-(3-Methanesulfonyloxy-prop-1-ynyl)-piperidine-1-carboxylic acid 4-chloro-phenyl ester and N-ethylaminoethanol were converted to 4-{3-[Ethyl-(2-hydroxy-ethyl) amino]-prop-1-ynyl}-piperidine-1-carboxylic acid 4-chloro-phenyl ester, MS: 365 ($MH^+$, 1Cl).

13.4

In analogy to example 13.1, Methanesulfonic acid 3-[1-(4-trifluoromethyl-benzenesulfonyl)-piperidin-4-yl]-prop-2-ynyl ester and N-ethylaminoethanol were converted to 2-(Ethyl-{3-[1-(4-trifluoromethyl-benzenesulfonyl)-piperidin-4-yl]-prop-2-ynyl}-amino)-ethanol, mp: 87.4–89.4° C., MS: 419 ($MH^+$).

13.5

In analogy to example 13.1, Methanesulfonic acid 3-[1-(4-trifluoromethyl-benzenesulfonyl)-piperidin-4-yl]-prop-2-ynyl ester and N-methylpropylamine were converted to Methyl-propyl-{3-[1-(4-trifluoromethyl-benzenesulfonyl)-piperidin-4-yl]-prop-2-ynyl}-amine, mp: 65.0–66.2° C., MS: 403 ($MH^+$).

13.6

In analogy to example 13.1, Methanesulfonic acid 3-[1-(4-trifluoromethyl-benzenesulfonyl)-piperidin-4-yl]-prop-2-ynyl ester and N-methylallylamine were converted to Allyl-methyl-{3-[1-(4-trifluoromethyl-benzenesulfonyl)-piperidin-4-yl]-prop-2-ynyl}-amine, mp: 65.8–66.9 MS: 401 ($MH^+$).

13.7

In analogy to example 13.1, Methanesulfonic acid 4-[1-(4-chloro-benzoyl)-piperidin-4-yl]-prop-3-ynyl ester and N-methylallylamine were converted to {4-[3-(Allyl-methyl-amino)-prop-1-ynyl]-piperidin-1-yl}-(4-chloro-phenyl)-methanone, MS: 331 ($MH^+$, 1Cl).

13.8

In analogy to example 13.1, Methanesulfonic acid 4-[1-(4-chloro-benzoyl)-piperidin-4-yl]-prop-3-ynyl ester and N-methylpropylamine were converted to (4-Chloro-phenyl)-{4-[3-(methyl-propyl-amino)-prop-1-ynyl]-piperidin-1-yl}-methanone, MS: 333 ($MH^1$, 1Cl).

13.9

In analogy to example 13.1, Methanesulfonic acid 4-[1-(4-chloro-benzoyl)-piperidin-4-yl]-prop-3-ynyl ester and N-ethylaminoethanol were converted to (4-Chloro-phenyl)-(4-{3-[ethyl-(2-hydroxy-ethyl)-amino]-prop-1-ynyl}-piperidin-1-yl)-methanone, MS: 349 ($MH^+$, 1Cl).

Example 14

14.1

A solution of 12.0 g (32.5 mmol) of 4-(2,2-Dibromo-vinyl)-piperidine-1-carboxylic acid tert-butyl ester in 500 ml THF was treated at −78° C. with 42.7 ml (68.3 mmol) of n-BuLi (ca 1.6 M in hexane) and stirred for 2 h, then 36 ml (297.5 mmol) of DMPU were added and 10 min later 24.6 ml (162.6 mmol) of 2-(2-bromoethoxy)tetrahydro-2H-pyran were dropped in during 20 min. The reaction was warmed up to RT and stirred over night. An aqueous solution of saturated $NH_4Cl$ was added and the mixture was extracted with ether (3×). The organic phase was washed with $H_2O$ (2×), aqueous 10% NaCl and dried with $Na_2SO_4$, filtered and evaporated to give after flash column chromatography on silica gel (first eluted with hexane alone, then hexane/EtOAc 49:1 to 4:1) 4.5 g (40%) of 4-[4-(Tetrahydro-pyran-2-yloxy)-but-1-ynyl]-piperidine-1-carboxylic acid tert-butyl ester, MS: 338 ($MH^+$).

14.2

A solution of 4.5 g (13.4 mmol) of 4-[4-(Tetrahydro-pyran-2-yloxy)-but-1-ynyl]-piperidine-1-carboxylic acid tert-butyl ester and 1 g (4mmol) of pyrimidium toluene-4-sulfonate in 45 ml MeOH was stirred at 55° C. for 1 h. The reaction was partitioned between aqueous solution of 10% $KHSO_4$ /ether (3×). The organic phases were washed with aqueous saturated $NaHCO_3$, 10% NaCl, dried over $Na_2SO_4$ and evaporated to give 3.26 g (97%) of 4-(4-Hydroxy-but-1-ynyl)-piperidine-1-carboxylic acid tert-butyl ester, MS: 254 ($MH^+$).

14.3

In analogy to example 12.5, 4-(4-Hydroxy-but-1-ynyl)-piperidine-1-carboxylic acid tert-butyl ester was converted to 4-(4-Methanesulfonyloxy-but-1-ynyl)-piperidine-1-carboxylic acid tert-butyl ester, MS: 331 (M)

14.4

In analogy to example 12.6, 4-(4-Methanesulfonyloxy-but-1-ynyl)-piperidine-1-carboxylic acid tert-butyl ester was converted to Methanesulfonic acid 4-piperidin-4-yl-but-3-ynyl ester trifluoroacetate, MS: 231 (M)

14.5

In analogy to example 12.7, Methanesulfonic acid 4-piperidin-4-yl-but-3-ynyl ester trifluoroacetate and 4-chlorophenylchloroformate were converted to 4-(4-Methanesulfonyloxy-but-1-ynyl)-piperidine-1-carboxylic acid 4-chloro-phenyl ester, MS: 386 ($MH^+$, 1Cl)

14.6

In analogy to example 12.7, Methanesulfonic acid 4-piperidin-4-yl-but-3-ynyl ester trifluoroacetate and 4-(trifluoromethyl)benzenesulfonylchloride were converted to Methanesulfonic acid 4-[1-(4-trifluoromethyl-benzenesulfonyl)-piperidin-4-yl]-but-3-ynyl ester, MS: 440 ($MH^+$)

14.7

In analogy to example 12.7, Methanesulfonic acid 4-piperidin-4-yl-but-3-ynyl ester trifluoroacetate and 4-chlorobenzoylchloride were converted to Methane-sulfonic acid 4-[1-(4-chloro-benzoyl)-piperidin-4-yl]-but-3-ynyl ester, MS: 370 ($MH^+$, 1Cl)

Example 15

15.1

In analogy to example 13.1 (the reaction was heated at reflux for 5 h), 4-(4-Methanesulfonyloxy-but-1-ynyl)-piperidine-1-carboxylic acid 4- chloro-phenyl ester and N-methylallylamine were converted to 4-[4-(Allyl-methyl-amino)-but-1-ynyl]-piperidine-1-carboxylic acid 4-chloro-phenyl ester, MS: 361 ($MH^+$, 1Cl)

15.2

In analogy to example 13.1 (the reaction was heated at reflux for 4 h), 4-(4-Methanesulfonyloxy-but-1-ynyl)-piperidine-1-carboxylic acid 4-chloro-phenyl ester and N-methylpropylamine were converted to 4-[4-(Methyl-propyl-amino)-but-1-ynyl]-piperidine-1-carboxylic acid 4-chloro-phenyl ester, MS: 363 ($MH^+$, 1Cl)

15.3

In analogy to example 13.1 (the reaction was heated at reflux for 4 h), 4-(4-Methanesulfonyloxy-but-1-ynyl)-piperidine-1-carboxylic acid 4-chloro-phenyl ester and N-ethylaminoethanol were converted to 4-{4-[Ethyl-(2-hydroxy-ethyl)-amino]-but-1-ynyl}-piperidine-1-carboxylic acid 4-chloro-phenyl ester, MS: 379 ($MH^+$, 1Cl)

15.4

In analogy to example 13.1 (the reaction was heated at reflux for 14 h), 4-(4-Methanesulfonyloxy-but-1-ynyl)-piperidine-1-carboxylic acid 4-chloro-phenyl ester and N-(methoxyethyl)ethylamine were converted to 4-{4-[Ethyl-(2-methoxy-ethyl)-amino]-but-1-ynyl}-piperidine-1-carboxylic acid 4-chloro-phenyl ester, MS: 393 ($MH^+$, 1Cl).

15.5

In analogy to example 13.1 (the reaction was heated at reflux for 4 h), Methanesulfonic acid 4-[1-(4-trifluoromethyl-benzenesulfonyl)-piperidin-4-yl]-but-3-ynyl ester and N-methylallylamine were converted to Allyl-methyl-{4-[1-(4-trifluoromethyl-benzenesulfonyl)-piperidin-4-yl]-but-3-ynyl}-amine, mp: 65.0–66.2° C., MS: 415 ($MH^+$)

15.6

In analogy to example 13.1 (the reaction was heated at reflux for 7 h), Methanesulfonic acid 4-[1-(4-trifluoromethyl-benzenesulfonyl)-piperidin-4-yl]-but-3-ynyl ester and N-methylpropylamine were converted to Methyl-propyl-{4-[1-(4-trifluoromethyl-benzenesulfonyl)-piperidin-4-yl]-but-3-ynyl}-amine, mp: 60.5–62.0° C., MS: 417 ($MH^+$).

15.7

In analogy to example 13.1 (the reaction was heated at reflux for 8 h), Methanesulfonic acid 4-[1-(4-trifluoromethyl-benzenesulfonyl)-piperidin-4-yl]-but-3-ynyl ester and N-ethylaminoethanol were converted to 2-(Ethyl-{4-[1-(4-trifluoromethyl-benzenesulfonyl)-piperidin-4-yl]-but-3-ynyl}-amino)-ethanol, mp: 73.2–74.3° C. MS: 433 ($MH^+$).

15.8

In analogy to example 13.1 (the reaction was heated at reflux for 7 h and kept one night at RT), Methanesulfonic acid 4-[1-(4-trifluoromethyl-benzenesulfonyl)-piperidin-4-yl]-but-3-ynyl ester and N-(methoxyethyl)ethylamine were converted to Ethyl-(2-methoxy-ethyl)-{4-[1-(4-trifluoromethyl-benzenesulfonyl)-piperidin-4-yl]-but-3-ynyl}-amine, MS: 447 ($MH^+$).

15.9

In analogy to example 13.1 (the reaction was heated at reflux for 5 h), Methanesulfonic acid 4-[1-(4-chloro-benzoyl)-piperidin-4-yl]-but-3-ynyl ester and N-methylallylamine were converted to {4-[4-(Allyl-methyl-amino)-but-1-ynyl]-piperidin-1-yl}-(4-chloro-phenyl)-methanone, MS: 345 ($MH^+$, 1Cl).

15.10

In analogy to example 13.1 (the reaction was heated at reflux for 5 h), Methanesulfonic acid 4-[1-(4-chloro-benzoyl)-piperidin-4-yl]-but-3-ynyl ester and N-methylpropylamine were converted to (4-Chloro-phenyl)-{4-[4-methyl-propyl-amino)-but-1-ynyl]-piperidin-1-yl}-methanone, MS: 347 ($MH^+$, 1Cl).

15.11

In analogy to example 13.1 (the reaction was heated at reflux for 5 h), Methanesulfonic acid 4-[1-(4-chloro-benzoyl)-piperidin-4-yl]-but-3-ynyl ester and N-ethylaminoethanol were converted to (4-Chloro-phenyl)-(4-{4-[ethyl-(2-hydroxy-ethyl)-amino ]-but-1-ynyl}-piperidin-1-yl)-methanone, MS: 363 ($MH^+$, 1Cl).

15.12

In analogy to example 13.1 (the reaction was heated at reflux for 11 h), Methanesulfonic acid 4-[1-(4-chloro-benzoyl)-piperidin-4-yl]-but-3-ynyl ester and N-(methoxyethyl)ethylamine were converted to (4-Chloro-phenyl)-(4-{4-[ethyl-(2-methoxy-ethyl)-amino]-but-1-ynyl}-piperidin-1-yl)-methanone, MS: 377 ($MH^+$,1Cl).

Example 16

16.1

In analogy to example 2.1, 4-(2,2-Dibromo-vinyl)-piperidine-1-carboxylic acid tert-butyl ester and n-BuLi with DMPU and 1-chloro-3-iodopropane were converted to 4-(5-Chloro-pent-1-ynyl)-piperidine-1-carboxylic acid tert-butyl ester, MS: 286 ($MH^1$, 1Cl). No purification, crude product was used directly for the next step.

16.2

A solution of 14.6 g (16.3 mmol) of the crude 4-(5-Chloro-pent-1-ynyl)-piperidine-1-carboxylic acid tert-butyl ester in 44 ml $CH_2Cl_2$ was treated with 44 ml of TFA at 0° C. (for 20 min). The reaction was evaporated and partitioned between aqueous 10% $KHSO_4/Et_2O$ (3×). The aqueous phase was adjusted to pH>10 by adding 1N NaOH and extracted with EtOAc (3×) The organic phase was dried over $Na_2SO_4$ and evaporated to give 1.41 g (50% over two steps) of 4-(5-Chloro-pent-1-ynyl)-piperidine, MS: 186 ($MH^+$, 1Cl).

16.3

In analogy to example 12.7, 4-(5-Chloro-pent-1-ynyl)-piperidine and 4-chlorophenylchloroformate were converted to 4-(5-Chloro-pent-1-ynyl)-piperidine-1-carboxylic acid 4-chloro-phenyl ester, MS: 340 (M, 1Cl).

16.4

In analogy to example 12.7,4-(5-Chloro-pent-1-ynyl)-piperidine and 4-(trifluoromethyl)benzenesulfonylchloride were converted to 4-(5-Chloro-pent-1-ynyl)-1-(4-trifluoromethyl-benzenesulfonyl)-piperidine, MS: 393 (M).

16.5

In analogy to example 12.7, 4-(5-Chloro-pent-1-ynyl)-piperidine and 4-chlorobenzoylchloride were converted to [4-(5-Chloro-pent-1-ynyl)-piperidin-1-yl]-(4-chloro-phenyl)-methanone, MS: 324 (M).

Example 17

17.1

A solution of 733 mg (2.15 mmol) of 4-(5-Chloro-pent-1-ynyl)-piperidine-1-carboxylic acid 4-chloro-phenyl ester in 20 ml butan-2-one was treated with 650 mg of NaI (4.3 mmol) and heated at 80° C. for 48 h. Evaporation gave crude 4-(5-Iodo-pent-1-ynyl)-piperidine-1-carboxylic acid 4-chloro-phenyl ester, which was used directly for the next step, MS: 431 (M, 1Cl).

300 mg (corresponds to 0.7 mmol) of crude 4-(5-Iodo-pent-1-ynyl)-piperidine-1-carboxylic acid 4-chloro-phenyl ester in 5 ml MeOH was treated with 0.7 ml (6.95 mmol) of N-methylallylamine (at 0° C.). The reaction was stirred overnight at room temperature and partitioned between aqueous 1N NaOH /ether (3×), the organic phases were dried ($Na_2SO_4$) and evaporated. Purification by flash-chromatography on silica gel ($CH_2Cl_2$/MeOH 19:1) gave 116 mg (44% over two steps) of 4-[5-(Allyl-methyl-amino)-pent-1-ynyl]-piperidine-1-carboxylic acid 4-chloro-phenyl ester, MS: 375 ($MH^+$, 1Cl).

17.2

In analogy to example 17.1, 4-(5-Chloro-pent-1-ynyl)-piperidine-1-carboxylic acid 4-chloro-phenyl ester and N-methylpropylamine were converted to 4-[5-(Methyl-propyl-amino)-pent-1-ynyl]-piperidine-1-carboxylic acid 4-chloro-phenyl ester, MS: 377 ($MH^+$, 1Cl).

17.3

In analogy to example 17.1 (the reaction was heated at reflux for 1 h), 4-(5-Chloro-pent-1-ynyl)-piperidine-1-carboxylic acid 4-chloro-phenyl ester and N-ethylaminoethanol were converted to 4-{5-[Ethyl-(2-hydroxy-ethyl)-amino]-pent-1-ynyl}-piperidine-1-carboxylic acid 4-chloro-phenyl ester, MS: 393 ($MH^+$, 1Cl).

17.4

In analogy to example 17.1 (the reaction was heated at reflux for 16 h), 4-(5-Chloro-pent-1-ynyl)-1-(4-trifluoromethyl-benzenesulfonyl)-piperidine and N-methylallylamine were converted to Allyl-methyl-{5-[1-(4-trifluoromethyl-benzenesulfonyl)-piperidin-4-yl]-pent-4-ynyl}-amine, mp: 64.5–65.5° C., MS: 429 ($MH^+$).

17.5

In analogy to example 17.1 (the reaction was heated at reflux for 16 h), 4-(5-Chloro-pent-1-ynyl)-1-(4-trifluoromethyl-benzenesulfonyl)-piperidine and N-methylpropylamine were converted to Methyl-propyl-{5-[1-(4-trifluoromethyl-benzenesulfonyl)-piperidin-4-yl]-pent-4-ynyl}-amine, mp: 57.7–58.8° C.,MS: 431 ($MH^+$).

17.6

In analogy to example 17.1 (the reaction was heated at reflux for 16 h), 4-(5-Chloro-pent-1-ynyl)-1-(4-trifluoromethyl-benzenesulfonyl)-piperidine and N-ethylaminoethanol were converted to 2-(Ethyl-{5-[1-(4-trifluoromethyl-benzenesulfonyl)-piperidin-4-yl]-pent-4-ynyl}-amino)-ethanol, mp: 79.8–81.0° C., MS: 447 ($MH^+$).

17.7

In analogy to example 17.1 (the reaction was heated at reflux for 6 h), [4-(5-Chloro-pent-1-ynyl)-piperidin-1-yl]-(4-chloro-phenyl)-methanone and N-methylpropylamine were converted to (4-Chloro-phenyl)-{4-[5-(methyl-propyl-amino)-pent-1-ynyl]-piperidin-1-yl}-methanone, MS: 361 ($MH^+$, 1Cl).

Example 18

18.1

A suspension of 50 mg (0.14 mmol) of 4-{3-[Ethyl-(2-hydroxy-ethyl)-amino]-prop-1ynyl}-piperidine-1-carboxylic acid 4-chloro-phenyl ester with 5 mg of Pt/C(5%) in 4 ml toluene was hydrogenated (1 atm) during 12 h. The reaction was filtered over glass filter and evaporated. Flash column chromatography on silica gel ($CH_2Cl_2$/MeOH 19:1 to 9:1) gave 19 mg (24%) of pure 2-(Ethyl-{3-[1-(4-trifluoromethyl-benzenesulfonyl)-piperidin-4-yl]-propyl}-amino)-ethanol, MS: 423 ($MH^+$).

18.2

In analogy to example 18.1, Methyl-propyl-{3-[1-(4-trifluoromethyl-benzenesulfonyl)-piperidin-4-yl]-prop-2-ynyl}-amine was converted to Methyl-propyl-{3-[1-(4-trifluoromethyl-benzenesulfonyl)-piperidin-4-yl]-propyl}-amine, mp: 71.3-72.7° C. MS: 407 ($MH^+$).

18.3

In analogyto example 18.1, 4-{3-[Ethyl-(2-hydroxy-ethyl)-amino]-prop-1-ynyl}-piperidine-1-carboxylic acid 4-chloro-phenyl ester was converted to 4-{3-[Ethyl-(2-hydroxy-ethyl)-amino]-propyl}-piperidine-1-carboxylic acid 4-chloro-phenyl ester, MS: 369 ($MH^+$,1Cl).

18.4

In analogy to example 18.1, 4-[3-(Methyl-propyl-amino)-prop-1-ynyl]-piperidine-1-carboxylic acid 4-chloro-phenyl ester was converted to 4-[3-(Methyl-propyl-amino)-propyl]-piperidine-1-carboxylic acid 4-chloro-phenyl ester, MS: 353 ($MH^+$,1Cl).

Example 19

19.1

1.63 g (6.83 mmol) of 4-(3-Hydroxy-prop-1-ynyl)-piperidine-1-carboxylic acid tert-butyl ester was dissolved in 50 ml of ethanol, treated with 350 mg of $PtO_2.H_2O$ and hydrogenated (1 atm) for 7 h. The reaction was filtered and evaporated to give 1.65 g (99%) of 4-(3-Hydroxy-propyl)-piperidine-1-carboxylic acid tert-butyl ester, MS: 244 ($MH^1$, 1Cl).

19.2

In analogy to example 12.5, 4-(3-Hydroxy-propyl)-piperidine-1-carboxylic acid tert-butyl ester was converted to 4-(3-Methanesulfonyloxy-propyl)-piperidine-1-carboxylic acid tert-butyl ester, MS: 321 (M).

19.3

In analogy to example 12.6, 4-(3-Methanesulfonyloxy-propyl)-piperidine-1-carboxylic acid tert-butyl ester was converted to Methanesulfonic acid 3-piperidin-4-yl-propyl ester trifluoroacetate, MS: 222 ($MH^+$).

19.4

In analogy to example 12.7, Methanesulfonic acid 3-piperidin-4-yl-propyl ester trifluoroacetate and 4-chlorobenzoylchloride were converted to Methanesulfonic acid 3-[1-(4-chloro-benzoyl)-piperidin-4-yl]-propyl ester, MS: 360 ($MH^+$, 1Cl).

19.5

In analogy to example 12.7, Methanesulfonic acid 3-piperidin-4-yl-propyl ester trifluoroacetate and 4-trifluoromethylbenzoylchloride were converted to Methanesulfonic acid 3-[1-(4-trifluoromethyl-benzoyl)-piperidin-4-yl]-propyl ester, MS: 394 ($MH^1$).

Example 20

20.1

A suspension of 83 mg (0.198 mmol) of Methyl-propyl-{4-[1-(4-trifluoromethyl-benzenesulfonyl)-piperidin-4-yl]-but-3-ynyl}-amine in 4 ml EtOH and 8 mg of $PtO_2.H_2O$ was hydrogenated (1 atm) for 7 h. The reaction was filtered and evaporated. Flash column chromatography on silica gel ($CH_2Cl_2$/MeOH 19:1 to 9:1) gave 78 mg (93%) of Methyl-propyl-{4-[1-(4-trifluoromethyl-benzenesulfonyl)-piperidin-4-yl]-butyl}-amine, mp: 73.0–74.8° C., MS: 421 ($MH^+$).

20.2

In analogy to example 20.1, 2-(Ethyl-{4-[1-(4-trifluoromethyl-benzenesulfonyl)-piperidin-4-yl]-but-3-ynyl}-amino)-ethanol was converted to 2-(Ethyl-{4-[1-(4-trifluoromethyl-benzenesulfonyl)-piperidin-4-yl]-butyl}-amino)-ethanol, MS: 437 ($MH^+$)

20.3

In analogy to example 20.1, 4-[5-(Methyl-propyl-amino)-pent-1-ynyl]-piperidine-1-carboxylic acid 4-chloro-phenyl ester was converted to 4-[5-(Methyl-propyl-amino)-pentyl]-piperidine-1-carboxylic acid 4-chloro-phenyl ester, MS: 381 ($MH^+$, 1Cl).

20.4

In analogy to example 20.1, 4-{5-[Ethyl-(2-hydroxy-ethyl)-amino]-pent-1-ynyl}-piperidine-1-carboxylic acid 4-chloro-phenyl ester was converted to 4-{5-[Ethyl-(2-hydroxy-ethyl)-amino]-pentyl}-piperidine-1-carboxylic acid 4-chloro-phenyl ester, MS: 397 ($MH^+$, 1Cl).

Example A

Tablets containing the following ingredients can be manufactured in a conventional manner:

| Ingredients | Per tablet |
|---|---|
| Compound of formula I | 10.0–100.0 mg |
| Lactose | 125.0 mg |
| Maize starch | 75.0 mg |
| Talc | 4.0 mg |
| Magnesium stearate | 1.0 mg |

Example B

Capsules containing the following ingredients can be manufactured in a conventional manner:

| Ingredients | Per capsule |
|---|---|
| Compound of formula I | 25.0 mg |
| Lactose | 150.0 mg |
| Maize starch | 20.0 mg |
| Talc | 5.0 mg |

Example C

Injection solutions can have the following composition:

| | | |
|---|---|---|
| Compound of formula I | 3.0 | mg |
| Gelatine | 150.0 | mg |
| Phenol | 4.7 | mg |
| Water for injection solutions | ad 1.0 | ml |

What is claimed is:

1. A compound of formula (I)

(I)

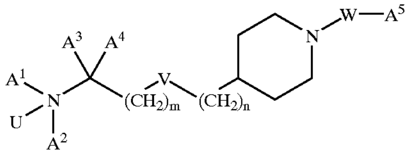

wherein

U is a lone pair;

V is —C≡C—;

m and n are each integers from 0 to 7 and m+n is 0 to 7;

W is $SO_2$, or $SO_2NR^1$, $A^1$ is H, lower-alkyl or lower-alkenyl, $A^2$ is cycloalkyl, cycloalkyl-lower-alkyl, lower-alkenyl, lower-alkynyl or lower-alkyl optionally substituted with hydroxy, lower-alkoxy or lower-alkoxy-carbonyl, or $A^1$ and $A^2$ bond together to form —$A^1$—$A^2$—, wherein —$A^1$—$A^2$— is lower-alkylene or lower-alkenylene, optionally substituted by $R^2$, and one —$CH_2$— group of —$A^1$—$A^2$— is optionally replaced by $NR^3$, S, or O;

$A^3$ and $A^4$ are independently hydrogen or lower-alkyl;

$A^5$ is lower-alkyl optionally substituted with halogen, lower-alkenyl, lower-alkoxy-carbonyl-lower-alkyl, cycloalkyl, cycloalkyl-lower-alkyl, aryl, aryl-lower-alkyl, heteroaryl, or heteroaryl-lower-alkyl;

$R^2$ is lower-alkyl, hydroxy, hydroxy-lower-alkyl, or $N(R^4, R^5)$;

$R^1$, $R^3$, $R^4$ and $R^5$ are independently hydrogen or lower-alkyl; and

When $A^1$ is not bonded to $A^2$, $A^1$ and $A^3$ optionally bond together to form —$A^1$—$A^3$—, wherein —$A^1$—$A^3$— is lower-alkylene or lower-alkenylene, optionally substituted by $R^2$, and one —$CH_2$—group of —$A^1$—$A^3$— is optionally replaced by $NR^3$, S, or O; or pharmaceutically acceptable esters of the compounds of formula (I).

2. A compound of formula (I)

(I)

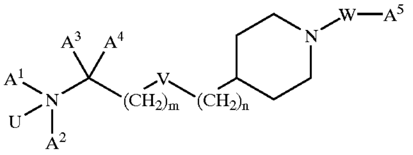

wherein

U is a lone pair;

V is —$CH_2$—;

m and n are each integers from 0 to 7 and m+n is 0 to 7;

W is $SO_2$, or $SO_2NR^1$, $A^1$ is H, lower-alkyl or lower-alkenyl, $A^2$ is cycloalkyl, cycloalkyl-lower-alkyl, lower-alkenyl, lower-alkynyl or lower-alkyl optionally substituted with hydroxy, lower-alkoxy or lower-alkoxy-carbonyl, or $A^1$ and $A^2$ bond together to form —$A^1$—$A^2$—, wherein —$A^1$—$A^2$— is lower-alkylene or lower-alkenylene, optionally substituted by $R^2$, and one —$CH_2$—, group of —$A^1$—$A^2$— is optionally replaced by $NR^3$, S, or O;

$A^3$ and $A^4$ are independently hydrogen or lower-alkyl;

$A^5$ is lower-alkyl optionally substituted with halogen, lower-alkenyl, lower-alkoxy-carbonyl-lower-alkyl, cycloalkyl, cycloalkyl-lower-alkyl, aryl, aryl-lower-alkyl, heteroaryl, or heteroaryl-lower-alkyl;

$R^2$ is lower-alkyl, hydroxy, hydroxy-lower-alkyl, or $N(R^4, R^5)$;

$R^1$, $R^3$, $R^4$ and $R^5$ are independently hydrogen or lower-alkyl; and

When $A^1$ is not bonded to $A^2$, $A^1$ and $A^3$ optionally bond together to form —-$A^1$—$A^3$—, wherein —$A^1$—$A^3$— is lower-alkylene or lower-alkenylene, optionally substituted by $R^2$, and one —$CH_2$— group of —$A^1$—$A^3$— is optionally replaced by $NR^3$, S, or O; or pharmaceutically acceptable salts or esters of the compounds of formula (I).

3. A compound of formula (I)

(I)

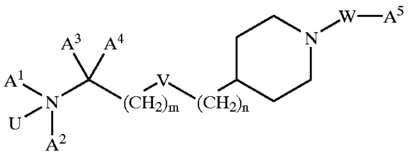

wherein

U is a lone pair;

V is O, —$CH_2$—, —CH═CH—, or —C≡C—;

m and n are each integers from 0 to 7 and m+n is 0 to 7;

W is $SO_2NH$, with the provisos that:

a) m is 1 to 7 when V is O, $A^1$ is H, lower-alkyl or lower-alkenyl, $A^2$ is cycloalkyl, cycloalkyl-lower-alkyl, lower-alkenyl, lower-alkynyl or lower-alkyl optionally substituted with hydroxy, lower-alkoxy or lower-alkoxy-carbonyl, or $A^1$ and $A^2$ bond together to form —$A^1$—$A^2$—, wherein —$A^1$—$A^2$— is lower-alkylene or lower-alkenylene, optionally substituted by $R^2$, and one $—CH_2—$ group of $—A^1—A^2—$ is optionally replaced by $NR^3$, S, or O;

$A^3$ and $A^4$ are independently hydrogen or lower-alkyl;

$A^5$ is lower-alkyl optionally substituted with halogen, lower-alkenyl, lower-alkoxy-carbonyl-lower-alkyl, cycloalkyl, cycloalkyl-lower-alkyl, aryl, aryl-lower-alkyl, heteroaryl, or heteroaryl-lower-alkyl;

$R^2$ is lower-alkyl, hydroxy, hydroxy-lower-alkyl, or $N(R^4, R^5)$;

$R^1$, $R^3$, $R^4$ and $R^5$ are independently hydrogen or lower-alkyl; and

When $A^1$ is not bonded to $A^2$, $A^1$ and $A^3$ optionally bond together to form $—A^1—A^3—$, wherein $—A^1—A^3—$ is lower-alkylene or lower-alkenylene, optionally substituted by $R^2$, and one $—CH_2—$ group of $—A^1—A^3—$ is optionally replaced by $NR^3$, S, or O; or pharmaceutically acceptable salts or esters of the compounds of formula (I).

4. A compound of formula (I)

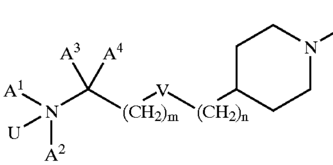

(I)

wherein

U is a lone pair;

V is O, $—CH_2—$, $—CH{=}CH—$, or $—C{\equiv}C—$;

m is an integer from 0 to 2;

n is an integer from 0 to 7;

m+n is 0 to 7;

W is $SO_2$, or $SO_2NR^1$, with the provisos that:

a) m+n is 1 or 2 when V is $—CH_2—$ and W is $SO_2$, b) m=n=0 when V is $—CH{=}CH—$ and W is $SO_2$, c) m is 1 to 2 when V is O, and d) m is 1 to 2 when V is O, W is $SO_2$, and n is 0;

$A^1$ is H, lower-alkyl or lower-alkenyl, $A^2$ is cycloalkyl, cycloalkyl-lower-alkyl, lower-alkenyl, lower-alkynyl or lower-alkyl optionally substituted with hydroxy, lower-alkoxy or lower-alkoxy-carbonyl, or $A^1$ and $A^2$ bond together to form $—A^1—A^2—$, wherein $—A^1—A^2—$ is lower-alkylene or lower-alkenylene, optionally substituted by $R^2$, and one $—CH_2—$ group of $—A^1—A^2—$ is optionally replaced by $NR^3$, S, or O;

$A^3$ and $A^4$ are independently hydrogen or lower-alkyl;

$A^5$ is lower-alkyl optionally substituted with halogen, lower-alkenyl, lower-alkoxy-carbonyl-lower-alkyl, cycloalkyl, cycloalkyl-lower-alkyl, aryl, aryl-lower-alkyl, heteroaryl, or heteroaryl-lower-alkyl;

$R^2$ is lower-alkyl, hydroxy, hydroxy-lower-alkyl, or $N(R^4, R^5)$;

$R^1$, $R^3$, $R^4$ and $R^5$ are independently hydrogen or lower-alkyl; and

When $A^1$ is not bonded to $A^2$, $A^1$ and $A^3$ optionally bond together to form $—A^1—A^3—$, wherein $—A^1—A^3—$ is lower-alkylene or lower-alkenylene, optionally substituted by $R^2$, and one $—CH_2—$ group of $—A^1—A^3—$ is optionally replaced by $NR^3$, S, or O; or pharmaceutically acceptable salts or esters of the compounds of formula (I).

5. A compound of formula (I)

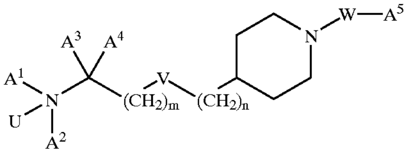

(I)

wherein

U is a lone pair;

V is O, $—CH_2—$, $—CH{=}CH—$, or $—C{\equiv}C—$;

m and n are each integers from 0 to 7 and m+n is 0 to 7;

W is $SO_2$, or $SO_2NR^1$,with the provisos that:

a) m+n is 1 or 2 when V is $—CH_2—$ and W is $SO_2$, b) m=n0 when V is $—CH{=}CH—$ and W is $SO_2$, c) m is 1 to 7 when V is O, and d) m is 1 to 3 when V is O, W is $SO_2$, and n is 0;

$A^1$ and $A^2$ are bonded together to form $—A^1—A^2—$, wherein $—A^1—A^2—$ is lower-alkylene or lower-alkenylene. optionally substituted by $R^2$, and one $—CH_2—$ group of $—A^1—A^2—$ is optionally replaced by $NR^3$, S, or O, $A^3$ and $A^4$ are independently hydrogen or lower-alkyl;

$A^5$ is lower-alkyl optionally substituted with halogen, lower-alkenyl, lower-alkoxy-carbonyl-lower-alkyl, cycloalkyl, cycloalkyl-lower-alkyl, aryl, aryl-lower-alkyl, heteroaryl, or heteroaryl-lower-alkyl;

$R^2$ is lower-alkyl, hydroxy, hydroxy-lower-alkyl, or $N(\text{lower-alkyl})_2$, and $R^3$ is lower-alkyl; or pharmaceutically acceptable salts or esters of the compounds of formula (I).

6. The compound according to claim 5, wherein $R^2$ is methyl, hydroxy, 2-hydroxy-ethyl, or $N(CH_3)_2$, and $R^3$ is methyl.

7. A compound of formula (Ia)

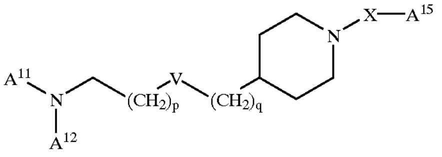

(Ia)

wherein

V is O, $—CH_2—$, $—CH{=}CH—$, or $—C{\equiv}C—$;

p is an integer from 0 to 5;

q 0, 1 or 2;

X is $SO_2NH$, with the proviso that:

a) p is 1 to 5 when V is O $A^{11}$ is methyl or ethyl;

$A^{12}$ is cyclopropyl, lower-alkenyl, or lower-alkyl optionally substituted with hydroxy or lower-alkoxy; and $A^{15}$ is lower-alkyl optionally substituted with halogen, lower-alkenyl, lower-alkoxy-carbonyl-lower-alkyl, cycloalkyl, cycloalkyl-lower-alkyl, aryl, aryl-lower-alkyl, heteroaryl, or heteroaryl-lower-alkyl; or pharmaceutically acceptable salts or esters of the compounds of formula (Ia).

8. The compound of claim 7, wherein $A^{15}$ is lower alkyl.

9. A compound selected from the group consisting of 4-[6-(allyl-methyl-amino)-hexyloxy]-piperidine-1-sulfonic acid butylamide and pharmaceutically acceptable salts thereof.

10. The compound of claim 7, wherein $A^{15}$ is cycloalkyl-loweralkyl.

11. A compound selected from the group consisting of 4-[6-(allyl-methyl-amino)-hexyloxy]-piperidine-1-sulfonic acid cyclohexylmethyl-amide, and pharmaceutically acceptable salts thereof.

12. The compound of claim 7, wherein $A^{15}$ is phenyl.

13. A compound selected from the group consisting of 4-[6-(allyl-methyl-amino)-hexyloxy]-piperidine-1-sulfonic acid (phenyl)-amide and pharmaceutically acceptable salts thereof.

14. The compound of claim 7, wherein $A^{15}$ is phenyl substituted with at least one halogen.

15. A compound selected from the group consisting of 4-[6-(allyl-methyl-amino)-hexyloxy]-piperidine-1-sulfonic acid (4-chloro-phenyl)-amide and pharmaceutically acceptable salts thereof.

16. A compound selected from the group consisting of 4-[6-(allyl-methyl-amino)-hexyloxy]-piperidine-1-sulfonic acid (4-bromo-phenyl)-amide and pharmaceutically acceptable salts thereof.

17. A compound selected from the group consisting of 4-[6-(cyclopropyl-methyl-amino)-hexyloxy]-piperidine-1-sulfonic acid (3,4-difluoro -phenyl)-amide and pharmaceutically acceptable salts thereof.

18. A compound selected from the group consisting of 4-[6-(allyl-methyl-amino)-hexyloxy]-pipendine-1-sulfonic acid (2,5-difluoro-phenyl)-amide and pharmaceutically acceptable salts thereof.

19. The compound of claim 7, wherein $A^{15}$ is phenyl substituted with trifluoromethyl.

20. A compound selected from the group consisting of 4-[6-(allyl-methyl-amino)-hexyloxy]-piperidine-1-sulfonic acid (4-trifluoromethyl-phenyl)-amide and pharmaceutically acceptable salts thereof.

21. A compound of formula (Ia)

(Ia)

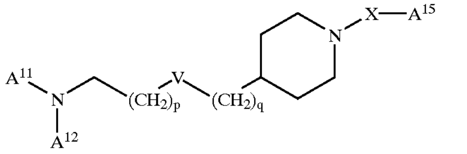

wherein

V is $—CH_2—$;

p is an integer from 0 to 5;

q 0, 1 or 2;

X is $SO_2$, or $SO_2NH$, with the proviso that:

a) p+q is 1 or 2 when V is $—CH_2—$ and X is $SO_2$, $A^{11}$ is methyl or ethyl;

$A^{12}$ is cyclopropyl, lower-alkenyl, or lower-alkyl optionally substituted with hydroxy or lower-alkoxy; and $A^{15}$ is lower-alkyl optionally substituted with halogen, lower-alkenyl, lower-alkoxy-carbonyl-lower-alkyl, cycloalkyl, cycloalkyl-lower-alkyl, aryl, aryl-lower-alkyl, heteroaryl, or heteroaryl-lower-alkyl; or pharmaceutically acceptable salts or esters of the compounds of formula (Ia).

22. A compound selected from the group consisting of methyl-propyl-{4-[1 -(4-trifluoromethyl-benzenesulfonyl)-piperidin-4-yl]-butyl}-amine and pharmaceutically acceptable salts thereof.

23. A compound of formula (Ia)

(Ia)

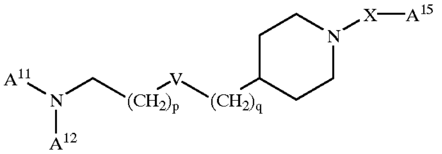

wherein

V is —CH=CH—;

p is an integer from 0 to 5;

q 0, 1 or 2;

X is $SO_2$, or $SO_2NH$, with the proviso that:

a) p=q=O when V is —CH=CH— and X is $SO_2$, $A^{11}$ is methyl or ethyl;

$A^{12}$ is cyclopropyl, lower-alkenyl, or lower-alkyl optionally substituted with hydroxy or lower-alkoxy; and $A^{15}$ is lower-alkyl optionally substituted with halogen, lower-alkenyl, lower-alkoxy-carbonyl-lower-alkyl, cycloalkyl, cycloalkyl-lower-alkyl, aryl, aryl-lower-alkyl, heteroaryl, or heteroaryl-lower-alkyl; or pharmaceutically acceptable salts or esters of the compounds of formula (Ia).

24. A compound of formula (Ia)

(Ia)

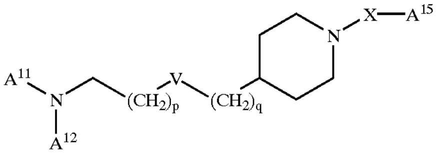

wherein

V is —C≡C—;

p is an integer from 0 to 5;

q 0, 1 or 2;

X is $SO_2$, or $SO_2NH$, $A^{11}$ is methyl or ethyl;

$A^{12}$ is cyclopropyl, lower-alkenyl, or lower-alkyl optionally substituted with hydroxy or lower-alkoxy; and $A^{15}$ is lower-alkyl optionally substituted with halogen, lower-alkenyl, lower-alkoxy-carbonyl-lower-alkyl, cycloalkyl, cycloalkyl-lower-alkyl, aryl, aryl-lower-alkyl, heteroaryl, or heteroaryl-lower-alkyl; or pharmaceutically acceptable salts or esters of the compounds of formula (Ia).

25. The compound of claim 24, wherein X is $SO_2$.

26. A compound selected from the group consisting of methyl-propyl-{3-[1-(4-trifluoromethyl-benzenesulfonyl)-piperidin-4-yl]-prop-2-ynyl}-amine and pharmaceutically acceptable salts thereof.

27. A compound selected from the group consisting of 2-(ethyl-{5-[1-(4-trifluoromethyl-benzenesulfonyl)-piperidin-4-yl]-pent-4-ynyl}-amino)-ethanol, pharmaceutically acceptable salts thereof and pharmaceutically acceptable esters thereof.

28. A compound selected from the group consisting of 2-(ethyl-{4-[1-(4-trifluoromethyl-benzenesulfonyl)-piperidin-4-yl]-but -3-ynyl}-amino)-ethanol, pharmaceutically acceptable salts thereof and pharmaceutically acceptable esters thereof.

29. A compound selected from the group consisting of ethyl-(2-methoxy-ethyl)-{4-[1-(4-trifluoromethyl-benzenesulfonyl)-piperidin-4-yl]-but-3-ynyl}-amine and pharmaceutically acceptable salts thereof.

30. The compound of claim 24, wherein X is $SO_2NH$.

31. A compound of formula (I)

(I)

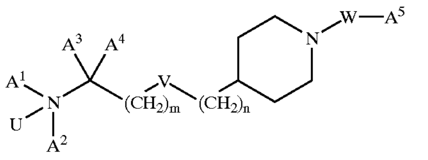

wherein

U is a lone pair;

V is —CH═CH—;

m and n are each integers from 0 to 7 and m+n is 0 to 7;

W is $SO_2$, or $SO_2NR^1$, with the provisos that:

a) m=n=O when V is —CH═CH— and W is $SO_2$;

$A^1$ is H, lower-alkyl or lower-alkenyl, $A^2$ is cycloalkyl, cycloalkyl-lower-alkyl, lower-alkenyl, lower-alkynyl or lower-alkyl optionally substituted with hydroxy, lower-alkoxy or lower-alkoxy-carbonyl, or $A^1$ and $A^2$ bond together to form $—A^1—A^2—$, wherein $—A^1—A^2—$ is lower-alkylene or lower-alkenylene, optionally substituted by $R^2$, and one $—CH_2—$ group of $—A^1—A^2—$ is optionally replaced by $NR^3$, S, or O;

$A^3$ and $A^4$ are independently hydrogen or lower-alkyl;

$A^5$ is lower-alkyl optionally substituted with halogen, lower-alkenyl, lower-alkoxy-carbonyl-lower-alkyl, cycloalkyl, cycloalkyl-lower-alkyl, aryl, aryl-lower-alkyl, heteroaryl, or heteroaryl-lower-alkyl;

$R^2$ is lower-alkyl, hydroxy, hydroxy-lower-alkyl, or $N(R^4, R^5)$;

$R^1$, $R^3$, $R^4$ and $R^5$ are independently hydrogen or lower-alkyl; and

When $A^1$ is not bonded to $A^2$, $A^1$ and $A^3$ optionally bond together to form $—A^1—A^3—$, wherein $—A^1—A^3—$ is lower-alkylene or lower-alkenylene, optionally substituted by $R^2$, and one $—CH_2—$ group of $—A^1—A^3—$ is optionally replaced by $NR^3$, S, or O; or pharmaceutically acceptable salts or esters of the compounds of formula (I).

32. A compound of formula (I)

(I)

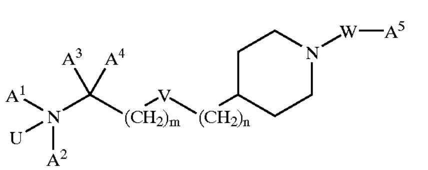

wherein

U is O or a lone pair;

V is $—CH_2—$, —CH═CH—, or —C≡C—;

m and n are each integers from 0 to 7 and m+n is 0 to 7;

W is $SO_2$, or $SO_2NR^1$, with the provisos that:

a) V is not $—CH_2—$ when W is CO, b) m+n is 1 or 2 when V is $—CH_2—$ and W is $SO_2$, c) m=n=0 when V is —CH═CH— and W is CO or $SO_2$, $A^1$ is H, lower-alkyl or lower-alkenyl, $A^2$ is cycloalkyl, cycloalkyl-lower-alkyl, lower-alkenyl, lower-alkynyl or lower-alkyl optionally substituted with hydroxy, lower-alkoxy or lower-alkoxy-carbonyl, or $A^1$ and $A^2$ bond together to form $—A^1—A^2—$, wherein $—A^1—A^2—$ is lower-alkylene or lower-alkenylene, optionally substituted by $R^{2,}$ and one $—CH_2—$ group of $—A^1—A^2—$ is optionally replaced by $NR^3$, S, or O;

$A^3$ and $A^4$ are independently hydrogen or lower-alkyl;

$A^5$ is lower-alkyl optionally substituted with halogen, lower-alkenyl, lower-alkoxy-carbonyl-lower-alkyl, cycloalkyl, cycloalkyl-lower-alkyl, aryl, aryl-lower-alkyl, heteroaryl, or heteroaryl-lower-alkyl;

$R^2$ is lower-alkyl, hydroxy, hydroxy-lower-alkyl, or $N(R^4, R^5)$;

$R^1$, $R^3$, $R^4$ and $R^5$ are independently hydrogen or lower-alkyl; and

When $A^1$ is not bonded to $A^2$, $A^1$ and $A^3$ optionally bond together to form $—A^1—A^3—$, wherein $—A^1—A^3—$ is lower-alkylene or lower-alkenylene, optionally substituted by $R^2$, and one $—CH_2—$ group of $—A^1—A^3—$ is optionally replaced by $NR^3$, S, or O; or pharmaceutically acceptable salts or esters of the compounds of formula (I).

33. The compound according to claim 32, wherein U is a lone pair.

34. The compound according to claim 33, wherein V is —C≡C—.

35. The compound according to claim 33, wherein V is $—CH_2—$.

36. The compound according to claim 33, wherein V is —CH═CH—.

37. The compound according to claim 33, wherein W is $SO_2$.

38. The compound according to claim 33, wherein W is $SO_2NH$.

39. The compound according to claim 33, wherein n is 0 to 2.

40. The compound according to claim 41, wherein n is 0.

41. The compound according to claim 33, wherein m is 1 to 5.

42. The compound according to claim 33, wherein m is 0 to 2.

43. The compound according to claim 33, wherein $A^1$ is methyl, ethyl or 2-propenyl.

44. The compound according to claim 43, wherein $A^2$ is methyl, n-propyl, i-propyl, n-butyl, 2-propenyl, 2-propinyl, cyclopropyl, cyclohexyl, cyclopropyl-methylene; or ethyl optionally substituted with hydroxy, methoxy, or ethoxycarbonyl.

45. The compound according to claim 44, wherein $A^2$ is n-propyl, 2-hydroxy-ethyl, 2-methoxy-ethyl, 2-propenyl, or cyclopropyl.

46. The compound according to claim 33, wherein $A^1$ and $A^2$ are bonded together to form $—A^1—A^2—$, wherein $R^2$ is lower-alkyl, hydroxy, hydroxy-lower-alykl, or $N(lower\text{-}alkyl)_2$, and $R^3$ is lower-alkyl.

47. The compound according to claim 46, wherein $R^2$ is methyl, hydroxy, 2-hydroxy-ethyl, or $N(CH_3)_2$, and $R^3$ is methyl.

48.The compound according to claim 33, wherein $A^3$ is hydrogen.

49. The compound according to claims 48, wherein $A^4$ is hydrogen.

50. The compound according to claim 33, wherein $A^5$ is lower-alkyl optionally substituted by 1 to 3 substituents selected from the group consisting of fluorine and chlorine; lower-alkenyl, cycloalkyl, cycloalkyl-lower-alkyl, lower-alkoxy-carbonyl-lower-alkyl, naphthyl, furyl-methylene; or phenyl, benzyl or phenyl-ethylene, optionally substituted by 1 to 3 substituents selected from the group consisting of fluorine, chlorine, bromine, CN, $CF_3$, $NO_2$, lower-alkyl, lower-alkoxy, thio-lower-alkoxy, lower-alkyl-carbonyl, lower-alkoxy-carbonyl, and dioxo-lower-alkylene.

51. The compound according to claim 50, wherein $A^5$ is lower-alkyl, cycloalkyl-lower-alkyl; or phenyl or benzyl optionally substituted by 1 to 3 substituents selected from the group consisting of fluorine, chlorine, bromine, and $CF_3$.

52. The compound according to claim 51, wherein $A^5$ is n-butyl, i-butyl, cyclohexyl-methylene, phenyl, 4-chloro-phenyl, 4-bromo-phenyl, 2,5-difluoro-phenyl, 3,4-difluoro-phenyl, 4-trifluoromethyl-phenyl, or 4-chloro-benzyl.

53. A process for the preparation of compounds according to claim 32, which process comprises reacting a compound of formula (II)

(II)

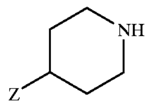

wherein Z is $(A^1,A^2)N—C(A^3,A^4)—(CH_2)_m—V—(CH_2)_n—$, $X—CH_2—(CH_2)_m—V—(CH_2)_n—$, $HO(CH_2)_n—$, or $HOOC(CH_2)_n—$, wherein X is chlorine, bromine, iodine, methanesulfonyl, or toluenesulfonyl, and $A^1$, $A^2$, $A^3$, $A^4$, V, m and n are as defined in claim 77, with $ClSO_2—A^5$, $ClCOO—A^5$, $ClCSO—A^5$, $OCN—A^5$, $SCN—A^5$, $HOOC—A^5$, or $ClSO_2NR^1—A^5$, wherein $A^5$ is as defined in claim 77.

54. A pharmaceutical composition comprising a compound according to claim 32, at least one of a pharmaceutically acceptable carrier or a pharmaceutically acceptable adjuvant.

55. A compound of formula (I)

(I)

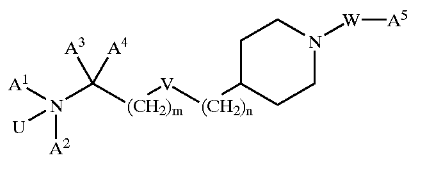

wherein

U is O or a lone pair;

V is O;

m and n are each integers from 0 to 7 and m +n is 0 to 7;

W is $SO_2NR^1$, with the provisos that:

a) m is 1 to 7 when V is O;

$A^1$ is H, lower-alkyl or lower-alkenyl, $A^2$ is cycloalkyl, cycloalkyl-lower-alkyl, lower-alkenyl, lower-alkynyl or lower-alkyl optionally substituted with hydroxy, lower-alkoxy or lower-alkoxy-carbonyl, or $A^1$ and $A^2$ bond together to form $—A^1—A^2—$, wherein $—A^1—A^2—$ is lower-alkylene or lower-alkenylene, optionally substituted by $R^2$, and one $—CH_2—$ group of $—A^1—A^2—$ is optionally replaced by $NR^3$, S, or O;

$A^3$ and $A^4$ are independently hydrogen or lower-alkyl;

$A^5$ is lower-alkyl optionally substituted with halogen, lower-alkenyl, lower-alkoxy-carbonyl-lower-alkyl, cycloalkyl, cycloalkyl-lower-alkyl, aryl, aryl-lower-alkyl, heteroaryl, or heteroaryl-lower-alkyl;

$R^2$ is lower-alkyl, hydroxy, hydroxy-lower-alkyl, or $N(R^4, R^5)$;

$R^1$, $R^3$, $R^4$ and $R^5$ are independently hydrogen or lower-alkyl; and

When $A^1$ is not bonded to $A^2$, $A^1$ and $A^3$ optionally bond together to form $—A^1—A^3—$, wherein $—A^1—A^3—$ is lower-alkylene or lower-alkenylene, optionally substituted by $R^2$, and one $—CH_2—$ group of $—A^1—A^3—$ is optionally replaced by $NR^3$, S, or O; or pharmaceutically acceptable salts or esters of the compounds of formula (I).

56. The compound according to claim 55, wherein U is a lone pair.

57. The compound according to claim 56, wherein n is 0 to 2.

58. The compound according to claim 56, wherein n is 0.

59. The compound according to claim 56, wherein m is 1 to 5.

60. The compound according to claim 56, wherein m is 0 to 2.

61. The compound according to claim 56, wherein $A^1$ is methyl, ethyl or 2-propenyl.

62. The compound according to claim 61, wherein $A^2$ is methyl, n-propyl, i-propyl, n-butyl, 2-propenyl, 2-propinyl, cyclopropyl, cyclohexyl, cyclopropyl-methylene; or ethyl optionally substituted with hydroxy, methoxy, or ethoxycarbonyl.

63. The compound according to claim 62, wherein $A^2$ is n-propyl, 2-hydroxy-ethyl, 2-methoxy-ethyl, 2-propenyl, or cyclopropyl.

64. The compound according to claim wherein $A^1$ and $A^2$ are bonded together to form —A1—A2—, wherein $R^2$ is lower-alkyl, hydroxy, hydroxy-lower-alykl, or N(lower-alkyl)$_2$, and $R^3$ is lower-alkyl.

65. The compound according to claim 64, wherein $R^2$ is methyl, hydroxy, 2-hydroxy-ethyl, or $N(CH_3)_2$, and $R^3$ is methyl.

66. The compound according to claim wherein $A^3$ is hydrogen.

67. The compound according to claims 66, wherein $A^4$ is hydrogen.

68. The compound according to claim 56, wherein $A^5$ is lower-alkyl optionally substituted by 1 to 3 substituents selected from the group consisting of fluorine and chlorine; lower-alkenyl, cycloalkyl, cycloalkyl-lower-alkyl, lower-alkoxy-carbonyl-lower-alkyl, naphthyl, furyl-methylene; or phenyl, benzyl or phenyl-ethylene, optionally substituted by 1 to 3 substituents selected from the group consisting of fluorine, chlorine, bromine, CN, $CF_3$, $NO_2$, lower-alkyl, lower-alkoxy, thio-lower-alkoxy, lower-alkyl-carbonyl, lower-alkoxy-carbonyl, and dioxo-lower-alkylene.

69. The compound according to claim 68, wherein $A^5$ is lower-alkyl, cycloalkyl-lower-alkyl; or phenyl or benzyl optionally substituted by 1 to 3 substituents selected from the group consisting of fluorine, chlorine, bromine, and $CF_3$.

70. The compound according to claim 69, wherein $A^5$ is n-butyl, i-butyl, cyclohexyl-methylene, phenyl, 4-chloro-phenyl, 4-bromo-phenyl, 2,5-difluoro-phenyl, 3,4-difluoro-phenyl, 4-trifluoromethyl-phenyl, or 4-chloro-benzyl.

71. A process for the preparation of compounds according to claim 55, which process comprises reacting a compound of formula (II)

(II)

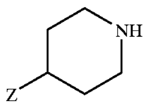

wherein Z is $(A^1,A^2)N—C(A^3,A^4)—(CH_2)_m—V—(CH_2)_n—$, $X—CH_2—(CH_2)_m—V—(CH_2)_n—$, $HO(CH_2)_n—$, or $HOOC(CH_2)_n—$, wherein X is chlorine, bromine, iodine, methanesulfonyl, or toluenesulfonyl, and $A^1$, $A^2$, $A^3$, $A^4$, V, m and n are as defined in claim 55, with $ClSO_2—A^5$, $ClCOO—A^5$, $ClCSO—A^5$, $OCN—A^5$, $SCN—A^5$, $HOOC—A^5$, or $ClSO_2NR^1—A^5$, wherein $A^5$ is as defined in claim 55.

72. A pharmaceutical composition comprising a compound according to claim 55 and at least one of a pharmaceutically acceptable carrier or a pharmaceutically acceptable adjuvant.

73. A compound of formula (I)

(I)

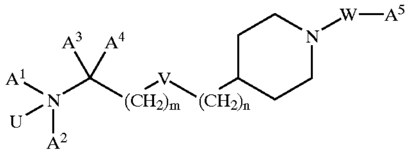

wherein

U is O or a lone pair;

V is O;

m and n are each integers from 1 to 7 and m+n is 1 to 7;

W is $SO_2$, $A^1$ is H, lower-alkyl or lower-alkenyl, $A^2$ is cycloalkyl, cycloalkyl-lower-alkyl, lower-alkenyl, lower-alkynyl or lower-alkyl optionally substituted with hydroxy, lower-alkoxy or lower-alkoxy-carbonyl, or $A^1$ and $A^2$ bond together to form $—A^1—A^2—$, wherein $—A^1—A^2—$ is lower-alkylene or lower-alkenylene, optionally substituted by $R^2$, and one $—CH_2—$ group of $—A^1—A^2—$ is optionally replaced by $NR^3$, S, or O;

$A^3$ and $A^4$ are independently hydrogen or lower-alkyl;

$A^5$ is lower-alkyl optionally substituted with halogen, lower-alkenyl, lower-alkoxy-carbonyl-lower-alkyl, cycloalkyl, cycloalkyl-lower-alkyl, aryl, aryl-lower-alkyl, heteroaryl, or heteroaryl-lower-alkyl;

$R^2$ is lower-alkyl, hydroxy, hydroxy-lower-alkyl, or $N(R^4, R^5)$;

$R^1$, $R^3$, $R^4$ and $R^5$ are independently hydrogen or lower-alkyl; and

When $A^1$ is not bonded to $A^2$, $A^1$ and $A^3$ optionally bond together to form $—A^1—A^3—$, wherein $—A^1—A^3—$ is lower-alkylene or lower-alkenylene, optionally substituted by $R^2$, and one $—CH_2—$ group of $—A^1—A^3—$ is optionally replaced by $NR^3$, S, or O; or pharmaceutically acceptable salts or esters of the compounds of formula (I).

74. A compound of formula (I)

(I)

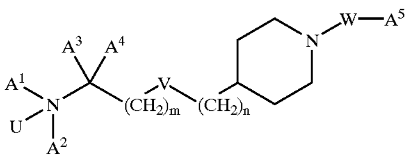

wherein

U is O or a lone pair;

V is O;

n is the integer 0;

m is an integer from 1 to 2;

W is $SO_2$, $A^1$ is H, lower-alkyl or lower-alkenyl, $A^2$ is cycloalkyl, cycloalkyl-lower-alkyl, lower-alkenyl, lower-alkynyl or lower-alkyl optionally substituted with hydroxy, lower-alkoxy or lower-alkoxy-carbonyl, or $A^1$ and $A^2$ bond together to form $—A^1—A^2—$, wherein $—A^1—A^2—$ is lower-alkylene or lower-alkenylene, optionally substituted by $R^2$, and one $—CH_2—$ group of $—A^1—A^2—$ is optionally replaced by $NR^3$, S, or O;

$A^3$ and $A^4$ are independently hydrogen or lower-alkyl;

$A^5$ is lower-alkyl optionally substituted with halogen, lower-alkenyl, lower-alkoxy-carbonyl-lower-alkyl, cycloalkyl, cycloalkyl-lower-alkyl, aryl, aryl-lower-alkyl, heteroaryl, or heteroaryl-lower-alkyl;

$R^2$ is lower-alkyl, hydroxy, hydroxy-lower-alkyl, or $N(R^4, R^5)$;

$R^1$, $R^3$, $R^4$ and $R^5$ are independently hydrogen or lower-alkyl; and

When $A^1$ is not bonded to $A^2$, $A^1$ and $A^3$ optionally bond together to form $—A^1—A^3—$, wherein $—A^1—A^3—$ is lower-alkylene or lower-alkenylene, optionally substituted by $R^2$, and one $—CH_2—$ group of $—A^1—A^3—$ is optionally replaced by $NR^3$, S, or O; or pharmaceutically acceptable salts or esters of the compounds of formula (I).

75. A compound of compounds of formula (Ia)

(Ia)

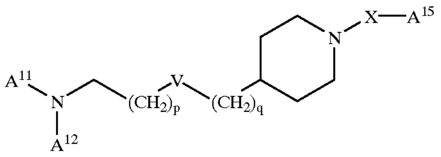

wherein

V is $—CH_2—$, $—CH{=}CH—$ or $—C{\equiv}C—$;

p is an integer from 0 to 5;

q 0, 1 or 2;

X is $SO_2$, or $SO_2NH$, with the provisos that:

a) p+q is 1 or 2 when V is $—CH_2—$ and X is $SO_2$, b) p=q=0 when V is $—CH{=}CH—$ and X is $SO_2$, $A^{11}$ is methyl or ethyl;

$A^{12}$ is cyclopropyl, lower-alkenyl, or lower-alkyl optionally substituted with hydroxy or lower-alkoxy; and $A^{15}$ is lower-alkyl optionally substituted with halogen, lower-alkenyl, lower-alkoxy-carbonyl-lower-alkyl, cycloalkyl, cycloalkyl-lower-alkyl, aryl, aryl-lower-alkyl, heteroaryl, or heteroaryl-lower-alkyl; or pharmaceutically acceptable salts or esters of the compounds of formula (Ia).

76. The compound of claim 75, wherein $A^{12}$ is cyclopropyl, lower alkenyl of 2 to 4 carbon atoms, lower alkyl of 1 to 4 carbon atoms, lower alkoxy of 1 to 4 carbon atoms, lower alkyl substituted with a lower-alkoxy having a total of 2 to 4 carbon atoms, or lower alkyl substituted with hydroxy.

77. The compound of claim 76, wherein $A^{15}$ is lower alkyl, cycloalkyl, cycloalkyl-lower alkyl, aryl or aryl-lower-alkyl.

78. The compound of claim 77, wherein V is $—CH_2—$.

79. The compound of claim 77, wherein V is —CH═CH—.

80. The compound of claim 77, wherein V is —C≡C—.

81. The compound of claim 80, wherein X is $SO_2$.

82. The compound of claim 80, wherein X is $SO_2NH$.

83. A compound of compounds of formula (Ia)

(Ia)

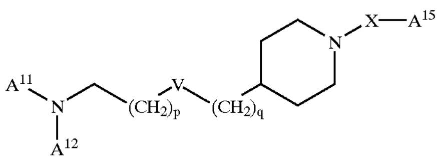

wherein

V is O;

p is an integer from 0 to 5;

q 0, 1 or 2;

X is $SO_2NH$, with the provisos that:

a) p is 1 to 5 when V is O;

$A^{11}$ is methyl or ethyl;

$A^{12}$ is cyclopropyl, lower-alkenyl, or lower-alkyl optionally substituted with hydroxy or lower-alkoxy; and $A^{15}$ is lower-alkyl optionally substituted with halogen, lower-alkenyl, lower-alkoxy-carbonyl-lower-alkyl, cycloalkyl, cycloalkyl-lower-alkyl, aryl, aryl-lower-alkyl, heteroaryl, or heteroaryl-lower-alkyl; or pharmaceutically acceptable salts or esters of the compounds of formula (Ia).

84. The compound of claim 83, wherein $A^{12}$ is cyclopropyl, lower alkenyl of 2 to 4 carbon atoms, lower alkyl of 1 to 4 carbon atoms, lower alkoxy of 1 to 4 carbon atoms, lower alkyl substituted with a lower-alkoxy having a total of 2 to 4 carbon atoms, or lower alkyl substituted with hydroxy.

85. The compound of claim 84, wherein $A^{15}$ is lower alkyl, cycloalkyl, cycloalkyl-lower alkyl, aryl or aryl-lower-alkyl.

86. The compound of claim 85, wherein $A^{15}$ is lower alkyl.

87. The compound of claim 85, wherein $A^{15}$ is cycloalkyl-lower-alkyl.

88. The compound of claim 85, wherein $A^{15}$ is phenyl.

89. The compound of claim 85, wherein $A^{15}$ is phenyl substituted with at least one halogen.

90. The compound of claim 85, wherein $A^{15}$ is phenyl substituted with trifluoromethyl.

* * * * *